(12) United States Patent
Davalos et al.

(10) Patent No.: US 7,634,360 B2
(45) Date of Patent: *Dec. 15, 2009

(54) CELLULAR FIBRONECTIN AS A DIAGNOSTIC MARKER IN STROKE AND METHODS OF USE THEREOF

(75) Inventors: Antoni Davalos, Girona (ES); Jose Castillo, Santiago De Compostela (ES); Mar Castellanos, St. Feliu De Guixols (Girona) (ES); Cornelius Allen Diamond, San Diego, CA (US)

(73) Assignee: Prediction Sciences, LL, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/046,592

(22) Filed: Jan. 29, 2005

(65) Prior Publication Data

US 2005/0130230 A1 Jun. 16, 2005

Related U.S. Application Data

(63) Continuation-in-part of application No. 10/948,834, filed on Sep. 22, 2004, now abandoned.

(60) Provisional application No. 60/505,606, filed on Sep. 23, 2003, provisional application No. 60/556,411, filed on Mar. 24, 2004.

(51) Int. Cl.
*A61B 5/00* (2006.01)
*G01N 33/48* (2006.01)
*G01N 33/50* (2006.01)
*C06F 19/00* (2006.01)

(52) U.S. Cl. .......................... 702/19; 435/7.1; 436/510; 600/300; 600/301

(58) Field of Classification Search ...................... None
See application file for complete search history.

(56) References Cited

U.S. PATENT DOCUMENTS 5,079,171 A * 1/1992 Senyei et al. ................. 436/510
2003/0100010 A1 * 5/2003 Jackowski et al. ........... 435/7.1

OTHER PUBLICATIONS

Hegele et al. Database Caplus, DN: 141:377907, 2004.*

* cited by examiner

*Primary Examiner*—Michael Borin
(74) *Attorney, Agent, or Firm*—Fuess & Davidenas

(57) ABSTRACT

The present invention relates to methods for the diagnosis and evaluation of stroke and stroke sub-type. A variety of biomarkers are disclosed for assembling a panel for such diagnosis and evaluation. Methods are disclosed for selecting markers and correlating their combined levels with a clinical outcome of interest. In various aspects: the invention provides methods for early detection and differentiation of stroke subtypes, for determining the prognosis of a patient presenting with stroke symptoms, and identifying a patient at risk for hemorrhagic transformation after thrombolyic therapy. Methods are disclosed that provide rapid, sensitive and specific assays to greatly increase the number of patients that can receive beneficial stroke treatment and therapy, and reduce the costs associated with incorrect stroke diagnosis.

11 Claims, 4 Drawing Sheets

FIGURE 1

|  | Hemorrhagic Transformation (n=26) | Nonhemorrhagic Transformation (n=61) | P |
|---|---|---|---|
| Male, n (%) | 11 (46.2) | 37 (63.9) | 0.156 |
| Age, y | 69.6±10.2 | 66.5±12.5 | 0.232 |
| Time from stroke onset to treatment, min | 158.6±32.4 | 159.8±50.4 | 0.897 |
| Clinical characteristics |  |  |  |
|   NIHSS score at admission | 15.9±4.1 | 12.4±5.4 | 0.003 |
|   Stroke subtype, n (%) |  |  | 0.331 |
|     Large-artery atherosclerosis | 8 (30.8) | 16 (26.2) |  |
|     Cardioembolism | 13 (50) | 27 (44.3) |  |
|     Small-vessel disease | 0 | 3 (4.9) |  |
|     Undetermined cause | 4 (15.4) | 15 (24.6) |  |
|     Others | 1 (3.8) | 0 |  |
|   Previous treatment with aspirin, n (%) | 5 (19.2) | 7 (11.5) | 0.332 |
| Biochemistry and vital signs at admission |  |  |  |
|   Plasma glucose, mg/dL | 147±41 | 151±60 | 0.736 |
|   Systolic blood pressure, mm Hg | 157±24 | 163±25 | 0.274 |
|   Diastolic blood pressure, mm Hg | 85±15 | 86±76 | 0.691 |
|   INR | 1.1±0.1 | 1.1±0.1 | 0.670 |
|   Platelet count, $10^5$/mm$^3$ | 218±60 | 217±59 | 0.976 |
| Neuroimaging findings |  |  |  |
|   Early signs of infarction, n (%) | 16 (61.5) | 21 (34.4) | 0.059 |
|   Volume of hypodensity at 24–36 h, mL | 107±163 | 29±60 | 0.002 |

Continuous variables are expressed as mean±SD.
INR indicates International Normalized Ratio.

FIGURE 2
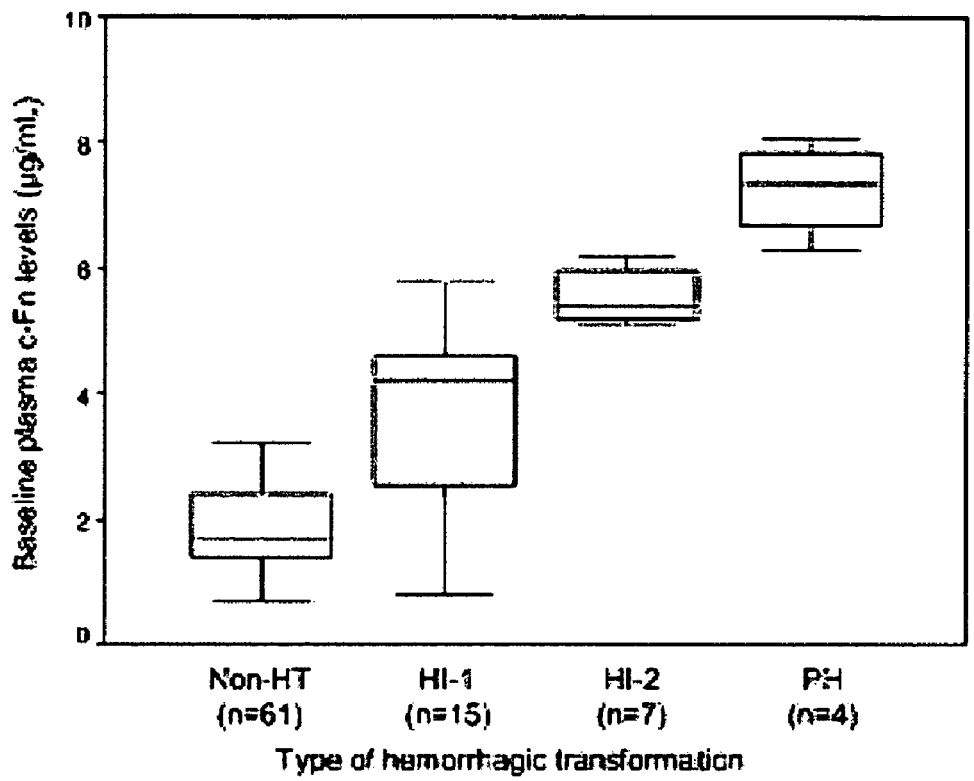
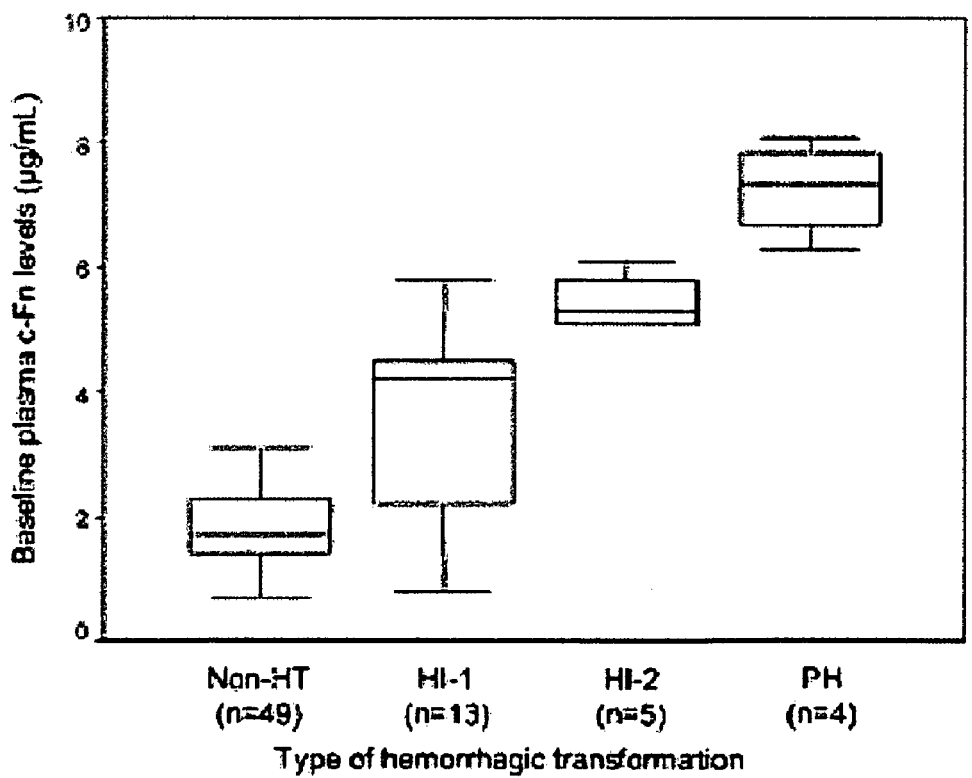

FIGURE 3
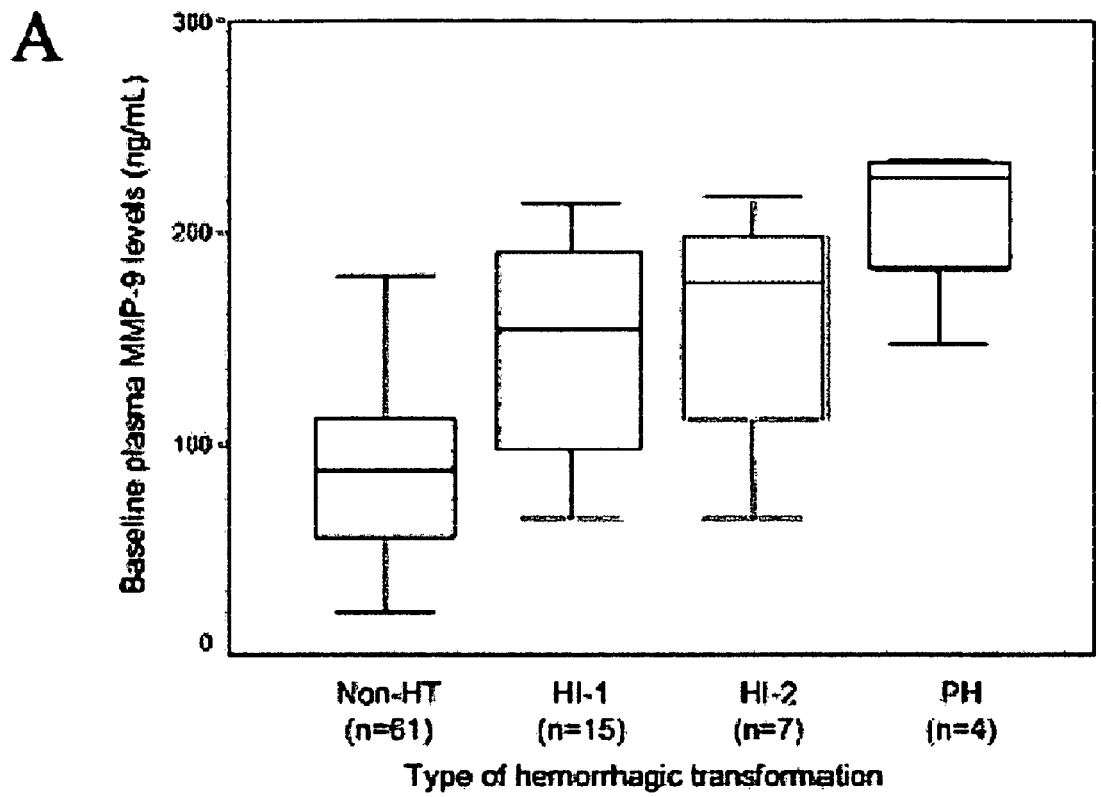
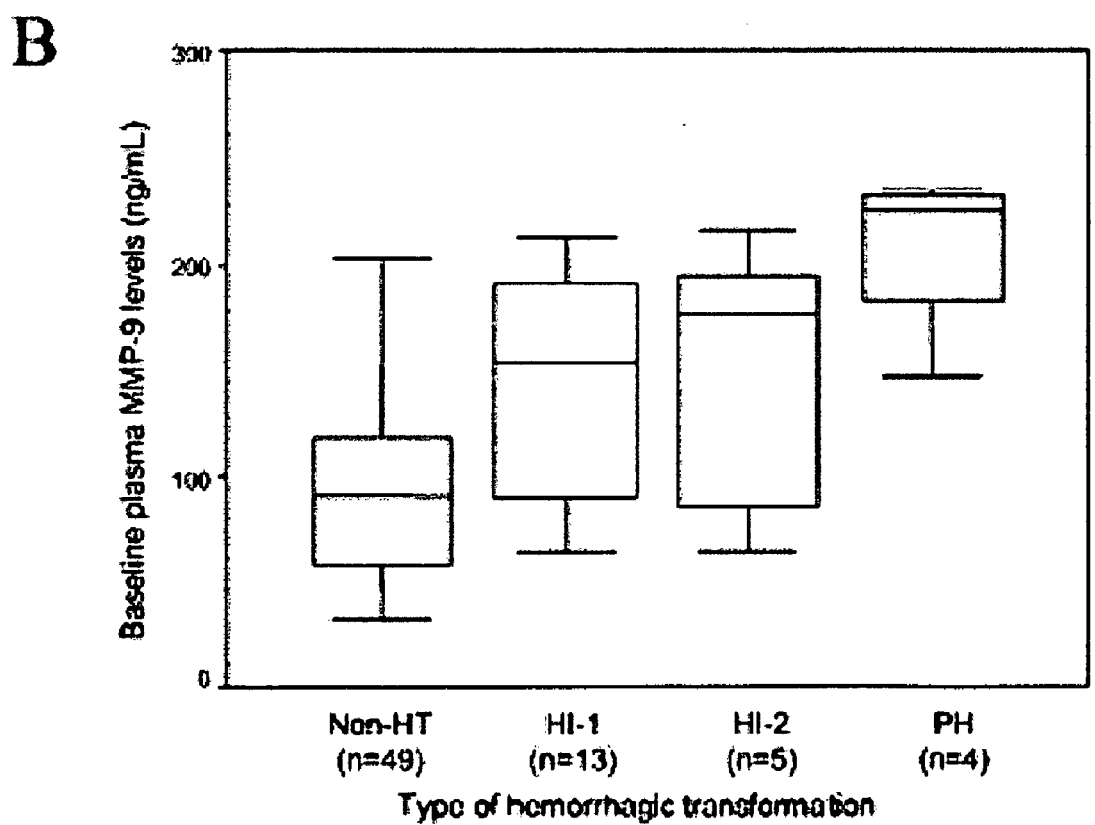

FIGURE 4

| Variables | OR (95% CI) | *P* |
|---|---|---|
| Age | 1.0 (0.9–1.1) | 0.780 |
| History of diabetes | 0.8 (0.2–3.6) | 0.740 |
| NIHSS score at admission | 1.1 (0.9–1.3) | 0.071 |
| MMP-9 levels (by 10-unit increase, ng/mL) | 1.1 (0.9–1.3) | 0.086 |
| c-Fn levels ($\mu$g/mL) | 2.1 (1.3–3.3) | 0.006 |

Age and history of diabetes were forced into the analysis.
CI indicates confidence interval.

CELLULAR FIBRONECTIN AS A DIAGNOSTIC MARKER IN STROKE AND METHODS OF USE THEREOF

RELATED APPLICATIONS

The present application is descended from, and claims benefit of priority of, U.S. provisional patent application No. 60/505,606 filed on Sep. 23, 2003, the contents of which of which are hereby incorporated herein in their entirety, including all tables, figures, and claims. The present application is a continuation-in-part of U.S. utility patent application Ser. No. 10/948,834 filed on Sep. 22, 2004 now abandoned, which application is itself descended from U.S. provisional patent application 60/505,606 and 60/556,411 filed on Mar. 24, 2004

FIELD OF THE INVENTION

The present invention generally relates to the identification and use of diagnostic markers for cardiovascular disease and cerebral injury. In a various aspects, the present invention particularly relates to methods for (1) the early detection and differentiation of cardiovascular events stroke and transient ischemic attacks, and (2) the identification of individuals at risk for hemorrhagic transformation after both presentation with stroke symptoms and subsequent administration of tissue plasminogen activator (tPA) therapy.

BACKGROUND OF THE INVENTION

The following discussion of the background of the invention is merely provided to aid the reader in understanding the invention and is not admitted to describe or constitute prior art to the present invention.

A stroke is a sudden interruption in the blood supply of the brain. Most strokes are caused by an abrupt blockage of arteries leading to the brain (ischemic stroke). Other strokes are caused by bleeding into brain tissue when a blood vessel bursts (hemorrhagic stroke). Because stroke occurs rapidly and requires immediate treatment, stroke is also called a brain attack. When the symptoms of a stroke last only a short time (less than an hour), this is called a transient ischemic attack (HT) or mini-stroke. Stroke has many consequences.

The effects of a stroke depend on which part of the brain is injured, and how severely it is injured. A stroke may cause sudden weakness, loss of sensation, or difficulty with speaking, seeing, or walking. Since different parts of the brain control different areas and functions, it is usually the area immediately surrounding the stroke that is affected. Sometimes people with stroke have a headache, but stroke can also be completely painless. It is very important to recognize the warning signs of stroke and to get immediate medical attention if they occur.

Stroke or brain attack is a sudden problem affecting the blood vessels of the brain. There are several types of stroke, and each type has different causes. The three main types of stroke are listed below.

Ischemic stroke is the most common type of stroke—accounting for almost 80% of strokes—an is caused by a clot or other blockage within an artery leading to the brain.

Intracerebral hemorrhage is a type stroke caused by the sudden rupture of an artery within the brain. Blood is then released into the brain, compressing brain structures.

Subarachnoid hemorrhage is also a type of stroke caused by the sudden rupture of the artery. A subarachnoid hemorrhage differs from an intracerebral hemorrhage in that the location of the rupture leads to blood filling the space surrounding the brain rather than inside of it.

Ischemic stroke occurs when an artery to the brain is blocked. The brain depends on its arteries to bring fresh blood from the heart and lungs. The blood carries oxygen and nutrients to the brain, and takes away carbon dioxide and cellular waste. If an artery is blocked, the brain cells (neurons) cannot make enough energy and will eventually stop working. If the artery remains blocked for more than a few minutes, the brain cells may die. This is why immediate medical treatment is absolutely critical.

Ischemic stroke can be caused by several different kinds of diseases. The most common problem is narrowing of the arteries in the neck or head. This is most often caused atherosclerosis, or gradual cholesterol deposition. If the arteries become too narrow, blood cells may collect and form blood clots. These blood clots can block the artery where they are formed (thrombosis), or can dislodge and become trapped in arteries closer to the brain (embolism). Another cause of stroke is blood clots in the heart, which can occur as a result of irregular heartbeat (for example, atrial fibrillation), heart attack, or abnormalities of the heart valves. While these are the most common causes of ischemic stroke, there are many other possible causes. Examples include use of street drugs, traumatic injury to the blood vessels of the neck, or disorders of blood clotting.

Ischemic stroke can further be divided into two main types: thrombotic and embolic.

A thrombotic stroke occurs when diseased or damaged cerebral arteries become blocked by the formation of a blood clot within the brain. Clinically referred to as cerebral thrombosis or cerebral infarction, this type of event is responsible for almost 50% of all strokes. Cerebral thrombosis can also be divided into an additional two categories that correlate to the location of the blockage within the brain: large-vessel thrombosis and small-vessel thrombosis. Large-vessel thrombosis is the term used when the blockage is in one of the brain's larger blood-supplying arteries such as the carotid or middle cerebral, while small-vessel thrombosis involves one (or more) of the brain's smaller, yet deeper penetrating arteries. This latter type of stroke is also called a lacuner stroke.

An embolic stroke is also caused by a clot within an artery, but in this case the clot (or emboli) was formed somewhere other than in the brain itself. Often from the heart, these emboli will travel the bloodstream until they become lodged and cannot travel any further. This naturally restricts the flow of blood to the brain and results in almost immediate physical and neurological deficits.

Thrombolytic therapy has been proven to be effective for the treatment of acute ischemic stroke, but the increased risk of tissue plasminogen activator (tPA) is still of great clinical concern (see for instance The National Institutes of Neurological Disorders, and Stroke rt-PA Stroke Study Group. Tissue plasminogen activator for acute ischemic stroke. New England Journal of Medicine 1995;333:1581-7).

As it is critical to restore proper blood flow to the brain as soon as possible to prevent tissue damage, rapid diagnosis of stroke is critical to the survival of the patient and the minimization of any effects of the stroke to the patient. If caught from three to six hours after occurrence most stroke patients can expect full or parHTI recovery Current state of the art diagnosis of stroke involves a physical examination and imaging procedures such as computed tomography (CT) scan, angiogram, electrocardiogram, magnetic resonance imaging (MRI), Single photon emission computed tomography (SPECT) and positron emission tomography (PET).

While physical examination is rapid, it only can detect large strokes (defined to be significant impairment of symptoms on the National Institutes of Health Stroke Scale, (NIHSS) of greater than 12). In addition, prior studies have found that the accuracy of stroke identification by medical personnel is modest and variable from one community to another. Sensitivity for stroke recognition by prehospital personnel has ranged widely, and positive predictive values have remained between 64% and 77% (see for instance Zweifler R M, York D, U T T, Mendizabal J E, Rothrock J F. Accuracy of paramedic diagnosis of stroke. *J Stroke Cerebrovasc Dis.* 1998;7:446-448.). These studies have consistently suggested a tendency for prehospital personnel to overdiagnose stroke by not recognizing stroke mimics, such as patients with alcohol and drug intoxication, postictal hemiparesis, hypoglycemia or other metabolic encephalopathies, and other nonstroke causes of acute neurological deficits. Finally, any clinical neurological screening test will be limited by the training and experience of the examiner. This suggests the need for an adjunctive clinical test that can provide diagnostic information above and beyond screening clinical exams.

CT scan produces x-ray images of the brain and is used to determine the location and extent of hemorrhagic stroke. It has widespread availability. CT scan usually cannot produce images showing signs of ischemic stroke until 48 hours after onset. This insensitivity to acute stroke limits its use to post-stroke damage assessment.

SPECT and PET involve injecting a radioactive substance into the bloodstream and monitoring it as it travels through blood vessels in the brain. These tests allow physicians to detect damaged regions of the brain resulting from reduced blood flow. However, this takes several hours, and thus is not used for rapid diagnosis of stroke.

MRI with magnetic resonance angiography (MRA) uses a magnetic field to produce detailed images of brain tissue and arteries in the neck and brain, allowing physicians to detect small-vessel infarct (i.e., stroke in small blood vessels deep in brain tissue). However, as a practical issue, most hospitals do not have these specialized and highly expensive MRI services available in the acute setting. Thus, without a practical and widely available radiological test, the diagnosis of stroke remains largely a clinical decision.

Thrombolytic therapy has been proven to be effective for the treatment of acute ischemic stroke, but the increased risk of hemorrhagic transformation (HT) associated with tissue plasminogen activator (tPA) administration is still of great clinical concern. HT after cerebral ischemia seems to be related to the disruption of the vascular endothelium (see for instance Hamann G F, Okada Y, del Zoppo G J. Hemorrhagic transformation and microvascular integrity during focal cerebral ischemia/reperfusion. *J Cereb Blood Flow Metab.* 1996; 16:1373-1378.). In patients who receive tPA treatment, endothelial injury may be the result of free radical generation secondary to thrombolytic-induced reperfusion (see for instance), as well as of the upregulation of matrix metalloproteinases (MMPs) (see for instance Lapchak P A, Chapman D F, Zivin J A. Pharmacological effects of the spin trap agents N-t-butyl-phenylnitrone (PBN) and 2,2,6,6-tetramethylpiperidine-N-oxyl (TEMPO) in a rabbit thromboembolic stroke model: combination studies with the thrombolytic tissue plasminogen activator. *Stroke.* 2001;32:147-152.), a group of enzymes that are able to degrade the basal membrane components. The association between high levels of MMP-9 and the risk of HT in patients with acute ischemic stroke who have and have not received tPA have been previously reported (see for instance Sumii T, Lo E H. Involvement of matrix metalloproteinase in thrombolysis-associated hemorrhagic transformation after embolic focal ischemia in rats. *Stroke.* 2002; 33:831-836.; Montaner J, Molina C A, Monasterio J, Abilleira S, Arenillas J F, Ribo M, Quintana M, Alvarez-Sabin J. Matrix metalloproteinase-9 pretreatment level predicts intracranial hemorrhagic complications after thrombolysis in human stroke. *Circulation.* 2003;107:598-603.). However, despite the available data, the underlying molecular mechanisms related to HT after thrombolytic treatment have yet to be fully elucidated.

Accordingly, there is a present need in the art for a rapid, sensitive and specific differential diagnostic assay for stroke, stroke subtype, and stroke mimic that can also identify those individuals at risk for hemorrhagic transformation after presentation with stroke symptoms and subsequent administration of tPA therapy. Such a diagnostic assay would greatly increase the number of patients that can receive beneficial stroke treatment and therapy and in so doing reduce the costs associated with incorrect stroke diagnosis. Some content of this patent application was first published in the journal Stroke in its May 27, 2004, electronic issue.

BRIEF SUMMARY OF THE INVENTION

The present invention relates to the identification and use of diagnostic markers for stroke, endothelial damage and hemorrhagic transformation (HT) after thrombolytic therapy. The methods and compositions described herein can meet a need in the healing arts for rapid, sensitive and specific diagnostic assay to be used in the diagnosis and differentiation of various cardiac events. Moreover, the methods and compositions of the present invention can also be used to facilitate the treatment of stroke patients and the development of additional diagnostic and/or prognostic indicators.

In various aspects, the present invention relates to (1) materials and procedures for identifying markers that are associated with the diagnosis, prognosis, or differentiation of stroke and/or determination of HT in a patient; (2) using such markers in diagnosing and treating a patient and/or monitoring the course of a treatment regimen; (3) using such markers to identify subjects at risk for one or more adverse outcomes related to stroke and/or determination of HT; and (4) using at one of such markers an outcome marker for screening compounds and pharmaceutical compositions that might provide a benefit in treating or preventing such conditions.

In one of its aspects, the invention discloses methods for determining a diagnosis or prognosis related to a cardiac event such as stroke, or for differentiating between stroke sub-type and/or determination of HT. The preferred method includes analyzing a fluid sample obtained from a person who has an unknown diagnosis for the levels of one or more markers specific to the damage caused by said cardiac event. In the case of stroke, these markers would be drawn from the group consisting of markers relating to vascular damage, glial activation, inflammatory mediation, thrombosis, cellular injury, apoptosis, myelin breakdown, and specific and non-specific markers of cerebral injury. The analysis of the preferred method thus more precisely includes identifying one or more markers the presence or amount of which is associated with the diagnosis, prognosis, or differentiation of stroke and/or determination of HT. Once such marker(s) are identified, the next in the method the level of such marker(s) in a sample obtained from a subject of interest can be measured. In certain embodiments of the preferred method, these markers can be compared to a level that is associated with the diagnosis, prognosis, or differentiation of stroke and/or determination of HT. By correlating the subject's marker level(s) to the diagnostic marker level(s), the presence or absence of stroke, and also the probability of future adverse outcomes, etc., in a patient may be rapidly and accurately determined.

In another of its aspects, the instant invention is embodied in methods for choosing one or more marker(s) for differentiation of stroke and/or determination of HT that together, and as a group, have maximal sensitivity, specificity, and predictive power. Said maximal sensitivity, specificity, and predictive power is in particular realized by choosing one or more markers as constitute a group by process of plotting receiver operator characteristic (ROC) curves for (1) the sensitivity of a particular combination of markers versus (2) specificity for said combination at various cutoff threshold levels. In addition, the instant invention further discloses methods to interpolate the nonlinear correlative effects of one or more markers chosen by any methodology to such that the interaction between markers of said combination of one or more markers promotes maximal sensitivity, specificity, and predictive accuracy in the prediction of any of the occurrence of stroke, identification of stroke subtype, or likelihood of HT.

For purposes of the following discussion, the methods described as applicable to the diagnosis and prognosis of stroke generally may be considered applicable to the diagnosis and prognosis of other cardiac events.

The term "marker" as used herein refers to proteins or polypeptides to be used as targets for screening test samples obtained from subjects. "Proteins or polypeptides" used as markers in the present invention are contemplated to include any fragments thereof, in particular, immunologically detectable fragments. One of skill in the art would recognize that proteins which are released by cells of the central nervous system which become damaged during a cerebral attack could become degraded or cleaved into such fragments. Additionally, certain markers are synthesized in an inactive form, which may be subsequently activated, e.g., by proteolysis. Examples of such markers are described hereinafter. The term "related marker" as used herein refers to one or more fragments of a particular marker that may be detected as a surrogate for the marker itself. These related markers may be, for example, "pre," "pro," or "prepro" forms of markers, or the "pre," "pro," or "prepro" fragment removed to form the mature marker. Exemplary markers that are synthesized as pre, pro, and prepro forms are described hereinafter. In preferred embodiments, these "pre," "pro," or "prepro" forms or the removed "pre," "pro," or "prepro" fragments are used in an equivalent fashion to the mature markers in the methods described herein.

Preferred markers of the invention can (1) differentiate between ischemic stroke, hemorrhagic stroke, and stroke mimics, and also (2) predict HT in subjects. Preferred markers are drawn from the group including c-Fn, MMP-9, myelin basic protein, IL-1, IL-1rα, IL-1β, IL-8, IL-10, NCAM, VCAM, ICAM, S100b, HSP60, BDNF, D-Dimer, TGF-α, NT-3, VEGF, CK-BB, caspase 3, MCP-1 Calbindin-D, thrombin-antithrombin III complex, tissue factor, GFAP, NSE-γγ, vWF, VEGF, FPA, and NR2A. Each of these terms are defined hereinafter. Particularly preferred markers from this group are ones that have proven highly predictive of hemorrhagic transformation: namely, cellular fibronectin (c-Fn) and matrix metalloprotein-9 (MMP-9).

Those of ordinary skill in the art know that marker levels vary at certain time points; for example, the level of a marker may be at one level at three hours post-stroke event, and another level at nine hours post-stroke event. Thus when using multiple markers together which may or may not be correlated with each other it is necessary to provide interpretation through an algorithm that relates all markers together. This algorithm in current state of the art is a simple threshold level above which a marker is said to be indicative of an adverse event in the human body. A particular diagnosis and/or prognosis of said adverse event may depend upon the comparison of each marker to this value; alternatively, if only a subset of markers are outside of a normal range, then this subset may be indicative of a said adverse event.

Thus, in certain embodiments of the methods of the present invention, a plurality of markers are combined using an algorithm to increase the predictive value of the analysis in comparison to that obtained from the markers taken individually or in smaller groups. Most preferably, one or more markers for vascular damage, glial activation, inflammatory mediation, thrombosis, cellular injury, apoptosis, myelin breakdown, and specific and non-specific markers of cerebral injury are combined in a single assay to enhance the predictive value of the described methods. This assay is usefully predictive of multiple outcomes, for instance: determining whether or not a stroke occurred, then determining the subtype of stroke, then further predicting stroke prognosis. Moreover, different marker combinations in the assay may be used for different indications. Correspondingly, different algorithms interpret the marker levels as indicated on the same assay for different indications.

Preferred panels comprise markers for the following purposes: (1) diagnosis of stroke; (2) diagnosis of stroke mimics; (3) diagnosis of stroke and indication if an acute stroke has occurred; (4) diagnosis of stroke and indication if an non-acute stroke has occurred; (5) diagnosis of stroke, indication if an acute stroke has occurred, and indication if an non-acute stroke has occurred; (6) diagnosis of stroke and indication if an ischemic stroke has occurred; (7) diagnosis of stroke and indication if a hemorrhagic stroke has occurred; (8) diagnosis of stroke, indication if an ischemic stroke has occurred, and indication if a hemorrhagic stroke has occurred; (9) diagnosis of stroke and prognosis of a subsequent adverse outcome; (10) diagnosis of stroke and prognosis of a subsequent hemorrhagic transformation; and (11) diagnosis of stroke, indication if a hemorrhagic stroke has occurred, and further diagnosis of whether a subarachnoid hemorrhagic stroke has occurred.

In preferred embodiments, particular thresholds for one or more markers in a panel are not relied upon to determine if a profile of marker levels obtained from a subject are indicative of a particular diagnosis/prognosis. Rather, in accordance with the present invention, an evaluation of the entire profile is made by (1) first training an algorithm with marker information from samples from a test population and a disease population to which the clinical outcome of interest has occurred to determine weighting factors for each marker, and (2) then evaluating that result on a previously unseen population. Certain persons skilled in bioinformatics will recognize this procedure to be tanatamount to the construction, and to the training, of a neural network. The evaluation is determined by maximizing the numerical area under the ROC curve for the sensitivity of a particular panel of markers versus specificity for said panel at various individual marker levels. From this number, the skilled artisan can then predict a probability that a subject's current marker levels in said combination is indicative of the clinical marker of interest. For example, (1) the test population might consist solely of samples from a group of subjects who have had ischemic stroke and no other comorbid disease conditions, while (2) the disease population might consist solely of samples from a group of subjects who have had hemorrhagic stroke and no other comorbid disease conditions. A third, "normal" population might also be used to establish baseline levels of markers as well in a non-diseased population.

In preferred embodiments of the marker, and marker panel, selection methods of the present invention, the aforementioned weighting factors are multiplicative of marker levels in a nonlinear fashion. Each weighting factor is a function of other marker levels in the panel combination, and consists of terms that relate individual contributions, or independent and correlative, or dependent, terms. In the case of a marker having no interaction with other markers in regards to then clinical outcome of interest, then the specific value of the dependent terms would be zero.

The term "test sample" as used in this specification refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine and saliva. In addition, one of skill in the art would realize that some test samples would be more readily analyzed following a fractionation or purification procedure, for example, separation of whole blood into serum or plasma components.

The term "markers of glial activation" as used in this specification refers to markers that indicate glial cell function. Glia mediate neuroendocrine and neuroimmune functions and are also important in synaptic remodeling and the loss of synaptic connections that occur during aging. These functions are carried out by changes in glia, including changes in shape, interactions with neurons and other glia, and gene expression. The predominant change that occurs in glia during aging is glial activation, which can progress to reactive gliosis in response to neurodegeneration. Markers distinguish normal and reactive glia. During aging, astrocytes hypertrophy and exhibit signs of metabolic activation, and astrocytic processes surround neurons. Microglia also become activated and subsets of activated microglial increase in number and may enter the phagocytic or reactive stage. Yet glial cells are intimately involved in the biochemical metabolic and neurotrophic support of the function of neurons, and glial actions at the synapses are crucial to normal neuronal transmission. Glia take up excess glutamate (which can be neurotoxic) and produce neurotrophic factors which keep cells alive, as well as interacting with other systems in transmitter-like actions. Thus, a loss of normal glial function could have dramatic impacts on normal neuronal function. Such specific markers of glial activation include, but are not limited to, GFAP, S100B, Mac-1, TLR4, TGF-β1 and CD14.

The term "markers of vascular damage" as used in this specification refers to markers that indicate endothelial damage. When the endothelium is damaged or becomes dysfunctional, a cascade leading to atherogenesis is precipitated, initiating a cycle of injury, immunologic induction, and amplification. Dysfunctional endothelium leads to increased permeability to lipoproteins and up-regulation of leukocyte and endothelial adhesion molecules. In response to the presence of certain activating substances, including oxidized LDL, monocyte chemotactic protein 1, interleukin (IL)-8, and platelet-derived growth factor (PDGF), leukocytes migrate into the wall of the artery. Such specific markers of vascular damage include, but are not limited to, endothelin-1 (ET-1), von Willebrand factor (vWf), and soluble (S—) adhesion molecules E-selectin, intercellular adhesion molecule-1 (ICAM-1), vascular cell adhesion molecule-1 (VCAM-1), plasma indexes of endothelial damage/dysfunction and soluble thrombomodulin (sTM).

The term "markers of inflammatory mediation" as used in this specification refers to markers that indicate an inflammatory response to a cerebral injury. Inflammatory responses are initiated and perpetuated by the interaction of immune cells with cells of the affected vessel wall. This is directed by a network of chemical messengers, which, in a state of vascular health, exist as balanced but opposing forces. These markers include various cytokines, proteases, adhesion molecules, and acute phase proteins as participants in the generation of vascular inflammation. Such specific markers of vascular damage include, but are not limited to, Cellular adhesion molecules such as Intracellular adhesion molecule-1, Vascular cellular adhesion molecule-1, NCAM and Selectins such as E-Selectin; Chemokines such as monocyte chemoattractant protein-1; Cytokines such as Interleukins 1, 1β, 1 receptor antagonist, 6, 8, 10, 18, transforming growth factor β, and Tumor necrosis factor-α; Proteases such as the matrix metalloproteinases MMP-9, MMP-3, and MMP-2; Accessory signaling markers such as CD40/CD40L; and acute phase proteins such as C-reactive protein, vascular endothelial growth factor, ceruloplasmin, fibrinogen, a 1-acid glycoprotein, α1-antitrypsin, and haptoglobin.

The term "markers of thrombosis" as used in this specification refers to markers that indicate an coagulation event in ischaemic stroke. The blood clotting system is activated when blood vessels are damaged, exposing collagen, the major protein that connective tissue is made from. Platelets circulating in the blood adhere to exposed collagen on the cell wall of the blood vessel and secrete chemicals that start the clotting process as follows: Platelet aggregators cause platelets to clump together (aggregate). They also cause the blood vessels to contract (vasoconstrict), which reduces blood loss. Platelet aggregators include adenosine diphosphate (ADP), thromboxane A2, and serotonin (5-HT). Coagulants such as fibrin then bind the platelets together to form a permanent plug (clot) that seals the leak.

Fibrin is formed from fibrinogen in a complex series of reactions called the coagulation cascade. The enzymes that comprise the coagulation system are called coagulation factors, which are numbered in the order in which they were discovered. They include factor XII, factor XI, factor IX, factor X, factor VII, and factor V. The activation of the coagulation factors results in the formation of thrombin, which acts as a cofactor for the conversion of fibrinogen into fibrin. After the leak has been sealed with a blood clot, the body responds with another set of chemical messengers that oppose the actions of these chemicals. These include: Platelet aggregation inhibitors and vasodilators, such as nitric oxide and prostacyclin, which is also known as prostaglandin 12 (PGI2) Plasminogen activators that promote the breakdown of fibrin, such as tissue plasminogen activator (t-PA) Anticoagulants that inhibit enzymes in the coagulation cascade, such as antithrombin III (activated by heparin) and proteins C and S.

Such specific markers of thrombosis include, but are not limited to, von Willebrand factor, thrombin-antithrombin III complex, proteins C and S, tissue factor, fibrinopeptide A, plasmin-α-2-antiplasmin complex, prothrombin fragment 1+2, D-dimer, platelet factor 4, and β-thromboglobulin.

The term "marker of cellular injury and myelin breakdown" as used in this specification refers to markers associated with damage to the structural and functional molecules of the cell. Although any biologically important molecule in a cell can be the target of injury producing stress, four biochemical systems are particularly vulnerable: (1) the cell membrane, (2) energy metabolism, (3) protein synthesis, and (4) genes. Because many of the biochemical systems of the cell are inter-dependent, injury at one site typically leads to secondary injury to other cellular processes.

Myelin is the outer lipid rich (fatty) layer that covers nerves and nervous system pathways in the brain and spinal cord. The myelin sheath, a lipid-rich multilamellar membrane of relative stability, both insulates and enhances conduction in nerve axons. A notable feature of myelin-specific proteins, in particular myelin basic protein, is their susceptibility to proteolytic activity and their encephalitogenicity, which induces inflammatory demyelination in the CNS. The final common pathway of myelin breakdown in vivo is well documented and there is evidence that myelin disruption can be mediated directly by soluble (circulating) factors and for following receptor-driven phagocytosis by macrophages. However the exact mechanism(s) of demyelination in ischemic attack is still unresolved, both antigen-specific and—non-specific events having the potential to generate the myelinolytic process.

Cerebral injury leads to breakdown of the blood-brain barrier (BBB), exposing CNS antigens to the peripheral circulation and allowing the peripheral circulation access to the brain. The breakdown of the BBB leads to rapid acquisition of MBP-reactive T cell clones and Igs in stroke patients but does not lead to autoimmune encephalitis. The degradation of myelin basic protein (MBP) by proteinase yields encephalitogenic peptides and its loss has been found to cause structural alteration of the myelin sheath. This suggests that MBP degradation is an initial step in the breakdown of myelin in demyelinating diseases. A calcium-activated neutral proteinase (calpain), which degrades MBP, was found to increase in activity in MS tissue and cerebrospinal fluid (CSF), and its presence in myelin suggests that myelin may be autodigested in demyelinating disease. The source of increased proteinase activity has been indicated as macrophages, lymphocytes, and proliferative astrocytes (reactive cells). Increased proteinase activity is found in Schwann cells in Wallerian degeneration, and the presence of calpain in myelin-forming oligodendrocytes and Schwann cells suggests that these cells are likely sources of degradative enzymes.

Such specific markers of cellular injury and myelin breakdown include, but are not limited to, creatinine phosphokinase brain band, tissue factor, Proteolipid protein, RU Malendialdehyde, calpain, and myelin basic protein.

The term "marker of apoptosis or growth factors" as used in this specification refers to markers involved in neuronal cell death. Numerous studies in experimental models of ischemia have now reported that apoptosis contributes to neuronal death (reviewed by Chalmers-Redman et al Mechanisms of nerve cell death: apoptosis or necrosis after cerebral ischemia. In: Green A R, Cross A J, eds. *Neuroprotective Agents and Cerebral Ischemia*. San Diego, Calif.: Academic Press; 1997:1-25.). Apoptosis requires the activation of a "cell death" gene program, and many of the extracellular signals that regulate apoptosis have been identified. For example, interaction between the Fas/APO-1 molecule, a cell surface protein, with its ligand (Fas-L) leads to programmed cell death. Soluble (s) Fas/APO-1, a molecule lacking the transmembrane domain of Fas/APO-1, blocks apoptosis by inhibiting interaction between Fas/APO-1 and Fas-L on the cell surface (see for instance Cheng J et al., Protection from Fas-mediated apoptosis by a soluble form of the Fas molecule. *Science*. 1994;263:1759-1762.). Fas expression has been detected on B and T cells and on neutrophils. It has been suggested that the Fas/Fas-L pathway is one of the major mechanisms for T-cell-mediated cytotoxicity. It has also been demonstrated by in situ hybridization that the expression of Fas/APO-1 was induced in murine brain after transient global cerebral ischemia. Another gene product, bcl-2, has been shown to suppress apoptosis and to protect primary neuronal cell cultures from apoptosis induced by nerve growth factor depletion.

Macrophages and T lymphocytes kill target cells by inducing apoptosis, one of the potential mechanisms whereby the inflammatory cells invading the infarcted brain area participate in neuronal cell death. Stroke patients displayed an intrathecal production of proinflammatory cytokines, such as interleukin (IL)-1β, IL-6, IL-8, and granulocyte-macrophage colony-stimulating factor (GM-CSF), and of the anti-inflammatory cytokine IL-10 within the first 24 hours after the onset of symptoms, supporting the notion of localized immune response to the acute brain lesion in humans. Some of these cytokines (eg, IL-1β and IL-8) stimulate influx of leukocytes to the infarcted brain, a prerequisite for Fas/APO-1- and bcl-2-mediated apoptosis. TNF-α, a powerful cytokine inducing apoptosis in the extraneural compartment of the body, has been demonstrated to protect rat hippocampal, septal, and cortical cells against metabolic-excitotoxic insults and to facilitate regeneration of injured axons. More importantly, TNF-α and -β protect neurons against amyloid β-protein-triggered toxicity.

Other evidence demonstrates that apoptosis involves the activation of caspases, a unique family of structurally related, highly conserved, aspartate-specific, cysteine proteases that are necessary to carry out the signal for apoptotic cell death. Two members of the caspase family, caspase-1 and caspase-3, are known to cleave the most abundant caspase target substrate, actin. The 45-kDa actin is cleaved by caspase activation between Asp11 and Asn12 and between Asp244 and Gly245 to produce N-terminal 32-kDa fragments and C-terminal 15-kDa fragments. A polyclonal antibody to the last 5 amino acids of the C-terminus of the 32-kDa fragment of actin generated by caspase cleavage of intact actin has been developed and named "fractin" for "fragment of actin." Fractin labeling provides indirect evidence of caspase activation and demonstrates initiation of an apoptotic pathway, but does not rule out secondary necrosis. Other markers for apoptosis include biochemical evidence of oligointernucleosomal DNA fragmentation into approximately 180-bp multiples resulting from endonuclease activation that can be demonstrated with a typical "laddering" appearance on agarose gel electrophoresis. In addition, the terminal deoxynucleotidyl transferase-mediated dUTP-biotin nick end labeling (TUNEL) technique, which identifies 3'-OH ends of DNA-strand breaks, has been widely used as a marker of DNA damage or repair. However, the lack of specificity of TUNEL in detecting oligointernucleosomal DNA fragmentation precludes its use as a defining feature of apoptosis.

Such specific markers of apoptosis and growth factors include, but are not limited to, Brain natriuretic peptide, caspase 3, calbindin-D, heat shock protein 60 and 70, c-fos, c-jun, ubiquitin, and cytochrome C.

The term "specific marker of cerebral injury" as used in this specification refers to proteins or polypeptides that are associated with brain tissue and neural cells, and which can be correlated with a cerebral injury, but are not correlated with other types of injury. Such specific markers of cerebral injury include, but are not limited to, adenylate kinase, brain-derived neurotrophic factor, calbindin-D, lactate dehydrogenase, myelin basic protein, neural cell adhesion molecule, neuron-specific enolase, neurokinin A, neurokinin B, neurotensin, neurotrophin-3, neurotrophin-4/5, neuropeptide Y, proteolipid protein, substance P, thrombomodulin, and protein kinase C gamma.

The term "non-specific marker of cerebral injury" as used in this specification refers to proteins or polypeptides that are elevated in the event of cerebral injury, but may also be elevated due to non-cerebral events. Non-specific markers include, but are not limited to, ApoC-I and ApoC-II, A-type natriuretic peptide, B-type natriuretic peptide, C-type natriuretic peptide adrenomedullin, β-thromboglobulin, C-reactive protein, Cardiac Troponin I and Troponin T, Creatine kinase MB, D-dimer, E-selectin, endothelin-1, endothelin-2, and endothelin-3, A-, F-, and H-Fatty acid binding protein, fibrinopeptide A, hemoglobin $\alpha_2$, chain head activator, insulin-like growth factor-1, MMP-3, plasmin-α-2-antiplasmin complex, platelet factor 4,8-epi PGF sub(2a), PGI2, PGE2, prothrombin fragment 1+2, thrombin-antithrombin III complex, tissue factor, transforming growth factor β, and von Willebrand factor.

The term "diagnosis", as used in this specification refers to predict the type of disease or condition from a set of marker values and/or patient symptoms. This is in contrast to disease prediction, which is to predict the occurrence of disease before it occurs, and the term "prognosis", which is to predict disease progression at a future point in time from one or more indicator value(s) at a previous point in time.

The term "correlating," as used in this specification refers to a process in which a set of examples of clinical inputs from subjects, such as marker levels, and their corresponding outputs, such as whether a subject suffered from a specific type of stroke, are related to each other. This relationship can be determined by comparing such examples to examples from a control and/or disease-free population at a later point in time, and selecting those indicators which can differentiate between the two disease states as a function of time alone or in combination at a certain probability level. The selection process is described herein. The selected markers, each at a certain level range which might be a simple threshold, are said to be correlative or associative with one of the disease states. Said correlated markers can be then be used for disease detection, diagnosis, prognosis and/or treatment outcome. Preferred methods of correlating markers is by performing marker selection by a feature selection algorithm and classification by mapping functions described herein. A preferred probability level is a 3% chance, 5% chance, a 7% chance, a 10% chance, a 15% chance, a 20% chance, a 25% chance, a 30% chance, a 35% chance, a 40% chance, a 45% chance, a 50% chance, a 55% chance, a 60% chance, a 65% chance, a 70% chance, a 75% chance, a 80% chance, a 85% chance, a 90% chance, a 95% chance, and a 100% chance. Each of these values of probability is plus or minus 2% or less. A preferred threshold level for markers of the present invention is about 25 pg/mL, about 50 pg/mL, about 60 pg/mL, about 75 pg/mL, about 100 pg/mL, about 150 pg/mL, about 200 pg/mL, about 300 pg/mL, about 400 pg/mL, about 500 pg/mL, about 600 pg/mL, about 750 pg/mL, about 1000 pg/mL, and about 2500 pg/mL. The term "about" in this context refers to +/−10%.

In yet another of its aspects, the present invention is embodied in methods for determining a treatment regimen for use in a patient diagnosed with stroke. The methods preferably comprise determining a level of one or more diagnostic or prognostic markers as described herein, and using the markers to determine a diagnosis for a patient. For example, a prognosis might include the development or predisposition to delayed neurologic deficits after stroke onset. One or more treatment regimens that improve the patient's prognosis by reducing the increased disposition for an adverse outcome associated with the diagnosis can then be used to treat the patient. Such methods may also be used to screen pharmacological compounds for agents capable of improving the patient's prognosis as above.

In yet another of its aspect, the present invention relates to methods of identifying a patient at risk for hemorrhagic transformation after thrombolytic therapy. Such methods preferably comprise comparing an amount of a marker predictive of a subsequent hemorrhagic transformation, said marker selected from the group consisting of cellular fibronectin (c-Fn), and matrix metalloprotease-9 (MMP-9), in a test sample from a patient diagnosed with an acute ischemic stroke to a predictive level of said marker, wherein said patient is identified as being at risk for hemorrhagic transformation by a level of said marker equal to or greater than said predictive level.

In yet another of its aspects, the present invention is embodied in methods of differentiating ischemic stroke from hemorrhagic stroke using such marker combination panels.

In yet another of its aspects, the present invention Is embodied in kits for determining the diagnosis or prognosis of a patient. These kits preferably comprise devices, software and reagents for measuring one or more marker levels in a patient sample, and instructions for performing the assay. Additionally, the kits contain a computer software program to be run on a computer or other means for converting marker level(s) to a prognosis. Such kits preferably contain sufficient reagents to perform one or more such determinations, and are standardized to run on an instrument used to analyze blood samples, such as Abbott Laboratories' AxSYM®, Roche Diagnostics' Cardiac Reader®, or Dade Behring's Stratus® CS Analyzer.

DETAILED DESCRIPTION OF THE INVENTION

In accordance with the present invention, there are provided methods and apparatus for the identification and use of a panel of markers for the diagnosis of hemorrhage, particularly hemorrhage following tPA therapy.

Fibronectins are adhesive dimeric glycoproteins that promote cell-cell and cell-matrix interactions (see for instance Hynes R O. Fibronectins. *Sci Am.* 1986;254:42-51.). Plasma fibronectin (p-Fn) is primarily produced by hepatocytes, 8 but plasma also contains small quantities of cellular fibronectin (c-Fn), which is mainly synthesized by endothelial cells (see for instance Peters J H, Sporn L A, Ginsberg M H, Wagner D D. Human endothelial cells synthesize, process, and secrete fibronectin molecules bearing an alternatively spliced type II homology (ED1). *Blood.* 1990;75:1801-1808.). Because c-Fn is largely confined to the vascular endothelium, high plasma levels of this molecule might be indicative of endothelial damage. In fact, plasma c-Fn levels have been reported to be increased in patients with vascular injury secondary to vasculitis, sepsis, acute major trauma, and diabetes, (see for instance Peters J H, Maunder R J, Woolf A D, Cochrane G H, Ginsberg M H. Elevated plasma levels of ED1_("cellular") fibronectin in patients with vascular injury. *J Lab Clin Med.* 1989;113:586-597; Kanters S D, Banga J D, Algra A, Frijns R C, Beutler J J, Fijnheer R. Plasma levels of cellular fibronectin in diabetes. *Diabetes Care.* 2000; 24:323-327.). Since HT after cerebral ischemia seems to be the result of the continuous disappearance of basal membrane components (see for instance Hamann G F, Okada Y, del Zoppo G J. Hemorrhagic transformation and microvascular integrity during focal cerebral ischemia/reperfusion. *J Cereb Blood Flow Metab.* 1996; 16:1373-1378.), in the instant invention we show high levels of plasma c-Fn are associated with HT in patients who received thrombolytic treatment with tPA. We also show elevation in patients with acute ischemic stroke for the first time.

Because thrombolytic therapy is the only treatment for ischemic stroke proven to be effective, the investigation of the underlying mechanisms responsible for HT, the most feared complication associated with this therapy, as well as the identification of factors that can improve the benefit/risk ratio of tPA administration is of critical importance. The instant invention demonstrates that plasma c-Fn levels are significantly higher in patients in whom HT develops after tPA administration and teaches that c-Fn levels >3.6 µg/mL can predict the development of HI-2 and PH after tPA administration with a sensitivity and negative predictive value of 100%. Therefore, c-Fn is a useful marker of those patients who are at greatest risk for HT after the administration of thrombolytic treatment.

The loss of microvascular integrity secondary to the continuous disappearance of the antigens of the endothelial components has been reported as being responsible for HT after ischemic injury.3 Among these antigens, c-Fn is especially important because it mediates the interaction between the endothelium and blood cells as well as other blood components.8 Moreover, Fn plays an important role in blood clot formation by mediating the adhesion of platelets to fibrin (see for instance Hynes R O. Fibronectins. *Sci Am.* 1986;254:42-51.), so the disappearance of the c-Fn of the vascular endothelium secondary to ischemia might damage this clotting mechanism, facilitating HT development. Although high c-Fn levels have been previously reported in patients with ischemic stroke, no previous data are available on the association between c-Fn levels in patients with acute ischemic stroke.

The increase of vascular permeability and subsequent extravasation of serum components leading to HT after tPA administration may be the result of several mechanisms including the activation of MMPs, which is secondary to ischemia, and the administration of tPA (see for instance Sumii T, Lo E H. Involvement of matrix metalloproteinase in thrombolysis-associated hemorrhagic transformation after embolic focal ischemia in rats. *Stroke.* 2002;33:831-836.). The instant invention also details the significant association between MMP-9 levels and HT in patients who received tPA and in a nonselected series of ischemic stroke patients. However, the fact that c-Fn is almost exclusively located at the endothelium suggests that this molecule could be a more specific marker of a high risk for HT. This hypothesis is supported by our finding that c- Fn levels, but not MMP-9 levels, remained independently associated with HT in the logistic regression analysis. Moreover, the predictive capacity of plasma c-Fn levels for the development of HI-2 and PH was higher than the predictive capacity of MMP-9 levels. However, although the difference did not reach statistical significance, probably because of the small sample size, there was a clear trend for the levels of c-Fn to be higher in patients with symptomatic HT, whereas MMP levels were similar in symptomatic and asymptomatic bleedings. Because neurological deterioration usually occurs in patients with more severe HT, c-Fn levels probably reflect not only endothelial damage but also the degree of endothelial damage. In agreement with this hypothesis, we have observed a positive correlation between c-Fn levels and hypodensity volume at 24 to 36 hours of evolution of the ischemia, which probably reflects the relationship between endothelial and brain injuries. This positive correlation could lead us to argue that c-Fn levels are just an epiphenomenon of the extent of brain damage. However, we find that it is the plasma c-Fn concentrations rather that infarct volume that independently predicted HT.

The basal lumina disruption and the subsequent release of c-Fn after brain ischemic injury into the plasma, as well as accelerated Fn synthesis by endothelial cells and other cells such as polymorphonuclear leukocytes arriving at the ischemic tissue as part of the ischemic inflammatory cascade, could be among the participating mechanisms. Interleukins and transforming growth factor, whose expression is increased as a result of ischemia (see for instance Feuerstein G Z, Wang X, Barone F C. Inflammatory mediators and brain injury: the role of cytokines and chemokines in stroke and CNS diseases. In: Ginsberg M D, Bogousslavsky J, eds. *Cerebrovascular Disease:Pathophysiology, Diagnosis, and Management.* Boston, Mass.: Blackwell Science; 1998:507-531.), have been shown to stimulate Fn synthesis (see for instance Roberts C J, Birkenmeier T M, McQuillar J J, Akiyama S K, Yamada S S, Chen WT, Yamada KM, McDonald JA. Transforming growth factor beta stimulates the expression of fibronectin and of both subunits of the human fibronectin receptor by cultured human lung fibroblast. *J. Biol. Chem.* 1988;263:4586-4592.). Increased c-Fn synthesis could be an attempt to decrease endothelial destruction by MMPs, which might explain the positive correlation between c-Fn and MMP-9 in the instant invention.

Recently, many researchers have investigated the possibility of blood- borne markers of stroke and its subtypes. This approach is well established in the clinical setting of suspected myocardial ischemia. In acute coronary syndromes, the myocardial isoform of creatinine phosphokinase and troponin play an important role both in treatment decisions and clinical research. Similarly, B-type natriuretic peptide has become a routine part of the assessment of patients with congestive heart failure and dyspnea. However, the ischemic cascade of glial activation and ischemic neuronal injury in stroke is far more complex than myocardial ischemia and less amenable to the use of a single biochemical marker. Indeed, the authors of the instant invention know of no individual biochemical marker has been demonstrated to possess the requisite sensitivity and specificity to allow it to function independently as a clinically useful diagnostic marker.

Thus a panel of markers was envisioned to overcome this deficiency in 1998 or earlier for detecting stroke (see for instance Misz M, Olah L, Kappelmayer J, Blasko G, Udvardy M, Fekete I, Csepany T, Ajzner E, Csiba L. Hemostatic abnormalities in ischemic stroke, Orv Hetil. 1998 Oct. 18;139(42): 2503-7; Tarkowski E, Rosengren L, Blomstrand C, Jensen C, Ekholm S, Tarkowski A. Intrathecal expression of proteins regulating apoptosis in acute stroke. Stroke. 1999 February; 30(2):321-7; Stevens H, Jakobs C, de Jager A E, Cunningham R T, Korf J. Neurone-specific enolase and N-acetyl-aspartate as potential peripheral markers of ischaemic stroke. Eur J Clin Invest. 1999 January; 29(1):6-11.) or its sub-types (see for instance Soderberg S, Ahren B, Stegmayr B, Johnson O, Wiklund P G, Weinehall L, Halimans G, Olsson T. Leptin is a risk marker for first-ever hemorrhagic stroke in a population-based cohort. Stroke. 1999 February; 30(2):328-37).

In many studies since this time, many blood-borne proteomic markers have been shown to be associated with stroke and its sub-types. For example, acute stroke has been associated with serum elevations of numerous inflammatory and anti-inflammatory mediators such as interleukin 6 (IL-6) and matrix metalloproteinase-9 (MMP-9) (see for instance Kim J S, Yoon S S, Kim Y H, Ryu J S. Serial measurement of interleukin-6, transforming growth factor-beta, and S-100 protein in patients with acute stroke. *Stroke.* 1996;27:1553-1557.; Dziedzic T, Bartus S, Klimkowicz A, Motyl M, Slowik A, Szczudlik A. Intracerebral hemorrhage triggers interleukin-6 and interleukin-10 release in blood. *Stroke.* 2002;33: 2334-2335.; Beamer N B, Coull B M, Clark W M, Hazel J S, Silberger J R. Interleukin-6 and interleukin-1 receptor antagonist in acute stroke. *Ann Neurol.* 1995; 37:800-805.; Montaner J, Alvarez-Sabin J, Molina C, et al. Matrix metalloproteinase expression after human cardioembolic stroke: temporal profile and relation to neurological impairment. *Stroke.* 2001;32:1759-1766.; Perini F, Morra M, Alecci M, Galloni E, Marchi M, Toso V. Temporal profile of serum anti-inflammatory and pro-inflammatory interleukins in acute ischemic stroke patients. *Neurol Sci.* 2001;22:289-296.; Vila N, Castillo J, Davalos A, Chamorro A. Proinflammatory cytokines and early neurological worsening in ischemic stroke. *Stroke.* 2000;31: 2325-2329), markers of impaired hemostasis and thrombosis (see for instance Fon E A, Mackey A, Cote R, et al. Hemostatic markers in acute transient ischemic attacks. *Stroke.* 1994;25:282-286.; Takano K, Yamaguchi T, Uchida K. Markers of a hypercoagulable state following acute ischemic stroke. *Stroke.* 1992;23:194-198.), and markers of glial activation such as S100b (see for instance Buttner T, Weyers S, Postert T, Sprengelmeyer R, Kuhn W. S-100 protein: serum marker of focal brain damage after ischemic territorial MCA infarction. *Stroke.* 1997;28:1961-1965.; Martens P, Raabe A, Johnsson P. Serum S-100 and neuron-specific enolase for prediction of regaining consciousness after global cerebral ischemia. *Stroke.* 1998;29: 2363-2366.). Several of these mediators, including IL-6, have been shown to be elevated within hours after ischemia and correlate with infarct volume (see for instance Fassbender K, Rossol S, Kammer T, et al. Proinflammatory cytokines in serum of patients with acute cerebral ischemia: kinetics of secretion and relation to the extent of brain damage and outcome of disease. *J Neurol Sci.* 1994;122:135-139.; Tarkowski E, Rosengren L, Blomstrand C, et al. Early intrathecal production of interleukin-6 predicts the size of brain lesion in stroke. *Stroke.* 1995;26: 1393-1398).

Other authors have looked at the differentiation between TIA and stroke (see for instance Dambinova S A, Khounteev G A, Skoromets A A. Multiple panel of biomarkers for TIA/stroke evaluation. *Stroke.* 2002;33:1181-1182.) or type of hemorrhage (see for instance McGirt M J, Lynch J R, Blessing R, Warner D S, Friedman A H, Laskowitz D T. Serum von Willebrand factor, matrix metalloproteinase-9, and vascular endothelial growth factor levels predict the onset of cerebral vasospasm after aneurysmal subarachnoid hemorrhage. *Neurosurgery.* 2002;51:1128-1134).

To this date, most of these studies have been in small number of patients and while have individual markers in common, the panels proposed in each have not been replicated. This is due to the fact that many reported panels merely linearly add the effects of multiple markers, or perform simple logistic regression to get correlative effects of a panel. One such example of the current state of the art is that of Reynolds et al. (Mark A. Reynolds, Howard J. Kirchick, Jeffrey R. Dahlen, Joseph M. Anderberg, Paul H. McPherson, Kevin K. Nakamura, Daniel T. Laskowitz, Gunars E. Valkirs, and Kenneth F. Buechler, Early biomarkers of stroke, *Clinical Chemistry* 49:10 1733-1739, 2003). In this paper, a five marker panel consisting of S-100β, B-type neurotrophic growth factor, von Willebrand factor, matrix metalloproteinase-9, and monocyte chemotactic protein-1 was disclosed as suggested blood-borne panel to diagnosis acute ischemic stroke. In this analysis, univariate analysis was used to select an initial pool of candidate markers, and then multivariate analysis was used to achieve the final panel. However, as shown in the instant invention, this methodology is flawed. The result of this paper was tested on data used to train such, a typical mistake which usually leads to an irreproducible result.

Another example of the state of the art is U.S. Patent application 20040121343 and/or U.S. patent Ser. No. 10/225,082. In these application, a variety of markers for the diagnosis of stroke are envisioned, the mere presence or absence of such markers in the blood being indicative of disease. This methodology is fatally flawed, however, since it does not indicate how to relate the collective nonlinear effects of all markers to the outcome of interest, i.e. specify an algorithm to select among such markers and another to classify such markers as related to outcome. Instead, the application anticipates using the thresholded values of such markers as an indicator, giving a simple binary response of each as a value. As such markers are all treated as independent variables, there is no interaction between them, another fatal flaw.

Most existing statistical and computational methods for biomarker feature selection, such as U.S. Patent applications 20040126767 and/or U.S. patent application 20040219509, have focused on differential expression of markers between diseased and control data sets. This metric is tested by simple calculation of fold changes, by t-test, and/or F test. These are based on variations of linear discriminant analysis (i.e., calculating some or the entire covariance matrix between features).

However, the majority of these data analysis methods are not effective for biomarker identification and disease diagnosis for the following reasons. First, although the calculation of fold changes or t-test and F-test can identify highly differentially expressed biomarkers, the classification accuracy of identified biomarkers by these methods, is, in general, not very high. This is because linear transforms typically extract information from only the second-order correlations in the data (the covariance matrix) and ignore higher-order correlations in the data. We have shown that proteomic datasets are inherently non-symmetric (unpublished data). For such cases, nonlinear transforms are necessary. Second, most scoring methods do not use classification accuracy to measure a biomarker's ability to discriminate between classes. Therefore, biomarkers that are ranked according to these scores may not achieve the highest classification accuracy among biomarkers in the experiments. Even if some scoring methods, which are based on classification methods, are able to identify biomarkers with high classification accuracy among all biomarkers in the experiments, the classification accuracy of a single marker cannot achieve the required accuracy in clinical diagnosis. Third, a simple combination of highly ranked markers according to their scores or discrimination ability is usually not be efficient for classification, as shown in the instant invention. If there is high mutual correlation between markers, then complexity increases without much gain.

Accordingly, the instant invention provides a methodology that can be used for biomarker feature selection and classification, and is applied in the instant application to detection of stroke and its subtypes.

Exemplary Biomarkers related to detection of hemorrhage.

A comprehensive methodology for identification of one or more markers for the prognosis, diagnosis, and detection of disease has been described previously. Suitable methods for identifying such diagnostic, prognostic, or disease-detecting markers are described in detail in U.S. Pat. No. 6,658,396, NEURAL NETWORK DRUG DOSAGE ESTIMATION, U.S. patent application Ser. No. 09/611,220, entitled NEURAL-NETWORK-BASED INDENTIFICATION, AND APPLICATION, OF GENOMIC INFORMATION PRACTICALLY RELEVANT TO DIVERSE BIOLOGICAL AND SOCIOLOGICAL PROBLEMS, filed Jul. 6, 2000, and U.S. provisional patent application Ser. No. 60/505,606, entitled DIAGNOSTIC MARKERS OF CARDIOVASCULAR ILLNESS AND METHODS OF USE THEREOF, filed Sep. 23, 2003, each of which patents and partent applicatons is hereby incorporated by reference in its entirety, including all tables, figures, and claims. Briefly, our method of predicting relevant markers given an individual's test sample is an automated technique of constructing an optimal mapping between a given set of input marker data and a given clinical variable of interest. We illustrate this method further in the following section called "Methodology of Marker Selection, Analysis, and Classification"

We first obtain patient test samples of some bodily fluid, such as blood, cerebrospinal fluid, or urine from two or more groups of patients. Preferred fluid is blood. The patients are those exhibiting symptoms of a disease event, say stroke, which is determined at a later time, and those not exhibiting the same disease event, which are viewed as controls, though these patients might have another disease event distinct from the first. Samples from these patients are taken at various time periods after the event has occurred, and assayed for various markers as described within. Clinical information, such as sex, age, time from onset of symptoms to treatment, NIHSS score, biochemistry and vital signs at admission, and neuroimaging findings are collected at various time periods. Preferred time periods for the instant invention include 0, 3 hours, 6 hours, 9 hours, 12 hours, 15 hours, 18 hours, 24 hours, 36 hours, 48 hours, 72 hours, 1 week, 2 weeks, 3 weeks, 4 weeks, 3 months and 6 months. Time is measured either from onset of symptoms or admission into a clinical setting where the patient receives care. This marker and clinical information form a set of examples of clinical inputs and their corresponding outputs, the outputs being the clinical outcome of interest, for instance stroke and stroke subtype occurrence or non-occurrence, hemorrhagic transformation, or stroke mimic subtype. These quantities are as described in the Introduction.

We then use an algorithm to select the most relevant clinical inputs that correspond to the outcome for each time period. This process is also known as feature selection. In this process, the minimum number of relevant clinical inputs that are needed to fully differentiate and/or predict disease prognosis, diagnosis, or detection with the highest sensitivity and specificity are selected for each time period. The feature selection is done with an algorithm that selects markers that differentiate between patient disease groups, say hemorrhagic versus ischemic. The relevant clinical input combinations might change at different time periods, and might be different for different clinical outcomes of interest.

We then train a classifier to map the selected relevant clinical inputs to the outputs. A classifier assigns relative weightings to individual marker values. We note that the construct of a classifier is not crucial to our method. Any mapping procedure between inputs and outputs that produces a measure of goodness of fit, for example, maximizing the area under the receiver operator curve of sensitivity versus 1-specificity, for the training data and maximizes it with a standard optimization routine on a series of validation sets would also suffice.

Once the classifer is trained, it is ready for use by a clinician. The clinician enters the same classifer inputs used during training of the network by assaying the selected markers and collecting relevant clinical information for a new patient, and the trained classifier outputs a maximum likelihood estimator for the value of the output given the inputs for the current patient. The clinician or patient can then act on this value. We note that a straightforward extension of our technique could produce an optimum range of output values given the patient's inputs as well as specific threshold values for inputs.

One versed in the ordinary state of the art knows that many other markers in the literature once measured from the blood in a diseased and healthy patient, selected through use of an feature selection algorithm might be diagnostic of cardiovascular illness if measured in combination with others and evaluated together with a nonlinear classification algorithm. We describe some of these other markers, previously considered for diagnosis or prognosis of cardiovascular illness and thus not novel in themselves. This list is meant to serve as illustrative and not meant to be exhaustive. Selected marker descriptions in the following list are similar to U.S. patent application 20040126767 and/or U.S. patent application 20040219509, both of which are noted as prior art. However, the instant invention goes beyond what is taught or anticipated in these applications, providing a rigorous methodology of discovering which representative markers are best suited to building a predictive model for determining a clinical outcome and building a model for interpolating between such markers to determine clinical outcome, while the methodology described in U.S. Patent application 20040126767 and/or U.S. patent application 20040219509 rely on simple linear relationships between markers and linear optimization techniques to find them. As also previously discussed in the instant invention, neither the general markers used, the idea of combinations of such markers, nor techniques used to analyze them are novel.

Blood Pressure Regulatory Markers

Natriuretic Peptides

Adrenomedullin is a potent endogenous vasodilating and natriuretic peptide that is similar in structure to calcitonin gene-related peptide (CGRP). The gene involved in the synthesis of adrenomedullin has been localized to a single locus on chromosome 11, with specific sites on the genome to regulate transcription. Adrenomedullin is normally found in human plasma and in other organs. It is thought that one of the clearance sites for this peptide is in the pulmonary circulation. Endothelial cells are assumed to be one of the major sources of plasma adrenomedullin. Adrenomedullin is an important factor in regulating local and systemic vascular tone, by its activity as an autocrine/paracrine and circulating hormone. Depending on the site of action, adrenomedullin seems to bind to a CGRP receptor and send signals by either cyclic adenosine monophosphate or nitric oxide. From the results of experiments in animals, it has become clear that adrenomedullin's effects are species-specific. However, what is commonly seen with adrenomedullin is peripheral vasodilatation, a positive inotropic action, increased cardiac output, and increased stroke volume. In addition, adrenomedullin has actions in the brain, lungs, and kidneys to regulate regional hemodynamics.

Atrial natriuretic peptide (ANP) has an important physiological role in the maintenance of arterial blood pressure and volume via its vasodilating and diuretic effects. It is a 28 amino acid peptide (ANP99-126), and has an N-terminal form (ANP1-99) and Its guanylyl cyclase-A (GC-A) receptor is also highly expressed in vascular endothelium. ANP has been implicated as a causative marker of stroke (see for instance Rubattu S, Ridker P M, Stampfer M, Hennekens C H, Volpe M, Lindpaintner K. The gene encoding atrial natriuretic peptide and the risk of human stroke. *Circulation*. 1999; 100: 1722-1726) N- terminal pro-ANP has been shown as prognostic indicator for heart failure as well as other cardiac events (see for instance Wang et al. Plasma Natriuretic Peptide Levels and the Risk of Cardiovascular Events and Death, N Engl J Med 2004;350:655-63.)

B-type natriuretic peptide (BNP), also called brain-type natriuretic peptide is a 32 amino acid, 4 kDa peptide that is involved in the natriuresis system to regulate blood pressure and fluid balance. See for instance Bonow, R. O., Circulation 93:1946-1950 (1996). The precursor to BNP is synthesized as a 108-amino acid molecule, referred to as "pre pro BNP," that is proteolytically processed into a 76-amino acid N-terminal peptide (amino acids 1-76), referred to as "NT pro BNP" and the 32-amino acid mature hormone, referred to as BNP or BNP 32 (amino acids 77-108). It has been suggested that each of these species NT pro-BNP, BNP-32, and the pre pro BNP—can circulate in human plasma. See for instance Tateyama et al., Biochem. Biophys. Res. Commun. 185: 760-7 (1992); Hunt et al., Biochem. Biophys. Res. Commun. 214: 1175-83 (1995). The 2 forms, pre pro BNP and NT pro BNP, and peptides which are derived from BNP, pre pro BNP and NT pro BNP and which are present in the blood as a result of proteolyses of BNP, NT pro BNP and pre pro BNP, are collectively described as markers related to or associated with BNP.

The term "BNP" as used herein refers to the mature 32-amino acid BNP molecule itself. As the skilled artisan will recognize, however, because of its relationship to BNP, the concentration of NT pro-BNP molecule can also provide diagnostic or prognostic information in patients. The phrase "marker related to BNP or BNP related peptide" refers to any polypeptide that originates from the pre pro-BNP molecule, other than the 32-amino acid BNP molecule itself. Proteolytic degradation of BNP and of peptides related to BNP have also been described in the literature and these proteolytic fragments are also encompassed it the term "BNP related peptides."

BNP and BNP-related peptides are predominantly found in the secretory granules of the cardiac ventricles, and are released from the heart in response to both ventricular volume expansion and pressure overload. See for instance Wilkins, M. et al., Lancet 349: 1307-10 (1997). Elevations of BNP are associated with raised atrial and pulmonary wedge pressures, reduced ventricular systolic and diastolic function, left ventricular hypertrophy, and myocardial infarction. See for instance Sagnella, G. A., Clinical Science 95: 519-29 (1998). Furthermore, there are numerous reports of elevated BNP concentration associated with congestive heart failure and renal failure.

C-type natriuretic peptide (CNP) is a 22-amino acid peptide that is the primary active natriuretic peptide in the human brain; CNP is also considered to be an endothelium-derived relaxant factor, which acts in the same way as nitric oxide (NO) (Davidson et al., Circulation 93:1155-9, 1996). CNP is structurally related to Atrial natriuretic peptide (ANP) and B-type natriuretic peptide (BNP); however, while ANP and BNP are synthesized predominantly in the myocardium, CNP is synthesized in the vascular endothelium as a precursor (pro-CNP) (Prickett et al., Biochem. Biophys. Res. Commun. 286:513-7, 2001). CNP is thought to possess vasodilator effects on both arteries and veins and has been reported to act mainly on the vein by increasing the intracellular cGMP concentration in vascular smooth muscle cell Urotensin II (U-II) is a peptide having the sequence Ala-Gly-Thr-Ala-Asp-Cys-Phe-Trp-Lys-Tyr-Cys-Val, with a disulfide bridge between Cys6 and Cys 11. Human urotensin 2 is synthesized in a prepro form. Urotensin-II potently contracts some large isolated blood vessels and cardiac tissue. However, the maximum effects on human blood vessels and heart are relatively small. U-II dilates human resistance arteries. It markedly decreased myocardial function and increased vascular resistance in cynomolgus monkeys, but the major effects of U-II have not been observed in healthy humans. A major role for U-II in human cardiovascular disease has not been clearly established despite studies in patients with coronary artery disease, heart failure, essential hypertension and diabetes.

Arginine vasopressin (AVP) is a potent endogenous vasopressor hormone of the neurohypophysis. It is involved in the renal system's processing of water. AVP does this by elevating water permeability in the renal collecting duct. AVP can also be released during hemhorrage, resulting in a decrease in atrial pressure. This occurance is called Hypovolemia, in which AVP release is stimulated by a change in extracellular osmolarity. Angiotensin II receptors in the hypothalamus can release AVP as well in response to changes in angiotensin II levels.

Calcitonin gene related peptide (CGRP) is a 37-amino acid neuropeptide, primarily released from sensory nerves, that is a potent dilator of human brain arteries, and they have been implicated in the neurogenic inflammation underlying migraine headache and in the evolution of stroke, respectively. The polypeptide is a product of the calcitonin gene derived by alternative splicing of the precursor mRNA. The calcitonin gene (CALC-I) primary RNA transcript is processed into different mRNA segments by inclusion or exclusion of different exons as part of the primary transcript. Both CGRP and ADM can affect human brain vessels through a CGRP1 receptor (see for instance Moreno et al. Functional calcitonin gene-related peptide type 1 and adrenomedullin receptors in human trigeminal ganglia, brain vessels, and cerebromicrovascular or astroglial cells in culture. J Cereb Blood Flow Metab. 1999 November; 19(11):1270-8) The peptide can act on a family of CGRP receptors that consist of calcitonin receptor-like receptor (CL) linked to one of three receptor activity-modifying proteins (RAMPs) that are essential for functional activity. The association of CL with RAMP1 produces a CGRP receptor, with RAMP2 an adrenomedullin (AM) receptor and with RAMP3 a CGRP/AM receptor.

Angiotensin II (Ang II) The angiotensin-converting enzyme/angiotensin II (ACE/Ang II) system plays an important role in the formation of atherosclerotic lesions. Normally, Ang II is converted from Ang I by ACE which is expressed in endothelial cells (EC) of normal vessels. It is thought to play an important role in the induction of intimal hyperplasia and the proliferation and migration of vascular smooth muscle cells (SMC). Thus, the ACE/Ang II system induces the proliferation of EC and SMC and may contribute to the formation of a thick fibrous cap. Unstable plaques have a thin and fragile fibrous cap, and the role of the ACE/Ang II system in their formation remains to be exactly established. Atherosclerotic plaques typically consist of a lipid-rich core in the central portion of the thickened intima that is bounded at its luminal aspect by a fibrous cap whose integrity determines the stability of the plaque. In stable plaques, a thick fibrous cap covers the entire lipid core. Rupture-prone (i.e., unstable) plaques, on the other hand, tend to have a thin, fragile cap, especially at the shoulder lesion, and contribute to ischemic events (see for instance P. D. Richardson, M. J. Davies and G. V. Born, Influence of plaque configuration and stress distribution on fissuring of coronary atherosclerotic plaques. *Lancet* 2(1989), pp. 941-944. and H. M. Loree, R. D. Kamm, R. G. Stringfellow et al., Effects of fibrous cap thickness on peak circumferential stress in model atherosclerotic vessels. *Circ Res* 71 (1992), pp. 850-858).

Morioka et al (Morioka et al, Contribution of angiotensin-converting enzyme and angiotensin II to ischemic stroke: Their role in the formation of stable and unstable carotid atherosclerotic plaques) showed that Ang II distribution coincided with ACE distribution. In human tissues, Ang II is produced not only by ACE but also by chymase, a chymotrypsin-like serine protease. However, our data suggest that ACE is a major enzyme that produces Ang II in atherosclerotic lesions. In both stable and unstable plaques, EC and ACE were frequently co-localized. Furthermore, in stable plaques, macrophages and ACE were frequently co-localized; this was not the case in shoulder lesions from unstable plaques. However, even in unstable plaques, except for the shoulder lesion, ACE was co-localized with macrophages in the fibrous cap (data not shown). These observations suggest that in stable plaques, ACE was expressed in areas of EC- and macrophage accumulation. In the shoulder lesion of unstable plaques, ACE expression was less pronounced or faint and there was moderate or little proliferation of SMC and EC.

In the early stage of atherosclerotic lesion formation, EC and macrophages may secrete biologic factors such as ACE/Ang II and induce intimal thickening and the formation of a lipid core. After maturation of the lesion, macrophages may lose the ability to secrete ACE/Ang II that, in turn, may decrease the proliferation of EC and SMC and result in thinning of the fibrous cap. However, the macrophages retain the ability to accumulate lipids, rendering stable plaques unstable. This putative functional change in the macrophage population may be restricted to the shoulder lesion. The that loss of ACE/Ang II expression may induce the final step in unstable plaque formation while the high expression of ACE/Ang II may induce intimal hyperplasia resulting in severe stenosis and ischemic stroke because of disturbances in the hemodynamic mechanism.

Endothelin-1 (ET-1) is a 21 aminoacid peptide with potent vasoconstrictor properties. It is synthesised and released by endothelial cells in both the peripheral and cerebral vasculature and is also localised within neurones in discrete brain areas where it may contribute to the central regulation of blood pressure. It has been shown that intracisternal ET-1 in conscious rats induces a marked pressor response that is associated with an intense widespread reduction in cerebral blood flow. Subsequent studies with local application of ET-1 to the middle cerebral artery (MCA) revealed a dose dependent reversible vasoconstriction of the artery that resulted in profound reductions in local cerebral blood flow and the development of cerebral infarction. Thus abluminal application of ET-1 to the MCA offers a simple model of reversible focal cerebral ischaemia in the rat that complements the existing models of permanent MCA occlusion. Many authors have shown that ischemic stroke is associated with elevated plasma ET-1 levels (For instance see Ziv I et al, Increased plasma endothelin-1 in acute ischemic stroke. Stroke. 1992 July; 23(7):1014-6.). Elevation of ET-1 in plasma has been reported 1 to 3 days after ischemic stroke (Lampl et al. Endothelin in cerebrospinal fluid and plasma of patients in the early stage of ischemic stroke. Stroke. 1997 October; 28(10):1951-5). Related to ET-1 is endothelin-2 and endothelin-3, which are also 21 amino acid residues in length, and are produced by hydrolysis of big endothelin-2 and big endothelin-3, respectively (Yap et al., Br. J. Pharmacol. 129:170-6, 2000; Lee et al., Blood 94:1440-50,1999).

Hemostatic Markers

D-Dimer

D-dimer is a fibrin degradation product with an approximate molecular mass of 200 kDa. D-dimer marks plasmin activity and fibrinolysis, including stroke. Normal plasma levels of D-Dimer are <150 ng/ml (750 pM). D-dimer levels in ischemic stroke have been reported as being high in all phases [N. Ono, T. Koyama, A. Suchiro, K. Oku, K. Fujikake and E. Kakishita, Clinical significance of new coagulation and fibrinolytic markers in ischemic stroke patients. *Stroke* 22 (1991), pp. 1369-1373. and M. Yamazaki, S. Uchiyama and S. Maruyama, Alterations of haemostatic markers in various subtypes and phases of stroke. *Blood Coagulation and Fibrinolysis* 4 (1993), pp. 707-712], significantly high in subacute and chronic phases [H. Tohgi, M. Kawashima, K. Tamura and H. Suzuki, Coagulation-fibrinolysis abnormalities in acute and chronic phases of cerebral thrombosis and embolism. *Stroke* 21 (1990), pp. 1663-1667.], and high in acute phase but low in chronic phase [M. Fisher and R. Francis, Altered coagulation in cerebral ischemia. Platelet, thrombin and plasmin activity. *Arch Neurol* 47 (1990), pp. 1075-1079].

Stroke subtype is not the only factor that might influence the concentration of hemostatic markers. Coagulation and fibrinolysis may also be altered by drugs and associated diseases such as angina, atrial fibrillation, and diabetes mellitus.

Thrombin is a multifunctional serine protease that is involved not only in mediating the cleavage of fibrinogen to fibrin in the coagulation cascade but also in activating a variety of cell types, including platelets and endothelial cells. Thrombin signaling in the endothelium might result in a multitude of phenotypic changes, including alterations in cell shape, permeability, vasomotor tone, leukocyte trafficking, migration, DNA synthesis, angiogenesis, and hemostasis. Thrombin signaling in the endothelium is mediated by a family of 7-transmembrane G protein-coupled receptors, termed protease-activated receptors (PARs). Currently, 4 members of the PAR family have been identified (PAR-1 through PAR-4;). PAR-1 and PAR-3 are thrombin receptors. Thrombin activation of PAR-4 requires PAR-3 as a thrombin-binding cofactor. Human umbilical vein endothelial cells (HUVECs) have been reported to express PAR-1, PAR-2, and, to a lesser extent, PAR-3, but not PAR-4. One study provided evidence for the existence of functional PAR-4 receptors (as well as those for PAR-1 and PAR-2 but not PAR-3) in the endothelium of human coronary artery ring segments. Of the various PAR family members, PAR-1 is the predominant thrombin receptor in endothelial cells. Thrombin activates PAR-1 by binding to a unique site in the extracellular domain of the receptor, resulting in cleavage between Arg41 and Ser42 and consequent exposure of a new N-terminus. The unmasked tethered ligand (SFLLRN) interacts with the extracellular loop 2 of the receptor (amino acids 248 to 268), resulting in receptor activation. Once activated, PAR-1 is coupled to a family of heterotrimeric G proteins, consisting of an-subunit and a β-dimer. The G proteins are in turn linked to a number of signal intermediates that include, but are not limited to, mitogen-activated protein kinase (MAPK), protein kinase C (PKC), phosphatidyl inositol 3-kinase (PI3K), and Akt. Thrombin signaling might result in posttranscriptional changes, including calcium influx, cytoskeletal reorganization, and release of soluble mediators, growth factors, and matrix metalloproteinases. In addition, thrombin signaling results in changes in downstream gene transcription. For example, under in vitro conditions, thrombin has been shown to increase the expression of genes that are involved in cell proliferation, inflammation, leukocyte adhesion, vasomotor tone, and hemostasis.

Thrombin-antithrombin III complex (TAT) regulates thrombin, factor XIa, factor XIIa, and factor IXa proteolytic activity. TAT is formed immediately following thrombin activation in the presence of heparin, which is the limiting factor in this interaction. Heparin enhances the inhibitory activity of ATIII by 2-3 orders of magnitude, resulting in almost sudden inactivation of proteinases inhibited by ATIII. ATIII inhibits its target proteinases through the formation of a covalent 1:1 stoichiometric complex. The normal plasma concentration of the approximately 100 kDa TAT is <5 ng/ml (50 pM). TAT concentration is elevated in patients with acute myocardial infarction and unstable angina, especially during spontaneous ischemic episodes (Biasucci, L. M. et al., Am. J. Cardiol. 77:85-87, 1996; Kienast, J. et al., Thromb. Haemost. 70:550-553, 1993). Elevation of the plasma TAT concentration is also seen in any condition associated with coagulation activation, including stroke, surgery, trauma, disseminated intravascular coagulation, and thrombotic thrombocytopenic purpura. TAT has a half-life of approximately 5 minutes in the bloodstream (Biasucci, L. M. et al., Am. J. Cardiol. 77:85-87, 1996). TAT concentration is elevated in, exhibits a sharp drop after 15 minutes, and returns to baseline less than 1 hour following coagulation activation. The plasma concentration of TAT can approach 50 ng/ml in ACS (Biasucci, L. M. et al., Circulation 93:2121-2127, 1996).

Markers Related To Myocardial Necrosis

Cardiac Troponin

Cardiac troponin I or troponin T (cTnI and cTnT) are the preferred markers of myocardial necrosis because they allow a more sensitive detection of myocardial damage and are more specific for the myocardial tissue than the traditional "cardiac enzymes" such as creatine kinase (CK) or its isoenzyme MB (CK-MB). The troponin complex is formed by three distinct structural proteins (troponin 1, C and T) and is located on the thin filament of the contractile apparatus in both skeletal and cardiac muscle tissue regulating the calcium dependent interaction of myosin and actin. The cardiac isoforms of troponin T and I are exclusively expressed in cardiac myocytes, and their detection in the blood is specific for myocardial damage [J. I. Adams, D. Abendschein and A. Jaffe, Biochemical markers of myocardial injury: is MB the choice for the 1990's?. *Circulation* 88 (1993), pp. 750-763.]. The normal plasma concentration of cTnI is <0.1 ng/ml (4 pM). After myocardial infarction, the troponin rise in peripheral blood is seen after 3-4 h with persistent elevation for up to 2 weeks. The high proportional rise of troponins, reflecting the low plasma concentrations in healthy persons, allows the detection of myocardial damage in about one-third of patients with UA even in the absence of minor CK-MB elevations [M. Galvani, F. Ottani, D. Ferrini et al., Prognostic influence of elevated values of cardiac troponin I in patients with unstable angina. *Circulation* 95 (1997), pp. 2053-2059].

Myelo-peroxidase (MPO) is a mediator enzyme secreted by a variety of inflammatory cells, including activated neutrophils and monocytes/macrophages, such as those found in atherosclerotic plaque (Blake G J, Ridker P M. C-reactive protein and other inflammatory risk markers in acute coronary syndromes. J Am Coll Cardiol 2003;41:37S-42S.). It possesses pro-inflammatory properties and may contribute directly to tissue injury (Eiserich J P, Baldus S, Brennan M L et al. Myeloperoxidase, a leukocyte-derived vascular NO oxidase. Science 2002;296:2391-4.). Two recent experiments evaluated MPO as a predictor of cardiac risk in populations with different prevalences of ACS (Brennan M L, Penn M S, Van Lente F et al. Prognostic value of myeloperoxidase in patients with chest pain. N Engl J Med 2003;349:1595-604.; and Baldus S, Heeschen C, Meinertz T et al. Myeloperoxidase serum levels predict risk in patients with acute coronary syndromes. Circulation 2003;108:1440-5.). In both studies, a single measurement of plasma MPO at hospital admission predicted the risk of major adverse cardiac events in the ensuing 30-day and six-month periods. Even in the absence of myocardial necrosis, i.e., consistently negative cardiac troponin, baseline measurements of MPO significantly enhanced the identification of patients at risk. Also, MPO predicted adverse outcome independently of sCD40L; in ACS patients with undetectable troponin concentrations and sCD40L concentrations below the established diagnostic threshold value, high MPO concentrations remained predictive for increased cardiac risk. This may imply that neutrophil activation represents an adjunct pathophysiological event in ACS that is distinctly different from platelet activation.

Annexin V, (also known as anchorin CII, calcium binding protein 33, calphobindin I, endonexin II, lipocortin V, placental anticoagulant protein I, thromboplastin inhibitor, or vascular anticoagulant-alpha), is a 33 kDa calcium-binding protein that is high-affinity phospholipid-binding protein, binds to phosphatidylserine and neutralizes the phosphatidylserine-related procoagulant activity. Annexin V regulates tissue factor and is released into the bloodstream shortly after a patient experiences acute myocardial infarction. Annexin V is widely distributed in various tissues in the body and thus this marker may be elevated in a variety of tissue injuries.

Studies of MLC-1, a 27 kDa protein, as a biochemical marker of myocyte injury in patients with heart failure are few. Hansen and colleagues reported that circulating MLC-1 was elevated in some patients in NYHA functional class III and IV, and this increase was associated with a poor prognosis in a clinical trial of flosequinin (Hansen M et al., Relation of circulating cardiac myosin light chain 1 isoform in stable severe congestive heart failure to survival and treatment with flosequinan. *Am J Cardiol* 2002; 90:969-73.).

Enolase (2-phospho-D glycerate hydrolyase or phosphopyruvate hydratase, EC 4.2.1.11) is a glycolytic enzyme that converts 2-phospho-D glycerate to phosphoenolpyruvate. It is a protein which is functionally active as a heterodimer assembled from a combination of three subunits: alpha, beta and gamma. The gg and ag isoenzymes are referred to as neuron-specific enolase (NSE) because it was initially thought that these isoenzymes were exclusively found in neurons (Rider C C & Taylor C B (1975). Evidence for a new form of enolase in rat brain. *Biochemical and Biophysical Research Communications,* 66: 814-820.). However, it was subsequently shown that neuroendocrine cells and several non-neuronal and non-neuroendocrine cells also contained NSE. In contrast to neurons which express the gg isoenzyme, non-neuronal cells contain predominantly the ag isoenzyme (Marangos P J & Schmechel D E (1987). Neuron specific enolase, a clinically useful marker for neurons and neuroendocrine cells. *Annual Review of Neuroscience,* 10: 269-29). The encephalic NSE concentration ranges from 0.4 to 2.2%, and may represent up to 4% of the total soluble proteins in some neurons (Marangos P J ibid). In adult brains, higher concentrations of NSE are found in the gray matter (e.g., neocortex) and lower levels in the white matter (e.g., pyramidal tract and corpus callosum).

NSE was also reported to be present in platelets and red blood cells (Day I N & Thompson R J (1984). Levels of immunoreactive aldolase C, creatine kinase-BB, neuronal and non-neuronal enolase, and 14-3-3 protein in circulating human blood cells. *Clinica Chimica Acta,* 136: 219-228.). The presence of NSE in red blood cells is clinically relevant because even a mild hemolysis of 2% may increase serum NSE (sNSE) levels five-fold (7).

Besides being expressed selectively in neurons, NSE has a high stability in biological fluids and, as a free soluble cytoplasmic protein, can easily diffuse to the extracellular medium and cerebrospinal fluid (CSF) when neuronal membranes are injured. Hence, measurements of CSF-NSE (cNSE) may be an attractive marker of neuronal damage (2,3). There are some peculiarities, however, that have to be considered when cNSE or other CSF neuronal markers are assayed: nature, location and extension of the lesion; CSF turnover and time elapsed between neuronal injury and CSF sample collection.

Several studies have shown that cNSE yields a reliable estimate of the severity of neuronal injury as well as clinical outcome of patients with serious clinical manifestations such as in cases of stroke (Hay E, Royds J A, Davies-Jones G A, Lewtas N A, Timperley W R & Taylor C B (1984). Cerebrospinal fluid enolase in stroke. *Journal of Neurology, Neurosurgery and Psychiatry*, 47: 724-729.), head injury (Persson L, Hardemark H G, Gustafsson J, Rundstrom G, Mendel-Hartvig I, Esscher T & Pahlman S (1987). S-100 protein and neuron-specific enolase in cerebrospinal fluid and serum: markers of cell damage in human central nervous system. *Stroke*, 18: 911-91), anoxic encephalopathy (Roine R O, Somer H, Kaste M, Viinikka L & Karonen S L (1989). Neurological outcome after out-of-hospital cardiac arrest. Prediction by cerebrospinal fluid enzyme analysis. *Archives of Neurology*, 46: 753-756.), encephalitis (Studahl M, Rosengren L, Gunther G & Hagberg L (2000). Difference in pathogenesis between herpes simplex virus type 1 encephalitis and tick-borne encephalitis demonstrated by means of cerebrospinal fluid markers of glial and neuronal destruction. *Journal of Neurology*, 247: 636-642.), brain metastasis (Royds J A, Timperley W R & Taylor C B (1981). Levels of enolase and other enzymes in the cerebrospinal fluid as indices of pathological change. *Journal of Neurology, Neurosurgery and Psychiatry*, 44: 1129-113), and status epilepticus (Correale J, Rabinowicz A L, Heck C N, Smith T D, Loskota W J & DeGiorgio C M (1998). Status epilepticus increases CSF levels of neuron-specific enolase and alters the blood- brain barrier. *Neurology*, 50: 1388-1391.). Normal plasma concentration of the gamma gamma isoform is <10 ng/ml (120 pM).

Creatine kinase is an 85 kDa cytosolic enzyme found in the heart, brain, and skeletal muscle. CK occurs in three major isoenzymes, CK-MB (found mostly in your heart muscle), CK-BB (found mostly in your brain), and CK-MM (found in your heart and other muscles). CK in the blood comes mainly from the muscles. The CK in the brain almost never gets into the blood. CK-MB is released into the bloodstream following cardiac cell death. The normal plasma concentration of CK-MB is <5 ng/ml. Serum levels of CK and CKMB become elevated 3-6 hours after the onset of symptoms of myocardial infarction (MI), peak at approximately 18 hours, and return to normal in approximately 3 days. Following successful fibrinolysis, CK and CKMB usually peak in <12 hours. Newer mass assays (ng/mL) for CKMB are more sensitive and specific than older activity assays and permit the detection of small elevations in CKMB without elevation in overall CK. These minor CKMB elevations have been associated with higher long-term risk of adverse cardiac events, particularly following percutaneous coronary intervention (PCI).

Glycogen phosphorylase (GP) is an 188 kDa intracellular allosteric enzyme that catalyzes the removal of glucose (liberated as glucose-1-phosphate) from the nonreducing ends of glycogen in the presence of inorganic phosphate during glycogenolysis.

We now discuss glycogen phosphorylase (GP) and its isoenzyme BB in the diagnosis of ischaemic myocardial injury. Early identification and confirmation of acute myocardial infarction is essential for correct patient care and disposition decision in the emergency department. In this respect, glycogen phosphorylase isoenzyme BB (GPBB) based on its metabolic function is an enzyme for early laboratory detection of ischaemia. In the aerobic heart muscle GPBB together with glycogen is tightly associated with the vesicles of the sarcoplasmic reticulum. Release of GPBB, the main isoform in the human myocardium, essentially depends on the degradation of glycogen, which is catalyzed by GP. Ischaemia is known to favour the conversion of bound GP in the beta form into GP a, thereby accelerating glycogen breakdown, which is the ultimate prerequisite for getting GP into a soluble form being able to move freely in the cytosol. The efflux of GPBB into the extracellular fluid follows if ischaemia- induced structural alterations in the cell membrane become manifest. The clinical application of GPBB as a marker of ischaemic myocardial injury is a very promising tool for extending the knowledge of the severity of myocardial ischaemic events in the various coronary syndromes. The rational roots of this development were originated from Albert Wollenberger's research work on the biochemistry of cardiac ischaemia and the transient acceleration of glycogenolysis mainly brought about by GP activation. GP is present as a homodimer, which associates with another homodimer to form a tetrameric enzymatically active phosphorylase A. There are three isoforms of GP that can be immunologically distinguished. The BB isoform is found in brain and cardiac tissue, the MM isoform is found in skeletal muscle and cardiac tissue, and the LL isoform is predominantly found in liver (See for instance Mair, J. et al., Br. Heart J. 72:125-127, 1994). GP-BB is normally associated with the sarcoplasmic reticulum glycogenolysis complex, and this association is dependent upon the metabolic state of the myocardium (See for instance Mair, J., Clin. Chim. Acta 272:79-86, 1998). At the onset of hypoxia, glycogen is broken down, and GP-BB is converted from a bound form to a free cytoplasmic form (See for instance Krause, E. G. et al. Mol. Cell Biochem. 160-161:289-295, 1996). The normal plasma GP-BB concentration is <7 ng/ml (36 pM). The plasma GP-BB concentration is significantly elevated in patients with acute myocardial infarction and unstable angina with transient ST-T elevations, but not stable angina (See for instance Mair, J. et al., Br. Heart J. 72:125-127, 1994; Mair, J., Clin. Chim. Acta 272:79-86, 1998; Rabitzsch, G. et al., Clin. Chem. 41:966-978, 1995; Rabitzsch, G. et al., Lancet 341:1032-1033,1993). Furthermore, GP-BB also can be used to detect perioperative acute myocardial infarction and myocardial ischemia in patients undergoing coronary artery bypass surgery (See for instance Rabitzsch, G. et al., Biomed. Biochim. Acta 46:S584-S588, 1987; Mair, P. et al., Eur. J. Clin. Chem. Clin. Biochem. 32:543-547, 1994). GP-BB has been demonstrated to be a more sensitive marker of unstable angina and acute myocardial infarction early after onset than CK-MB, cardiac tropopnin T, and myoglobin (See for instance Rabitzsch, G. et al., Clin. Chem. 41:966-978, 1995). Because it is also found in the brain, the plasma GP-BB concentration also may be elevated during ischemic cerebral injury. GP-BB is released into the bloodstream under ischemic conditions that also involve an increase in the permeability of the cell membrane, usually a result of cellular necrosis. GP-BB is significantly elevated within 4 hours of chest pain onset in individuals with unstable angina and transient ST-T ECG alterations, and is significantly elevated while myoglobin, CK-MB, and cardiac troponin T are still within normal levels (See for instance Mair, J. et al., Br. Heart J. 72:125-127, 1994). Furthermore, GP-BB can be significantly elevated 1-2 hours after chest pain onset in patients with acute myocardial infarction (See for instance Rabitzsch, G. et al., Lancet 341:1032-1033, 1993). The plasma GP-BB concentration in patients with unstable angina and acute myocardial infarction can exceed 50 ng/ml (250 pM) (Mair, J. et al., Br. Heart J. 72:125-127, 1994; Mair, J., Clin. Chim. Acta 272:79-86, 1998; Krause, E. G. et al., Mol. Cell Biochem. 160-161:289-295, 1996; Rabitzsch, G. et al., Clin. Chem. 41:966-978, 1995; Rabitzsch, G. et al., Lancet 341:1032-1033, 1993). GP-BB appears to be a very sensitive marker of myocardial ischemia, with specificity similar to that of CK-BB. GP-BB plasma concentrations are elevated within the first 4 hours after acute myocardial infarction onset, which suggests that it may be a very useful early marker of myocardial damage. Furthermore, GP-BB is not only a more specific marker of cardiac tissue damage, but also ischemia, since it is released to an unbound form during cardiac ischemia and would not normally be released upon traumatic injury. This is best illustrated by the usefulness of GP-BB in detecting myocardial ischemia during cardiac surgery. GP-BB may be a very useful marker of early myocardial ischemia during acute myocardial infarction and severe unstable angina.

Heart-type fatty acid binding protein (H-FABP) a 15 kD cytoplasmic protein involved in lipid homeostasis, is abundant in heart muscle, as well as the kidneys, brain, skeletal muscle and adrenals. It has recently been reported to detect early myocyte injury in patients with acute myocardial infarction (see for instance Ishii J, Wang J, Naruse H, et al. Serum concentrations of myoglobin vs human heart-type cytoplasmic fatty acid-binding protein in early detection of acute myocardial infarction. *Clin Chem* 1997; 43:1372-8).

Similar to the use of heart-type fatty acid-binding protein (H-FABP) as a plasma marker for the rapid detection of cardiac injury (see for instance Ishii J, Ibid; and Glatz J F C, Van der Voort D, Hermens W T. Fatty acid-binding protein as the earliest available plasma marker of acute myocardial injury. J Clin Ligand Assay 2002;25:167-177 Glatz J F C, Van der Voort D, Hermens W T. Fatty acid-binding protein as the earliest available plasma marker of acute myocardial injury. J Clin Ligand Assay 2002;25:167-177), brain-type FABP (B-FABP) and H-FABP (Myers-Pane S C, Hubbel T, Pu L, Schnütgen F, Börchers T, Wood W G, et al. Isolation and characterization of two fatty acid-binding proteins from mouse brain. J Neurochem 1996;66:1648-1656.) may be suitable markers for the detection of brain injury. B-FABP and H-FABP are members of a family of nine distinct FABP types, each named after the tissue in which it was first detected (Glatz J F, Van der Vusse G J. Cellular fatty acid-binding proteins: their function and physiological signification. Prog Lipid Res 1996;3:243-282). FABPs are 15-kDa cytoplasmic, nonenzymatic proteins involved in the intracellular buffering and transport of long-chain fatty acids. FABPs are released rapidly from damaged cells into the circulation and are cleared from the circulation by the kidney with a plasma half-life of 20 min (Glatz J F C, 2002, Ibid). B-FABP was first identified in the brains of rodents and showed diverse tissue production during development. In adult-stage mice, B-FABP is produced in very low concentrations and is detected only in glial cells (presumptive astrocytes) of the white matter (Kurtz A, Zimmer A, Schnütgen F, Brüning G, Spener F, Müller T. The expression pattern of a novel gene encoding brain-fatty acid binding protein correlates with neuronal and glial cell development. Development 1994;120: 2637-2649.). Unlike B-FABP, H-FABP is detected in the neurons of the gray matter (neuronal cell bodies) in mice and rats and constitutes 0.01% of total brain cytosolic protein (Myers-Pane S C, Ibid).

Pelsers et al (Pelsers et al., Brain- and Heart-Type Fatty Acid-Binding Proteins in the Brain: Tissue Distribution and Clinical Utility *Clinical Chemistry.* 2004;50:1568-1575.) developed a B-FABP ELISA that measures the concentrations of both B-FABP and H-FABP in the brain and investigated whether brain injury in mild traumatic brain injury (MTBI) and in electroconvulsive therapy (ECT) can be detected by the release of these proteins into the blood serum. The tissue concentration of B-FABP was highest in the frontal lobe, whereas H-FABP was highest in the ponsAn important finding was that the H- FABP/B-FABP ratio differs among the various parts of the human brain studied, indicating that this ratio in plasma or serum may be used to locate the site of brain injury. In the MTBI study, the H-FABP/B-FABP ratio was assessed in serum and found to be 0.58, indicating a relatively higher release of B-FABP compared with H-FABP. However, no data (e.g., positron emission tomography scan or magnetic resonance imaging) were available to correlate the localization of brain injury with the serum values. In addition, as stated above, potential drawbacks to use of the H-FABP/B-FABP ratio are the developmental and age-related changes in tissue production of both proteins.

The use of B- and H-FABP as biomarkers for early identification and treatment stratification of MTBI patients presenting with headache, dizziness, and nausea in the emergency room may improve patient care and outcome. It is known that in patients with acute ischemic injury, rapid initiation of treatment will decrease the amount of neuronal cell death. Traumatic brain injury is a major cause of morbidity and mortality, and can give stroke-like symptoms. Although current knowledge about the pathophysiology of MTBI is limited, traumatically induced axonal damage is thought to be the pathophysiologic mechanism in MTBI (Povlishock J T, Jenkins L W. Are the pathobiological changes evoked by traumatic brain injury immediate and irreversible?. Brain Pathol 1995;5:415-426), as demonstrated by increased concentrations of S100B and NSE. In the MTBI group of Pelsers et al, both B-FABP and H-FABP were increased in significantly ($P<0.05$) more cases (68% and 70%, respectively) than were S100B (45%) and NSE (51%), suggesting a difference in sensitivity. However, no significant correlations among serum concentrations of each of the biomarkers: only 45% of the samples had increases in both B-FABP and H-FABP, suggesting either different release kinetics or injury in different areas of the brain. The latter seems more likely because the release kinetics are not expected to differ among types of FABP (De Groot M J M, Wodzig K W H, Simoons M L, Glatz J F C, Hermens W T. Measurement of myocardial infarct size from plasma fatty acid-binding protein or myoglobin, using individually estimated clearance rates. Cardiovasc Res 1999;44:315-324). The FABPs, as well as myoglobin and S100B, are cytosolic proteins and, therefore, are released simultaneously from injured cells. In addition, the release of cerebrovascular proteins into blood plasma is dependent on disruption of the blood-brain barrier [reviewed recently by Marchi et al.]. Because these proteins are of similar size (FABP, 15 kDa; myoglobin, 17 kDa; S100B, 22 kDa), they will not differentially pass through the blood-brain barrier. The similarity in the sizes of these molecules also implies that the elimination of these proteins from plasma occurs by renal clearance and at equal rates. B- and H-FABP and S100B (Jonsson H, Johnsson P, Hoglund P, Alling C, Blonquist S. Elimination of S100B and renal function after cardiac surgery. J Cardiothorac Vasc Anesth 2000;6:698-701) have a plasma half-life of 20-25 min, indicating that the so-called diagnostic time window is limited but similar for these FABPs and S100B.

S-100 is a 21 kDa cytosolic protein that is localized in astrocytes, Schwann cells, Melanocytes, and adipocytes. It participates in cell-cell communication (astrocyte-neuron), cell growth, intracellular signal transduction, and is involved in the development and maintenance of the central nervous system. The S-100 protein family constitutes a subgroup of Ca(2+)-binding proteins of the EF-hand type comprising three dimeric isoforms, S-100a0, S-100a and S-100b, plus a number of structurally related proteins displaying 28-55% homology with S-100 subunits. Both intracellular and extracellular roles have been proposed for S-100 protein. Within cells, S-100 protein has been reported to regulate protein phosphorylation, ATPase, adenylate cyclase, and aldolase activities and Ca(2+)-induced Ca2+ release. Also, cytoskeletal systems, namely microtubules and microfilaments have been reported to be regulated by the protein in the presence of Ca2+. Some molecular targets of S-100 protein within cells, have been identified. This is the case with microtubule proteins, caldesmon, and a brain aldolase. S-100 protein has been reported to be secreted; extracellular S-100 protein can stimulate neuronal differentiation, glial proliferation, and prolactin secretion. S-100b is found mainly in glial cells and Schwann cells, where it is a major cytosolic component (Kato, K. and Kimura, S., Biochim. Biophys. Acta 842:146-150, 1985; Hasegawa, S. et al., Eur. Urol. 24:393-396,1993). S-100 has a ±1% per year relative increase with age (C. May, J. A. Kaye, J. R. Atach, M. B. Schaprio, R. P. Friedland and S. L. Rapoport, Cerebrospinal fluid production is reduced in healthy aging. *Neurology* 40 (1990), pp. 500-503.), After either mild or severe head injury S-100B serum levels correlate both with clinical outcome at sixth month and the severity of primary and secondary brain damage [A. Raabe, C. Grolms, O. Sorge, M. Zimmermann and V. Seifert, Serum S-100B protein in severe head injury (see comments). *Neurosurgery* 45 (1999), pp. 477-483. and B. Romner, T. Ingebrigtsen, P. Kongstad and S. E. Borgesen, Traumatic brain damage: serum S-100 protein measurements related to neuroradiological findings. *J. Neurotrauma* 17 (2000), pp. 641-647.]. On the contrary, undetectable blood levels of S-100B predict normal intracranial findings on CT scan. Therefore, S-100B may be used to select patients for CT scanning after mild head injury [Romner, Ibid]. A number of authors investigated the release patterns of blood S-100B after acute stroke and demonstrated associations with the volume of lesions, clinical status and functional outcome [H. D. Abraha, R. J. Butterworth, P. W. M. Bath, W. S. Wassif, J. Garthwaite and R. A. Sherwood, Serum S-100 protein, relationship to clinical outcome in acute stroke. *Ann. Clin. Biochem.* 34 (1997), pp. 336-370.; T. Buüttner, S. Weyers, T. Postert, R. Sprengelmeyer and W. Khun, S-100 protein: serum marker of focal brain damage after ischemic territorial MCA infarction. *Stroke* 28 (1997), pp. 1961-1965.; K. Fassbender, R. Schmidt, A. Schreiner, M. Fatar, F. Mühlhauser, M. Daffertshofer and M. Hennerici, Leakage of brain-originated proteins in peripheral blood: temporal profile and diagnostic value in early ischemic stroke. *J. Neurol. Sci.* 148 (1997), pp. 101-105.; U. Missler, M. Wiesmann, C. Friedrich and M. Kaps, S-100 protein and neuron-specific enolase concentrations in blood as indicators of infarction: volume and prognosis in acute ischemic stroke. *Stroke* 28 (1997), pp. 1956-1960.; and W. T. Wunderlich, A. B. Ebert, T. Kratz, M. Gortler, S. Jost and M. Herrmann, The early neurobehavioral outcome after stroke is related to the release of neurobiochemical markers of brain damage. *Stroke* 30 (1999), pp. 1190-1195.]. The release pattern of S-100B was interpreted to mirror the underlying pathophysiology of acute stroke. Furthermore, clinical studies demonstrated a significant association between early serum concentrations of S-100B and the clinical and/or functional outcome after stroke [Fassbender, ibid.]. Recently, Herrmann et al. [M. Herrmann, P. E. Vos, M. T. Wunderlich, C. H. de Bruijn and K. J. Lamers, Release of glial tissue-specific protein after acute stroke: a comparative analysis of serum concentrations of protein S-100B and glial fibrillary acidic protein. *Stroke* 31 (2000), pp. 2670-2677.] studied a comparative analysis of GFAP and S-100E serum concentrations in 32 patients with infarcts in the anterior circulation system after acute stroke. The release of both markers was found to be significantly correlated and the post-stroke blood values were associated with the size of brain lesions, the neurological status and the short-term outcome of the patients. However, the release pattern of both glia markers differed between different subtypes of stroke. GFAP was found to be a more sensitive marker of brain damage in patients with smaller lacunar lesions or minor strokes.

Markers Related to Coagulation

Plasmin is the enzymatically active form of the plasminogen (Pig) zymogen. It is a 78 kDa active serine protease plasmin that crosslinks with fibrin. Plg is activated in humans by two Plg activators—tissue-type Plg activator (tPA) and urokinase-type Plg activator (uPA). Plasmin not only binds but also degrades many matrix proteins—including fibronectin, von Willebrand factor, thrombospondin, and laminin—at lysyl or arginyl peptide bonds. PAI-1 also directly inhibits plasmin (Hekman and Loskutoff 1988). PAI-1 appears to play a major role in determining the proliferative response to vascular injury by inhibiting the degradation of fibrin and several extracellular matrix proteins by plasmin. The proteolytic network of susceptible matrix proteins is further extended to include the collagens and elastin by the ability of plasmin to activate certain matrix metalloproteinases (MMPs), which, in turn, can activate still others. Also, certain growth factors, cytokines, and chemokines can be released, activated, and/or degraded by plasmin (reviewed in Carmeliet & Collen, 1997; Lijnen and Collen, 1996; Lijnen et al., 1996b; Lijnen et al., 1998; Plow et al., 1995 and Waisman, 2003). Plasmin-alpha2-antiplasmin complex (PAP) is an index of recent fibrinolytic activity. The normal serum concentration of PAP is <1 microgram/ml (6.9 nM).

Beta-thromboglobulin (betaTG) is composed of 81 amino acid residues forming into four identical subunits. It makes up 10% of the alpha granules contents, is released under the influence of known platelet activators such as ADP, collagen, immune complexes, and thrombin, and is produced by lysis of PF4 and platelet basic protein. It has a half-life in plasma of about 100 minutes. The normal plasma concentration of PTG is <40 ng/ml (1.1 nM), however, this is influenced by age, time of day, specimen anticoagulation, and certain drugs such as beta blockers. Beta TG has been shown to be significantly higher (171 IU/ml vs. 32 IU/ml, p<0.001) in stroke patients, in atherothrombotic and cardioembolic stroke, but not for lacunar infarctions (Szegedi et al. Molecular markers of endothelial dysfunction in acute ischemic stroke Ideggyogy Sz. 2002 Mar. 20;55(3-4):102-8.).

PF4 is an abundant platelet alpha-granule constituent that is released during the process of platelet activation and that accumulates in high concentrations on endothelial cell surfaces after acute vessel injury. Human platelets contain about 20 micrograms of $PF4/10^9$ platelets, and physiologic serum concentrations are 5-10 micrograms/mL. Human PF4 is a protein of 7800 Da that contains 70 amino acid residues and exists as a tetramer at physiologic pH and tonicity. Its isoelectric point is 7.6; however, it is quite asymmetric, having an extremely anionic N-terminal domain that contains five negatively charged residues in the first seven amino acids and a cationically charged carboxy-terminal end that contains four lysine residues in the terminal 12 amino acids. Perhaps its most outstanding chemical feature is its extremely high affinity for heparin ($K_D$=5-20 nM).

PF4 released by activated platelets accumulates on endothelial surfaces, binds to TM in a manner similar to the eosinophil cationic proteins, impairs TM anticoagulant function, and thereby promotes thrombosis. Instead, PF4 unexpectedly stimulates TM-mediated generation of APC by as much as 25-fold its usual rate. This stimulation of TM function was specific for PF4 because it did not occur in the presence of the two other major platelet alpha-granule heparin- binding proteins thrombospondin and beta-thromboglobulin. This suggests that PF4 enhances the affinity of the thrombin-TM complex for PC. In addition, when PC lacking its anionic gamma-carboxyglutamic acid (Gla) domain was substituted for native PC, no such stimulatory effect was seen, suggesting a possible binding interaction between PF4 and the Gla domain of PC (Slungaard, A Platelet factor 4 modulation of the thrombomodulin-protein C system. Critical Care Medicine. THE MARGAUX V CONFERENCE ON CRITICAL ILLNESS PROTEIN C PATHWAYS: BEDSIDE TO BENCH. 32(5) Supplement:S331-S335, May 2004). Thus Thrombin is generated in the immediate vicinity of injury, recruiting activated and degranulating platelets and causing them to release PF4. PF4 binds to circulating PC via its Gla domain, and this PF4—PC complex then binds to the thrombin-TM complex through an interaction with the TM GAG domain, resulting in enhanced generation of APC, creating a local and downstream anticoagulant environment and increasing circulating APC levels.

Levels of PF4 in the blood may be associated with clot formation and/or any condition that causes platelet activation, such as acute stroke, atherosclerosis, or even surgery (For instance see Serebruany et al., Enhanced platelet/endothelial activation in depressed patients with acute coronary syndromes: evidence from recent clinical trials. Blood Coagul Fibrinolysis. 2003 September; 14(6):563-7.; Rapold, H et al., Fibrin formation and platelet activation in patients with myocardial infarction and normal coronary arteries. Eur Heart J. 1989 April; 10(4):323-33; Nilsson J et al., Association between high levels of growth factors in plasma and progression of coronary atherosclerosis. J Intern Med. 1992 November; 232(5):397-404.).

The soluble fibrin monomer-fibrinogen complex (SF) is a complex coupling fibrin monomer and fibrinogen molecules to be formed in the early-activated state of blood coagulation. Thus such a molecular complex is expected to serve as a parameter for the diagnosis of thrombus formation and disseminated intravascular coagulation (DIC), in particular its early stage. As the level of SF reflects the thrombin generation activity in plasma, it would serve as a strong tool to selectively kick up the state of thrombin generation. The SF levels in DIC patients have been shown to be significantly higher than those in the subclinical DIC/hypercoagulable state, and in non-DIC patients (Koga S, A novel molecular marker for thrombus formation and life prognosis—clinical usefulness of measurement of soluble fibrin monomer-fibrinogen complex (SF), Rinsho Byori. 2004 April; 52(4):355-61).

Fibrinopeptides A and B (FPA and FPB) are released by the proteolytic action of thrombin on fibrinogen and are therefore markers of thrombin activity. FPA is a 16 amino-acid peptide cleaved from the aminoterminus of the fibrinogen-chain with a very short half-life in plasma (3-5 min). FPA that circulates in three different forms [J. A. Koehn and R. E. Canfield, Purification of human fibrinopeptides by high performance liquid chromatography. Anal. Biochem. 116 (1981), pp. 349-356.] is released more rapidly from fibrinogen than is FPB, resulting in the intermediate fibrin I molecule (des AA-fibrin). FPB is released from the aminoterminus of the -chain of fibrinogen or fibrin I and is a 14 amino- acid peptide. The sequential cleavage of FPA and FPB results in formation of fibrin II monomer (des AABB-fibrin).

FPA can also be measured in urine collected over 24 h; measurements correlate with plasma levels. Several plasma assays for FPA have been developed but none of these is suitable for bedside clinical application because of the very long turn-around times. Furthermore, measurement of FPA requires meticulous acquisition, collection, and processing of blood samples to avoid thrombin elaboration and ex vivo increases in FPA concentration [P. R. Eisenberg, Novel antithrombotic strategies for the treatment of coronary artery thrombosis: a critical appraisal. J. Thromb. Thrombolysis 1(1995), pp. 237-250].

The use of activation markers of thrombosis and fibrinolysis for early risk stratification of patients with ACS is still under study. The hypothesis currently tested is that patients who show marked elevations of these activation markers during the initial hours after symptom onset are at the highest risk of progression of coronary thrombosis and of its complications, i.e. myocardial infarction and death. Eisenberg et al. [P. R. Eisenberg, J. L. Kenzora, B. E. Sobel, P. A. Ludbrook and A. S. Jaffe, Relation between ST segment shifts during ischemia and thrombin activity in patients with unstable angina. J. Am. Coll. Cardiol. 18 (1991), pp. 898-903.] studied patients with unstable angina and found that those with reversible ST-segment shifts had higher FPA plasma levels than those with T-wave inversion alone. At coronary angiography, 55% of patients with ST-segment shifts had lesions with morphologic characteristics consistent with atherosclerotic plaque complicated by thrombosis compared with 22% of those with T-wave inversion. Ardissino et al [D. Ardissino, P. Merlini, G. Gamba et al., Thrombin activity and early outcome in unstable angina pectoris. Circulation 93 (1996), pp. 1634-1639.] have recently studied 150 patients with unstable angina and found that those with elevated FPA plasma levels had significantly higher incidence of death or non-fatal myocardial infarction than patients with normal FPA levels. These observations support the concept that the measurement in plasma of activation markers, namely FPA, may be a sensitive method to detect ongoing thrombus formation in patients with ACS. Plasma levels of FPA on admission, however, do not seem to predict clinical outcome in patients with acute myocardial infarction eligible for reperfusion, as judging from the results of a GUSTO-I substudy where patients with and without death or re-infarction at 30 days had similar FPA plasma levels at the time of hospital presentation [C. Granger, R. Becker, R. Tracy et al., Thrombin generation, inhibition and clinical outcomes in patients with acute myocardial infarction treated with thrombolytic therapy and heparin: results from the GUSTO-I Trial. GUSTO-I hemostasis substudy group. Global utilization of streptokinase and TPA for occluded coronary arteries. J. Am. Coll. Cardiol. 31 (1998), pp. 497-505.].

Platelet-derived growth factor (PDGF) is one of the most potent serum mitogens as well as one of the most extensively studied growth factors, and may be a marker of vascular injury and platelet activation. PDGF B-chain is a homologue of the simian sarcoma virus transforming protein, v-sis, possessing the activity to render cells competent to enter the G1-S cell cycle phases Heldin & Westermark, 1999). PDGF exists as a dimer in various combinations, i.e. AA, BB, AB, CC and DD, binding two structurally related tyrosine kinase receptors, alpha and beta, with different affinities (Bergsten et al., 2001; Gilbertson et al., 2001; Heldin et al., 2002). The C- and D-chains are the recently isolated members that are proteolytically cleaved before binding the receptors. The alpha-receptor binds A-, B- and C-chains, whereas the beta-receptor binds B- and D- chains. However, both CC and DD can bind and dimerise the alpha-beta receptor. Binding of PDGF induces dimerisation and mutual phosphorylation of the two receptors, leading to activation of several intracellular molecules, propagating cascades of different signalling pathways (Heldin et al., 1998). The alpha-receptor plays important roles in the development of neural crest-derived cells and somites (Soriano, 1997; Tallquist & Soriano, 2003), and the alpha- receptor, of the mural cells of blood vessels (Hellstrom et al., 1999; Lindahl et al., 1997). Neurons and glial cells of the CNS and PNS can express PDGF and its receptors, which are considered to stimulate their proliferation, differentiation and survival (Eccleston et al., 1993; Erlandsson et al., 2001; Funa & Åhgren, 1997; Raff, 1989; Sasahara et al., 1991; Smits et al., 1993; Yeh et al., 1991). The PDGF alpha-receptor can be up-regulated in fibroblasts and blood vessels during wound healing and chronic inflammation (Reuterdahl et al., 1991; 1993). Plasma PDGF has been seen to be elevated in patients with acute myocardial infarction (Ogawa, H. et al., Am. J. Cardiol. 69:453-456, 1992). The normal plasma concentration of PDGF is <0.4 ng/ml (15 pM).

Prothrombin fragment 1+2 (F1+2) is a 32 kDa polypeptide released from the prothrombin during its activation to thrombin by the prothrombinase complex. Measurement of circulating levels of F1+2 has been considered a specific marker of thrombin generation in vivo (Bauer K A, Broekmans A W, Bertina R M, Conard J, Horellou M H, Samama M M, Rosenberg R D. Hemostatic enzyme generation in the blood of patients with hereditary protein C deficiency. Blood. 1988; 71: 1418-1426.; Van der Poll T, Buller H R, ten Cate H, Worterl C H, Bauer K A, van Deventer S J, Hack C E, Sauwervein H P, Rosenberg R D, ten Cate J W. Activation of coagulation after administration of tumor necrosis factor to normal subjects. *N Engl J. Med.* 1990; 322: 1622-1627.). Elevated F1+2 has been found in patients with peripheral arterial disease, coronary atherosclerosis, and in relation to the presence of conventional CAD risk factors, such as age, smoking, and dyslipidemia (Kienast J, Thompson S G, Raskino C, Pelzer H, Fechtrup C, Osterman H, van de Loo J. Prothrombin activation fragment 1+2 and thrombin antithrombin complexes in patients with angina pectoris. Relation to the presence and severity of coronary atherosclerosis. *Thromb Haemost.* 1993; 70: 550-553; Cushman M, Psaty B M, Macy E, Bovill E G, Cornell E S, Kuller L H, Tracy R P. Correlates of thrombin markers in an elderly cohort free of clinical cardiovascular disease. *Arterioscler Thromb Vasc Biol.* 1996; 16: 1163-1169; Musial J, Pajal A, Undas A, Kavalec E, Topoi-Madry R, Pazucha T, Grzywacz M, Szczeklik A. Thrombin generation markers and coronary heart disease risk factors in a Polish population sample. *Thromb Haemost.* 1997; 77: 697-700.). F1+2 has a half-life of approximately 90 minutes in plasma.

P-selectin is the largest of the known selectins at 140 kDa. It contains nine consensus repeats (CR) and extends approximately 40 nm from the endothelial surface. Other names for P-selectin include CD62P, Granule Membrane Protein 140 (GMP-140), and Platelet Activation-Dependent Granule to External Membrane Protein (PADGEM). P-selectin is expressed in a-granules of activated platelets and granules of endothelial cells. Within minutes of stimulation of the endothelial cells by inflammatory mediators such as histamine, thrombin, or phorbol esters, P-selectin is surface-expressed. Expression of P-selectin also occurs from the surgical trauma endured during preparation of the tissues for intravital microscopy. The expression is short-lived, reaching its peak after only ten minutes. Additional synthesis of P-selectin is brought about within two hours by cytokines such as interleukin-1 (IL-1) or tumor necrosis factor a(TNF-a). The primary ligand for P-selectin is PSGL-1 (P-selectin glycoprotein ligand-1) which is constitutively found on all leukocytes. Other ligands for P-selectin include CD24 and uncharacterized ligands. The transient interactions between P-selectin and PSGL-1 allow leukocytes to roll along the venular endothelium. Accordingly,. P-selectin is largely responsible for the rolling phase of the leukocyte adhesion cascade. P-selectin can also mediate capture when L- selectin is not present.

Activated platelets in the circulation are thrombogenic and interact with a variety of other blood or vascular cells including leukocytes. Under static and flow condition, platelet P-selectin supports the adhesion of platelets to neutrophils, monocyte/macrophages, and a subset of lymphocytes. Thus, an increased expression of platelet surface P-selectin might induce increased platelet adhesion to circulating leukocytes which is supported by findings of enhanced platelet-leukocyte adhesion in patients with coronary heart disease (Meinrad Gawaz, Armin Reininger and Franz-Josef Neumann PLATELET FUNCTION AND PLATELET-LEUKOCYTE ADHESION 1N SYMPTOMATIC CORONARY HEART DISEASE. EFFECTS OF INTRAVENOUS MAGNESIUM Thrombosis Research Volume 83, Issue 5 1996, Pages 341-349.). Elevated P-selectin levels have also been associated with stroke risk (Dwayne S. G. et al., Plasma von Willebrand Factor and Soluble P-Selectin as Indices of Endothelial Damage and Platelet Activation in 1321 Patients With Nonvalvular Atrial Fibrillation: Relationship to Stroke Risk Factors *Circulation*. 2002;106:1962.), worsening of stroke (Cha J K et al, Surface Expression of P-selectin on Platelets Is Related with Clinical Worsening in Acute Ischemic Stroke. *J Korean Med Sci*. 2002 December; 17(6):811-816.) and stroke (Cha J K et al, Increased platelet CD63 and P- selectin expression persist in atherosclerotic ischemic stroke. Platelets. 2004 February; 15(1):3-7 Zee et al, Polymorphism in the P-selectin and interleukin-4 genes as determinants of stroke: a population-based, prospective genetic analysis, Human Molecular Genetics, 2004, Vol.13, No. 4 389-396).

von Willebrand factor (vWF) is a glycoprotein composed of identical disulfide-linked subunits, each comprising 2050 amino acid residues and up to 22 carbohydrate chains, for a total mass of approximately 278 kDa of which 10% 19% is carbohydrate [Titani K, Kumar S, Takio K, Ericsson L H, Wade R D, Ashida K, Walsh K A, Chopek M W, Sadler J E, Fujikawa K. Amino acid sequence of human von Willebrand factor. *Biochemistry* 1986; 25: 3171 84.]. Two subunits joined at carboxyl terminal ends form dimers that are the building blocks of larger polymers [Mayadas T N, Wagner D D. von Willebrand factor biosynthesis and processing. *Ann N Y Acad Sci* 1991; 614: 153 66]. Inter-subunit disulfide bonds at the amino terminal ends of dimers form multimers that range in molecular mass from approximately 500 kDa to in excess of 10 000 kDa [Mayadas T N, Wagner D D. Vicinal cysteines in the prosequence play a role in von Willebrand factor multimer assembly. *Proc Natl Acad Sci USA* 1992; 89: 3531 5]. The multimers may appear as thin filaments up to 1300 nm long, about the diameter of a platelet, or as coiled molecules with a cross-section of 200-300 nm [Fowler W E, Fretto L J. Electron microscopy of von Willebrand factor. In: Zimmerman T S, Ruggeri Z M, eds. *Coagulation and Bleeding Disorders. The Role of Factor VIII and Von Wllebrand Factor*. New York: Marcel Dekker, 1989: 181 93.]. Shear forces in the circulation may 'uncoil' globular vWF molecules while they are transiently bound to vascular or cellular surfaces, but vWF bound to collagen may not undergo such a change [Novak L, Deckmyn H, Damjanovich S, Harsfalvi J. Shear-dependent morphology of von Willebrand factor bound to immobilized collagen. *Blood* 2002; 99: 2070 6.]. There appears to be a direct correlation between the size of vWF and its ability to induce the formation of platelet thrombi. The contribution of vWF to thrombus formation is both direct, by mediating the adhesion of platelets to components of the extracellular matrix and to one another, and indirect, by associating with the procoagulant factor VIII and preventing its rapid clearance from plasma thus allowing normal thrombin generation. The main function of vWF is to mediate adhesive interactions of platelets exposed to rapid blood flow. There are two distinct platelet receptors for VWF, the glycoprotein (GP) Ibalpha in the GP Ib IX V complex and the integrin alpha.sub.IIb beta.sub.3 (GP IIb IIIa complex). Platelet agglutination induced by the antibiotic ristocetin requires vWF as a cofactor and involves interaction with GP Ib alpha. The main mechanism regulating vWF size involves specific proteolysis, with a possible contribution from a disulfide bond reductase activity ascribed to thrombospondin-1. The latter process involves a rearrangement of disulfide bonds with 'depolymerization' of the larger multimers [Xie L, Chesterman C N, Hogg P J. Control of von willebrand factor multimer size by thrombospondin-1. *J Exp Med* 2001; 193: 1341 9.]. Thrombospondin-1 is abundant in the -granules of platelets from which it is released upon activation, and could contribute to the regulation of vWF multimer size at sites of vascular lesions, thus limiting thrombus growth. Unlike vWF stored in cellular organelles, which contains exclusively intact subunits, plasma-derived multimers always yield upon reduction a well-defined proportion of two subunit fragments [Zimmerman T S, Dent J A, Ruggeri Z M, Nannini L H. Subunit composition of plasma von Willebrand factor. Cleavage is present in normal individuals, increased in IIA and IIB von Willebrand disease, but minimal in variants with aberrant structure of individual oligomers (Types IIC, IID and IIE). *J Clin Invest* 1986; 77: 947 51.] that have an apparent molecular mass of 140 and 176 kDa and result from cleavage of the single bond between Tyr842 and Met843 [Dent J A, Berkowitz S D, Ware J, Kasper C K, Ruggeri Z M. Identification of a cleavage site directing the immunochemical detection of molecular abnormalities in type IIA von Willebrand factor. *Proc Natl Acad Sci USA* 1990; 87: 6306 10.]. This event separates a multimer into two smaller species, each presenting a cleaved subunit at the amino or carboxyl terminal end. The protease that cleaves vWF at the Tyr842-Met843 bond is ADAMTS-13 ['A Disintegrin-like and Metalloprotease domain (reprolysin-type) with Thrombo spondin type I motifs'][Gerritsen H E, Robles R, Lämmle B, Furlan M. Partial amino acid sequence of purified von Willebrand factor-cleaving protease. *Blood* 2001; 98: 1654 61], and the structure of the corresponding gene has been fully characterized [Zheng X, Chung D, Takayama T K, Majerus E M, Sadler J E, Fujikawa K. Structure of von Willebrand factor-cleaving protease (AD-AMTS13), a metalloprotease involved in thrombotic thrombocytopenic purpura. *J Biol Chem* 2001; 276: 41059 63]. The regulation of plasma vWF multimer size is an important process that may influence the onset and progression of arterial thrombosis, possibly with a pathogenic role in common conditions such as the acute occlusive complications of coronary artery disease. Elevated vWF has been shown to be a result of stroke and stroke subtype (Catto A J, Carter A M, Barrett J H, Bamford J, Rice P J, Grant P J. von Willebrand factor and factor VII: C in acute cerebrovascular disease. Relationship to stroke subtype and mortality.; Qizilbash N, Duffy S, Prentice C R, Boothby M, Warlow C. Von Willebrand factor and risk of ischemic stroke. Neurology. 1997 December; 49(6):1552-6.).

Tissue factor (TF) is a cell membrane-bound glycoprotein (MW 46 kDa) and a member of the class 2 cytokine receptor family. It is composed of a hydrophilic extracellular domain, a membrane-spanning hydrophobic domain, and a cytoplasmic tail of 21 residues, including a non-disulfide-linked cysteine. The mature protein, which is post-translationally modified to include carbohydrate moieties, is biologically active. Upon exposure to blood, perivascular cell-bound TF binds to factor VII, a vitamin K-dependent serine protease unique among coagulation factor zymogens in that it exists in a partially active state. Cleavage of factor VII to VIIa by thrombin, factor IXa, Xa, or XIIa increases its activity 100-fold. The affinity of TF for factor VIIa is increased by anionic phospholipids. The TF-factor VIIa complex can directly or indirectly activate factor X and thence generate thrombin (factor IIa). TF mediates hemostasis by: 1) complexing with factor VIIa to directly convert X to Xa (extrinsic pathway); or 2) indirectly generating Xa by converting IX to IXa, which, in turn, complexes with VIIIa to convert X to Xa (intrinsic pathway). Factor Xa, once generated, complexes with its co-factor, Va, to convert prothrombin (II) to thrombin (IIa) which, in turn, cleaves fibrinogen to generate fibrin or activate platelets. Among the inhibitors of these processes are TF pathway inhibitor (TFPI), and activated Protein C com- plexed with Protein S (APC/S). Heparin co-factor II, antithrombin III (ATIII), and alpha-2-macro-globulin are potent anti-thrombin agents which form ternary complexes with vitronectin (Vn) and heparin. Fibrinolysis is mediated by tissue-type plasminogen activator (tPA), and inhibited by PAI-1, bound to Vn. The latter also exerts anti-thrombin effects. Under physiological conditions TF is expressed by cells not in contact with blood such as vascular smooth muscle, mesenchymal and epithelial cells including placental villous stromal cells. However, TF is not normally expressed by cells in contact with the circulation (i.e., endothelium and villous trophoblasts). The pathological induction of TF expression in the endothelium contributes to the intravascular thrombosis of atherosclerosis and septic shock. Due to their perivascular location, enhanced TF expression by human endometrial DCs provides a mechanism to prevent hemorrhage during trophoblast invasion of the endometrial vasculature. Tissue factor expression is controlled at the transcriptional level in various cell types. Cytokines, growth factors, and serum transiently (1-4 hours) induce TF mRNA and protein in cultured cells from diverse tissues. The normal serum concentration of TF is <0.2 ng/ml (4.5 pM). In addition to hemostasis, TF is now known to mediate invasion and angiogenesis. These functions apparently require interaction with factor VIIa. Tissue factor has been shown to be correlated with both stroke (Abumiya T, Yamaguchi T, Terasaki T, Kokawa T, Kario K, Kato H. Decreased plasma tissue factor pathway inhibitor activity in ischemic stroke patients. Thromb Haemost. 1995 October; 74(4):1050-) and stroke subtype (Hirashima Y, Nakamura S, Suzuki M, Kurimoto M, Endo S, Ogawa A, Takaku A. Cerebrospinal fluid tissue factor and thrombin-antithrombin III complex as indicators of tissue injury after subarachnoid hemorrhage. Stroke. 1997 September; 28(9):1666-70.), and Atherosclerosis (Tremoli E, Camera M, Toschi V, Colli S. Tissue factor in atherosclerosis. Atherosclerosis. 1999 June; 144(2):273-83.).

Markers Related to Atherosclerotic Plaque Rupture

Atherosclerotic plaque rupture is part of a dynamic inflammatory process of atherosclerotic vascular disease which starts from inception and continues through plaque growth, rupture and ultimately thrombosis. Suggested markers of atherosclerotic plaque rupture that would be suitable for inclusion in a stroke or stroke sub-type diagnostic include human neutrophil elastase, inducible nitric oxide synthase, lysophosphatidic acid, malondialdehyde-modified low density lipoprotein, and various members of the matrix metalloproteinase (MMP) family, including MMP-1, -2, -3, 7, 9, 12, and -19, the main family members of which we discuss below.

Matrix metalloproteinases (MMPs) are a family of zinc-binding proteolytic enzymes that normally remodel the extracellular matrix and pathologically attack substrates as part of the neuroinflammatory response. MMP-2 (72 kDa, gelatinase A) and MMP-9 (92 kDa, gelatinase B) specifically attack type IV collagen, laminin, and fibronectin, which are the major components of the basal lamina around cerebral blood vessels. Proenzyme activation and enzyme activities are tightly regulated by tissue inhibitors of MMPs (TIMPs) and interactions with surrounding extracellular matrix molecules. Matrix metalloproteinases (MMPs) and tissue inhibitors of metalloproteinases (TIMPs) play a significant role in regulating angiogenesis, the process of new blood vessel formation. Interstitial collagenase (MMP-1), 72 kDa gelatinase A/type IV collagenase (MMP-2), and 92 kDa gelatinase B/type IV collagenase (MMP-9) dissolve extracellular matrix (ECM) and may initiate and promote angiogenesis. TIMP-1, TIMP-2, TIMP-3, and possibly, TIMP-4 inhibit neovascularization. A new paradigm is emerging that matrilysin (MMP-7), MMP-9, and metalloelastase (MMP-12) may block angiogenesis by converting plasminogen to angiostatin, which is one of the most potent angiogenesis antagonists. MMPs and TIMPs play a complex role in regulating angiogenesis. MMP-9 has been implicated as a marker of stoke severity (Montaner et al., Matrix Metalloproteinase Expression After Human Cardioembolic Stroke, *Stroke.* 2001;32:1759.)

Markers Related to Tissue Injury and Inflammation

C-reactive protein (CRP) is composed of 5 23-kd subunits. CRP is a member of the pentraxin family of innate immune response proteins. Although initially believed to be synthesized only by the liver in response to interleukin-6, recent evidence indicates that CRP is also produced in smooth muscle cells within human coronary arteries and is expressed preferentially in diseased vessels. [P. Calabro, J. T. Willerson and E. T. Yeh, Inflammatory cytokines stimulated C-reactive protein production by human coronary artery smooth muscle cells, *Circulation* 108 (2003), pp. 1930-1932.] and [W. J. Jabs, E. Theissing and M Nitschke et al., Local generation of C-reactive protein in diseased coronary artery venous bypass grafts and normal vascular tissue, *Circulation* 108 (2003), pp. 1428-1431.] One report found that levels of CRP mRNA within atherosclerotic plaque were 7- and 10-fold higher than levels found in the liver and normal blood vessels, respectively [K. Yasojima, C. Schwab, E. G. McGeer and P. L. McGeer, Generation of C-reactive protein and complement components in atherosclerotic plaques, *Am J Pathol* 158 (2001), pp. 1039-1051.]. Although traditionally considered a passive downstream marker of the inflammatory process, CRP has been shown in laboratory studies to influence vascular vulnerability directly by a variety of mechanisms, including enhanced expression of local endothelial cell surface adhesion molecules, monocyte chemoattractant protein-1, [V. Pasceri, J. T. Willerson and E. T. Yeh, Direct proinflammatory effect of C-reactive protein on human endothelial cells, *Circulation* 102 (2000), pp. 2165-2168.] and [V. Pasceri, J. S. Cheng, J. T. Willerson, E. T. Yeh and J. Chang, Modulation of C-reactive protein-mediated monocyte chemoattractant protein-1 induction in human endothelial cells by anti-atherosclerosis drugs, *Circulation* 103 (2001), pp. 2531-2534.] endothelin-1, and endothelial plasminogen activator inhibitor-1; reduced endothelial nitric oxide bioactivity; [S. Verma, S. H. Li and M. V Badiwala et al., Endothelin antagonism and interleukin-6 inhibition attenuate the proatherogenic effects of C-reactive protein, *Circulation* 105 (2002), pp. 1890-1896] [S. K. Venugopal, S. Devaraj, I. Yuhanna, P. Shaul and 1. Jialal, Demonstration that C-reactive protein decreases eNOS expression and bioactivity in human aortic endothelial cells, *Circulation* 106 (2002), pp. 1439-1441.] and [S. Verma, C. H. Wang and S. H Li et al., A self-fulfilling prophecy C-reactive protein attenuates nitric oxide production and inhibits angiogenesis, Circulation 106 (2002), pp. 913-919.] increased induction of tissue factor in monocytes; increased LDL uptake by macrophages; [T. P. Zwaka, V. Hombach and J. Torzewski, C-reactive protein-mediated low density lipoprotein uptake by macrophages Implications for atherosclerosis, *Circulation* 103 (2001), pp. 1194-1197.] and colocalization with the complement membrane attack complex within atherosclerotic lesions. Recent data also indicate that the expression of human CRP in CRP-transgenic mice directly enhances intravascular thrombosis in arterial injury and photochemical injury models of endothelial disruption[H. D. Danenberg, A. J. Szalai and R. V Swaminathan et al., Increased thrombosis after arterial injury in human C-reactive protein-transgenic mice, *Circulation* 108 (2003), pp. 512-515.]. The normal plasma concentration of CRP is <3 micrograms/ml (30 nM) in 90% of the healthy population, and <10 micrograms/ml (100 nM) in 99% of healthy individuals. Elevated levels of CRP have been shown to predict stroke risk (Gussekloo et al., C-reactive protein is a strong but nonspecific risk factor of fatal stroke in elderly persons. Arterioscler Thromb Vasc Biol. 2000 April;20(4): 1047-51.) and occurance (Ford E S, Giles W H. Serum C-reactive protein and self-reported stroke: findings from the Third National Health and Nutrition Examination Survey. Arterioscler Thromb Vasc Biol. 2000 April; 20(4):1052-6.).

IL-1 ligands (IL-1 and IL-1 beta, collectively referred to as IL-1) are pluripotent, proinflammatory cytokines that orchestrate inflammatory and host defense responses in the body. IL-1 augments T-cell responses to mitogens (and indirectly activates B cells), increases expression of vascular adhesion molecules, and induces a number of other proinflammatory cytokines, chemokines, and inflammation-associated molecules that form an amplifying cascade to stimulate an immune response. The net effect of inducing these other immune stimulatory molecules is to recruit and activate macrophages, lymphocytes, and neutrophils to fight infection and to stimulate wound healing in response to tissue damage (Dinarello, [1996]).

All ligands and receptor components of the IL-1 family (IL-1, IL-1, IL-1ra, IL-1R1, IL-1RII, AcP) are present within the brain, although they are expressed at low levels in the healthy central nervous system (CNS) (Vitkovic et al., [2000]). Microglia express caspase 1, the enzyme responsible for cleaving pro-IL-1 to its active form, and seem to be the earliest and major source of IL-1 after experimental CNS injury, infection, or inflammation (Eriksson et al., [1999]). Neurons, astrocytes, oligodendrocytes, and endothelial cells may also produce IL-1, but evidence suggests that their production is subsequent to the microglial response (Blasi et al., [1999]; Davies et al., [1999]; Pearson et al., [1999]; Vitkovic et al., [2000]). Several interleukins have been implicated as diagnostic markers of stroke, including IL-1 (Vila N, Chamorro A. Cytokines and acute- phase response in acute stroke. Stroke. 1995 September; 26(9):1729.) IL-6 (Tarkowski et al., Early intrathecal production of interleukin-6 predicts the size of brain lesion in stroke. Stroke. 1995 August; 26(8):1393-8.; Kim JS. Cytokines and adhesion molecules in stroke and related diseases. J Neurol Sci. 1996 May; 137(2):69-78) IL-1 beta, II-8, and IL-17 (Kostulas N et al., Increased IL-1beta, IL-8, and IL-17 mRNA expression in blood mononuclear cells observed in a prospective ischemic stroke study. Stroke. 1999 October; 30(10):2174-9.) and IL-1 receptor agonist (Basu A et al., The type 1 interleukin-1 receptor is essential for the efficient activation of microglia and the induction of multiple proinflammatory mediators in response to brain injury. J. Neurosci. 2002 Jul. 15;22(14): 6071-82.).

The family of IL (interleukin)-6-type cytokines comprises IL-6, IL-11, LIF (leukaemia inhibitory factor), OSM (oncostatin M), CNTF (ciliary neurotrophic factor), CT-1 (cardiotrophin-1) and CLC (cardiotrophin-like cytokine). They activate target genes involved in differentiation, survival, apoptosis and proliferation. The members of this cytokine family have pro- as well as anti- inflammatory properties and are major players in haematopoiesis, as well as in acute-phase and immune responses of the organism. IL-6-type cytokines bind to plasma membrane receptor complexes containing the common signal transducing receptor chain gp 130 (glycoprotein 130). Signal transduction involves the activation of JAK (Janus kinase) tyrosine kinase family members, leading to the activation of transcription factors of the STAT (signal transducers and activators of transcription) family. Another major signalling pathway for IL-6-type cytokines is the MAPK (mitogen-activated protein kinase) cascade. Receptors involved in recognition of the IL-6-type cytokines can be subdivided in the non-signalling a-receptors (IL-6R a, IL-11R a, and CNTFR a, where R refers to receptor) and the signal transducing receptors (gp130, LIFR, and OSMR). The latter associate with JAKs and become tyrosine phosphorylated in response to cytokine stimulation. Each of the IL-6-type cytokines is characterized by a certain profile of receptor recruitment that in all cases involves at least one molecule of gp130. IL-6, IL-11 and CNTF first bind specifically to their respective a-receptor subunits. Here, only the complex of cytokine and a-receptor efficiently recruits the signalling receptor subunits. Also, an a-receptor subunit has been postulated for CT-1 [Robledo, O., Fourcin, M., Chevalier, S., Guillet, C., Auguste, P., Pouplard-Barthelaix, A., Pennica, D. and Gascan, H. (1997) Signaling of the cardiotrophin-1 receptor. Evidence for a third receptor component. J. Biol. Chem. 272, 4855-4863], but since this putative receptor protein has not been cloned yet its existence is questionable. IL-6 and IL-11 are the only IL-6-type cytokines that signal via gp130 homodimers. The remaining IL-6 type cytokines signal via heterodimers of either gp130 and the LIFR (LIF, CNTF, CT-1 and CLC) or gp130 and the OSMR (OSM). Human OSM has the exceptional capability to recruit two different receptor complexes. It forms both LIFR-gp130 and OSMR-gp130 heterodimers. LIF and OSM directly engage their signalling receptor subunits without requirement for additional a-receptor subunits.

The normal serum concentration of IL-6 is <3 pg/ml (0.15 pM). Interleukin-6 has been emphasized by reports of elevated circulating as well as intracardiac IL-6 levels in patients with congestive heart failure (MacGowan G A, Mann D L, Kormos R L, et al. Circulating interleukin-6 in severe heart failure. Am J Cardiol 1997; 79: 1128-31.). In addition, IL-6 has been diagnostic of stroke (Kim J S et al., Serial measurement of interleukin-6, transforming growth factor-beta, and S-100 protein in patients with acute stroke. Stroke. 1996 September; 27(9):1553-7.).

Tumor necrosis factor alpha (TNF-alpha) is a protein of 185 amino acids glycosylated at positions 73 and 172. It is synthesized as a precursor protein of 212 amino acids. Monocytes express at least five different molecular forms of TNF-alpha with molecular masses of 21.5-28 kDa. They mainly differ by post-translational alterations such as glycosylation and phosphorylation. TNF-alpha is produced by many different cell types. The main sources in vivo are stimulated monocytes, fibroblasts, and endothelial cells. Macrophages, T-cells and B-lymphocytes, granulocytes, smooth muscle cells, eosinophils, chondrocytes, osteoblasts, mast cells, glial cells, and keratinocytes also produce TNF-alpha after stimulation. Glioblastoma cells constitutively produce TNF-alpha and the factor can be detected also in the cerebrospinal fluid. Human milk also contains TNF-alpha. The normal serum concentration of TNF-alpha is <40 pg/ml (2 pM). Elevations in the plasma concentration of TNF-alpha are associated with any proinflammatory condition, including trauma, stroke, and infection. TNF.alpha. has a half-life of approximately 1 hour in the bloodstream, indicating that it may be removed from the circulation soon after symptom onset. A rapid overproduction of TNF-alpha in a cerebral post-ischemic inflammatory response leads to the stimulation of adhesive molecules expression with subsequent accumulation of leukocytes in the ischemic focus, which is preceded by their adhesion and migration. The TNF-alpha proinflammatory activity results mainly in extending the area of the brain infarct, which brings about negative clinical implications. Being the final morphological effect of ischemic stroke, TNF-alpha appears also to contribute to neuronal necrosis by its involvement in the process of apoptosis as well as in the death of neurons.

Intercellular adhesion molecule (sICAM-1), also called CD54, is an 85-110 kDa Ig-like cell adhesion molecule expressed by several cell types, including leukocytes and endothelial cells. It can be induced in a cell-specific manner by several cytokines, for example, tumor necrosis factor-alpha, interleukin-1, and interferon-gamma, and inhibited by glucocorticoids. The normal plasma concentration of ICAM-1 is approximately 250 ng/ml (2.9 nM). ICAM-1 plays a role in inflammatory processes and in the T-cell mediated host defense system. It functions as a costimulatory molecule on antigen-presenting cells to activate MHC class II restricted T-cells, and on other cell types in association with MHC class I to activate cytotoxic T-cells. ICAM-1 on endothelium plays an important role in migration of (activated) leukocytes to sites of inflammation. ICAM-1 is shed by the cell and detected in plasma as sICAM-1. Derangement of ICAM-1 expression probably contributes to the clinical manifestations of a variety of diseases, predominantly by interfering with normal immune function. Among these are malignancies (e.g., melanoma and lymphomas), many inflammatory disorders (e.g., asthma and autoimmune disorders), atherosclerosis, ischemia, certain neurological disorders, and allogeneic organ transplantation (O'Malley T, Ludlam C A, Riemermsa R A, Fox K A. Early increase in levels of soluble inter-cellular adhesion molecule-1 (sICAM-1); potential risk factor for the acute coronary syndromes. Eur Heart J. 2001 July; 22(14):1226-34.).

VCAM-1 (vascular cell adhesion molecule-1), or CD106, contains six or seven immunoglobulin domains and is expressed on both large and small vessels only after the endothelial cells are stimulated by cytokines. The sustained expression of VCAM-1 lasts over 24 hours. Primarily, VCAM-1 is an endothelial ligand for VLA-4 (Very Late Antigen-1 or alpha4beta1) of the beta 1 subfamily of integrins and for integrin alpha4beta7. VCAM-1 promotes the adhesion of lymphocytes, monocytes, eosinophils, and basophils. Interestingly, certain melanoma cells can use VCAM-1 to adhere to the endothelium, and VCAM-1 may participate in monocyte recruitment to atherosclerotic sites. The normal serum concentration of sVCAM is approximately 650 ng/ml (6.5 nM). VCAM levels are elevated in MI and with unstable angina. Endothelial VCAM of inflammatory response appear within hours of the initial ACS event and remain elevated for up to 6 months at levels that may reflect the progression of the inflammatory process. Increased level of VCAM, drawn during presentation of ACS, was a significant predictor of recurrent ischemia, nonfatal MI, and cardiac death 6 months after the initial event (P<0.001) (Mulvihill N, Foley J B, Murphy R T, Curtin R, Crean P A, Walsh M. 2001. Risk stratification in unstable angina and non-Q wave myocardial infarction using soluble cell adhesion molecules. Heart 85(6):623-7.). Mulvihill reported that although both VCAM and C-reactive protein were elevated in patients with adverse outcomes, VCAM had a higher specificity than C-reactive protein (69% versus 52%, respectively).

Human macrophage chemoattractant protein-1 (MCP-1) also called human macrophage/monocyte chemotactic and activating factor (MCAF). MCP-1 is an 8.5 kDa protein containing 76 amino acid residues. It plays an important role in the inflammatory response of blood monocytes and tissue macrophages. Studies have revealed that MCAF/MCP-1 has in vitro multiple functions against monocytes/macrophages. MCAF/MCP-1 induces intracellular calcium influx, respiratory burst, expression of adhesion molecules such as Beta 2 integrins, and release of lysosomal enzymes in monocytes as IL-8 does against neutrophils. Moreover, MCAF/MCP-1 induces monocytes to produce tissue factor and pro-inflammatory cytokines such as IL-1 and IL-6, and enhances the tumoricidal activity of monocytes against several types of cancer cells. In addition to these effects on monocytes/macrophages, MCAF/MCP-1 induces chemotaxis, release of histamine and leukotriene, and intracellular calcium influx in basophils. Moreover, MCAF/MCP-1 chemoattracts both CD4+ and CD8+ T lymphocytes and augments the avidity of VLA-4 and VLA-5 on T lymphocytes. In addition to MCP-1, several other CC chemokines have been found to be associated with advanced atherosclerotic lesions: MIP-1alpha and MIP-1beta are expressed by T-cells in human plaques [J. N. Wilcox, N. A. Nelken, S. R. Coughlin, D. Gordon and T. J. Schall, Local expression of inflammatory cytokines in human atherosclerotic plaques. *J. Atheroscler. Thromb.* 1 Suppl 1 (1994), pp. S3-S10.] and the number of T-cells expressing these chemokines correlates with the total number of T-cells found in the plaques. RANTES is also expressed by lesion T-cells but in a smaller population (about 5%). MCP4 is expressed in advanced plaques by endothelial cells of the vasa vasorum and in lesional macrophages [J. M. Pattison, P. J. Nelson, P. Huie, R. K. Sibley and A. M. Krensky, RANTES chemokine expression in transplant-associated accelerated atherosclerosis. *J. Heart Lung Transplant* 15 (1996), pp. 1194-1199.]. It has also been recently found that two lymphocyte specific chemoattractants, PARC/DC-CK1 and ELC, are highly expressed in human atherosclerotic plaques, PARC exclusively by macrophages and ELC by macrophages and SMC [T. J. Reape, K. Rayner, C. D. Manning, A. N. Gee, M. S. Barnette, K. G. Burnand and P. H. E. Groot, Expression and cellular localisation of the CC chemokines PARC and ELC in human atherocerotic plaques. *Am. J. Pathol.* 154 (1999), pp. 365-374.]. In contrast to its expression pattern in atherosclerotic plaques, RANTES is highly expressed in human transplant-associated accelerated atherosclerosis by macrophages, lymphocytes, myofibroblasts and endothelial cells. MCP-1 levels have been seen to be elevated in stroke (Kim J S. Cytokines and adhesion molecules in stroke and related diseases. J Neurol Sci. 1996 May; 137(2):69-78).

Macrophage migration inhibitory factor is considered to be a pleiotropic cytokine but, in contrast to other cytokines, it not only has regulatory functions but also at least two enzymatic activities (T. Calandra and T. Roger, Macrophage migration inhibitory factor a regulator of innate immunity, *Nat Rev Immunol* 3(2003), pp. 791-800.). It has a homotrimeric structure and is expressed by a range of leukocytes, including monocytes, macrophages, neutrophils, and mast cells, and also by endocrine organs involved in stress response, such as the hypothalamus and adrenal glands (H. Lue, R. Kleemann and T Calandra et al., Macrophage migration inhibitory factor (MIF) mechanisms of action and role in disease, *Microbes Infect* 4(2002), pp. 449-460.; and G. Fingerle-Rowson, P. Koch and R Bikoff et al., Regulation of macrophage migration inhibitory factor expression by glucocorticoids in vivo, *Am J Pathol* 162 (2003), pp. 47-56.). Under physiological circumstances, macrophage migration inhibitory factor is thought to regulate host responses to infection and stress. Consistent with this hypothesis, macrophage migration inhibitory factor was found to upregulate the expression of toll-like receptor 4 by macrophages (T. Roger, J. David, M. P. Glauser and T. Calandra, MIF regulates innate immune responses through modulation of Toll-like receptor 4, *Nature* 414 (2001), pp. 920-924.) and to counterbalance the immunosuppressive effects of glucocorticoids by modulating intracellular proinflammatory pathways (L. Leng, C. N. Metz and Y Fang et al., MIF signal transduction initiated by binding to CD74, *J Exp Med* 197 (2003), pp. 1467-1476. and R. A. Mitchell, C. N. Metz, T. Peng and R. Bucala, Sustained mitogen-activated protein kinase (MAPK) and cytoplasmic phospholipase A2 activation by macrophage migration inhibitory factor (MIF) Regulatory role in cell proliferation and glucocorticoid action, *J Biol Chem* 274 (1999), pp. 18100-18106.). Macrophage migration inhibitory factor is involved in pathophysiological inflammation-mediated conditions such as sepsis, arthritis, bronchial asthma, renal transplant rejection, and acute respiratory distress syndrome (L. E. Lehmann, U. Novender and S Schroeder et al., Plasma levels of macrophage migration inhibitory factor are elevated in patients with severe sepsis, *Intensive Care Med* 27 (2001), pp. 1412-1415; C. Meazza, P. Travaglino and P Pignatti et al., Macrophage migration inhibitory factor in patients with juvenile idiopathic arthritis, *Arthritis Rheum* 46 (2002), pp. 232-237, E. Yamaguchi, J. Nishihira and T Shimizu et al., Macrophage migration inhibitory factor (MIF) in bronchial asthma, *Clin Exp Allergy* 30 (2000), pp. 1244-1249.; H. Y. Lan, N. Yang and F. G Brown et al., Macrophage migration inhibitory factor expression in human renal allograft rejection, *Transplantation* 66 (1998), pp. 1465-1471.; and S. C. Donnelly, C. Hasleft and P. T Reid et al., Regulatory role for macrophage migration inhibitory factor in acute respiratory distress syndrome, *Nat Med* 3(1997), pp. 320-323.). In addition, it is thought to be involved in atherosclerosis because it induces expression of intercellular adhesion molecule 1 by vascular endothelial cells, and, interestingly, upregulation of macrophage migration inhibitory factor was closely associated with adhesion of monocytes to the endothelium and subsequent migration into the subendothelial space. Inhibition of macrophage migration inhibitory factor resulted in a shift in the cellular composition of neointimal atherosclerotic plaques toward a more stabilized phenotype, possibly resulting from a reduction of monocyte recruitment (A. Schober, J. Bernhagen and M Thiele et al., Stabilization of atherosclerotic plaques by blockade of macrophage migration inhibitory factor after vascular injury in apolipoprotein E-deficient mice, *Circulation* 109 (2004), pp. 380-385.). Boekholdt et al. (Boekholdt et al, Macrophage migration inhibitory factor and the risk of myocardial infarction or death due to coronary artery disease in adults without prior myocardial infarction or stroke: the EPIC-Norfolk Prospective Population study. Am J. Med. 2004 Sep. 15; 117(6):390-7) showed that the relation between macrophage migration inhibitory factor and the risk of myocardial infarction or death due to coronary artery disease in adults without a history of myocardial infarction or stroke is not very strong. However, the data support a regulatory role for macrophage migration inhibitory factor in the process of atherosclerosis.

Hemoglobin (Hb) is an oxygen-carrying iron-containing globular protein found in erythrocytes. Hb is responsible for carrying oxygen to cells throughout the body.

Human lipocalin-type prostaglandin D synthase (hPDGS), is a 30 kDa glycoprotein that is a type of Prostaglandin (PG) D synthase. From Patent No. EP0999447A1, the upper limit of hPDGS concentrations in apparently healthy individuals is reported to be approximately 420 ng/ml, and from the same patent Elevations of hPDGS have been identified in blood from patients with unstable angina, cerebral infarction and is likely to be a useful marker of ischemic episodes. Patent No. EP0999447A1 also suggests that the hPGDS concentration decreases as ischemia is resolved.

Mast cell tryptase is a serine protease tryptase is the major protein component of human mast cell secretory granules, where it exists in a complex with heparin proteoglycan. Both heparin and tryptase are found only in mast cell granules and are tightly bound to one another under physiologic conditions [L. B. Schwartz and T. R. Bradford, Regulation of tryptase from human lung mast cells by heparin. *J. Biol. Chem.* 261 (1986), pp. 7372-7379.]. Elevated serum tryptase levels (>1 ng/mL) between 1 and 6 hours after an event provides a specific indication of mast cell degranulation.

KL-6 is a mucin-like glycoprotein expressed on type II pneumocytes. Circulating levels of KL-6 have diagnostic and prognostic significance in a number of interstitial lung diseases, and when elevated are thought to indicate disruption of the alveolar epithelial lining. KL-6 has been shown to be elevated in patients with acute respiratory distress syndrome (Sato H et al., KL-6 levels are elevated in plasma from patients with acute respiratory distress syndrome. Eur Respir J. 2004 January; 23(1):142-5.).

IL-10 is an 18.7-kd protein expressed by a variety of human immune cells, including both T H1 and T H2 cells, B cells, monocytes-macrophages, dendritic cells, mast cells, and eosinophils. In mouse models IL-10 has been associated with inflammatory arthritis, [E. Quattrocchi, M. J. Dallman, A. P. Dhillon, A. Quaglia, G. Bagnato and M. Feldmann, Murine IL-10 gene transfer inhibits established collagen-induced arthritis and reduces adenovirus-mediated inflammatory responses in mouse liver. *J Immunol* 166 (2001), pp. 5970-5978.] and allergic inflammation. [K. G. Tournoy, J. C. Kips and R. A. Pauwels, Endogenous interleukin-10 suppresses allergen-induced airway inflammation and nonspecific airway responsiveness. *Clin Exp Allergy* 30 (2000), pp. 775-783] IL-10 has a number of documented antiallergic properties that might be important to immunotherapy (I. Bellinghausen, J. Knop and J. Saloga, The role of interleukin 10 in the regulation of allergic immune responses. *Int Arch Allergy Immunol* 126 (2001), pp. 97-101). These include inhibition of human eosinophil cytokine production and survival. [S. Takanaski, R. Nonaka, Z. Xing, P. O'Byrne, J. Dolovich and M. Jordana, Interleukin 10 inhibits lipopolysaccharide-induced survival and cytokine production by human peripheral blood eosinophils. *J Exp Med* 180 (1994), pp. 711-715.]. Il-10 has been shown to be associated with the early clinical course of patients with acute ischemic stroke, especially in patients with small vessel disease or subcortical infarctions (Vila N, Castillo J, Davalos A, Esteve A, Planas A M, Chamorro A Levels of anti-inflammatory cytokines and neurological worsening in acute ischemic stroke. Stroke. 2003 March; 34(3):671-5), with hemhorrage (Dziedzic T, Bartus S, Klimkowicz A, Motyl M, Slowik A, Szczudlik A. Intracerebral hemorrhage triggers interleukin-6 and interleukin-10 release in blood. Stroke. 2002 September; 33(9):2334-5.) and stroke (Tarkowski A. Intrathecal release of pro- and anti-inflammatory cytokines during stroke. Clin Exp Immunol. 1997 December; 110(3):492-9.).

Markers Specifically Related to Neural Tissue Injury

Adenylate kinase-1 (AK1) is an isoform of the enzyme that catalyzes the interconversion of ATP and AMP to ADP. AK1 is found in brain, skeletal muscle, heart, and aorta. The normal serum AK concentration is <5 units/liter. Serum AK1 seems to have the greatest specificity of the four known AK isoforms as a marker of neural tissue injury.

Neurotrophins are a family of growth factors expressed in the mammalian nervous system. Some examples of neurotrophins include nerve growth factor (NGF), brain-derived neurotrophic factor (BDNF), ciliary neurotrophic factor (CNTF), basic fibroblast growth factor (bFGF) and glial derived neurotrophic factor (GDNF), neurotrophin-4/5 (NT-4/5), NT-6, and neurotrophin-3 (NT-3). These neurotrophins have also been found to be expressed in a variety of non- neuronal tissues such as cardiovascular, immune, endocrine and reproductive systems.

Brain-derived neurotrophic factor (BDNF) is a 27-kDa polypeptide that is recognized as playing an important role in the survival, differentiation, and outgrowth of select peripheral and central neurons during development and in adulthood [E. J. Huang and L. F. Reichardt, Neurotrophins: roles in neuronal development and function. *Annu. Rev. Neurosci.* 24 (2001), pp. 677-736.]. It is well known that BDNF participates in use-dependent plasticity mechanisms such as long-term potentiation, learning, and memory [A. F. Schinder and M. Poo, The neurotrophin hypothesis for synaptic plasticity. *Trends Neurosci.* 23 (2000), pp. 639-645.]. Recently, it has been demonstrated that activation of the TrkB/phosphatidylinositol 3-kinase (PI3-K)/Akt signaling pathway by BDNF in the hippocampus is important for spatial memory M. Mizuno, K. Yamada, N. Takei, M. H. Tran, J. He, A. Nakajima, H. Nawa and T. Nabeshima, Phosphatidylinositol 3-kinase: a molecule mediating BDNF-dependent spatial memory formation. *Mol. Psychiatry* 8(2003), pp. 217-224.]. BDNF has been associated with the mechanism of infarct tolerance (Yanamoto H, et al., Infarct tolerance induced by intra-cerebral infusion of recombinant brain-derived neurotrophic factor. Brain Res. 2000 March 24;859(2):240-8.).

NT-3 is a growth factor involved in the maintenance and survival of peripheral neuronal cells. After axotomy and during peripheral nerve regeneration, the neurotrophins NGF, NT-3 and BDNF show a well defined and selective beneficial effect on the survival and phenotypic expression of primary sensory neurons in dorsal root ganglia and of motoneurons in spinal cord. Other neurotrophic factors such as CNTF, GDNF and LIF also exert a variety of actions on neuronal cells, which appear to overlap and complement those of the neurotrophins. In addition, there is an indirect contribution of GGF to nerve regeneration. GGF is produced by neurons and stimulates proliferation of Schwann cells, underlining the close interaction between neuronal and glial cells during peripheral nerve regeneration [Terenghi G. Peripheral nerve regeneration and neurotrophic factors. J Anat. 1999 January; 194 (Pt 1):1-14].

Calbindin-D is a 28 kDa facilitator of the vitamin D dependent movement of calcium through the intestinal or renal cell. Calbindin also has a major role in neuronal cells, in HEK renal cells, in pancreatic cells as well as in bone cells in protecting against apoptotic cell death. The normal serum concentration of calbindin-D is <20 pg/ml, however, maximum serum calbindin-D concentrations following cardiac arrest can be as much as 700 pg/ml. Direct evidence for a protective role of calbindin-D has been demonstrated in studies in cells in which the calbindin gene has been transfected [Q. Guo, S. Christakos, N. Robinson and M. P. Mattson, Calbindin-D-28k blocks the proapoptotic actions of mutant presenilin 1: reduced oxidative stress and preserved mitochondrial function. *Proc. Natl. Acad. Sci. USA* 95 (1998), pp. 3227-3232.].

Creatine Kinase is a transferase that catalyzes formation of phosphocreatine from ATP+creatine. The reaction stores ATP energy as phosphocreatine. Three cytoplasmic isoenzymes have been identified in human tissues: MM from skeletal muscle, MB from myocardial tissue, and BB from nervous tissue as well as a mitochondrial isoenzyme. When the total CPK level is substantially elevated, it usually indicates injury or stress to one or more of these areas. CK-MB levels have been shown to be elevated in stroke (Norris J W et al., Serum cardiac enzymes in stroke. Stroke. 1979 September-October; 10(5):548-53.) and stroke subtype (Mayer et al., Myocardial injury and left ventricular performance after subarachnoid hemorrhage. Stroke. 1999 April; 30(4):780-6.) CK-BB levels have been shown to be elevated in stroke (Matias-Guiu J et al. Myelin basic protein and creatine kinase BB isoenzyme as CSF markers of intracranial tumors and stroke. Acta Neurol Scand. 1986 May; 73(5):461-5.), stroke subtype (Kloss R. et al. Creatine kinase BB activity in the serum of patients with cerebrovascular diseases Nervenarzt. 1985 August; 56(8): 417-22.) and severity (Creatine kinase BB activity in serum of patients with acute stroke: correlation with the severity of brain damage. Ital J Neurol Sci. 1987 December;8(6):567-70.) The normal serum concentration of CK-BB is <10 ng/ml (120 pM). CK-BB has a half-life of 1-5 hours in serum and in severe stroke, serum concentrations CK-BB are elevated and peak soon after the onset of stroke (within 24 hours), gradually returning to normal after 3-7 days. CK-BB concentrations in the serum of individuals with head injury peak soon after injury and return to normal between 3.5-12 hours after injury, depending on the injury severity (Skogseid, I. M. et al., Acta Neurochir. (Wien.) 115:106-111,1992). Maximum serum CK-BB concentrations can exceed 250 ng/ml (3 nM).

Glial fibrillary acidic protein (GFAP) is the major intermediate filament protein of the astrocyte, and body fluid levels of GFAP are an important tool for estimating astrogliosis and astrocytic activation in vivo. GFAP is coded on chromosome 17q21.1-q25 and consists of 432 amino acids (Reeves et al., 1989). The corresponding molecular mass is 49.8 kDa. Cytoskeletal GFAP is tightly packed into polymers. After break-up of the GFAP polymer, a soluble fragment of GFAP of approximately 41 kDa is released into the adjacent fluid compartments (Eng and Ghirnikar, 1994). Elevations of GFAP in serum can be attributed to neural tissue injury due to ischemia, coupled with increased permeability of the blood brain barrier. GFAP has been shown to be elevated in the CSF (Aurell A. et al., Determination of S-100 and glial fibrillary acidic protein concentrations in cerebrospinal fluid after brain infarction. Stroke. 1991 October; 22(10):1254-8) and serum (Niebroj-Dobosz I. et al., Immunochemical analysis of some proteins in cerebrospinal fluid and serum of patients with ischemic strokes. Folia Neuropathol. 1994;32(3):129-37.; Release of glial tissue- specific proteins after acute stroke: A comparative analysis of serum concentrations of protein S-100B and glial fibrillary acidic protein. Stroke. 2000 November; 31(11):2670-7.) of patients with stroke and stroke subtype (Runnerstam M et al., Extracellular glial fibrillary acidic protein and amino acids in brain regions of patients with subarachnoid hemorrhage—correlation with level of consciousness and site of bleeding. Neurol Res. 1997 August; 19(4):361-8.).

Lactate dehydrogenase (LDH) is a 135 kDa tetrameric enzyme that, along with the coenzyme NAD+, catalyzes the interconversion of lactate and pyruvate. In vertebrates, genes for three different subunits (LDH-A, LDH-B and LDH-C) exist. LDH found in many body tissues, especially the heart, liver, kidney, skeletal muscle, brain, blood cells and lungs. LDH can be used for for the retrospective diagnosis of myocardial infarction, though Cardiac Troponin I and T have superior sensitivity and specificity. The normal serum LDH concentration is <600 units/liter (Ray, P. et al., Cancer Detect. Prev. 22:293-304, 1998). Elevations of LDH have been reported to differentiate between ischemic stroke and TIA (Lampl Y et al., Cerebrospinal fluid lactate dehydrogenase levels in early stroke and transient ischemic attacks. Stroke. 1990 June; 21(6):854-7.) and acute stroke (Ruzak-Skocir B, Trbojevic-Cepe M. Study of serum and cerebrospinal fluid enzymes in diagnosis and differential diagnosis of cerebrovascular diseases. Neurologija. 1990;39(4):239-50.).

Myelin basic protein (MBP) is one of two major protein components of CNS myelin. MBP usually refers to the 'classic' 18.5 kDa isoform, which is one of the most abundant proteins of the myelin sheath of the adult human and bovine CNS. However, the 18.5 kDa MBP isoform is only part of a family of developmentally expressed, translocatable, and highly post-translationally modified proteins, with a multiplicity of binding partners. Since 18.5 kDa MBP's primary role has long been accepted to be stabilising the myelin sheath. Myelin formation and maintenance requires complex interactions between neurons and glia, and between the integral protein and lipid components of the myelin sheath. The normal serum concentration of MBP is <7 ng/ml (400 pM). Serum MBP is elevated after all types of severe stroke, and is correlated with the level of damage (Cerebrospinal fluid membrane-bound tissue factor and myelin basic protein in the course of vasospasm after subarachnoid hemorrhage. Hirashima Y et al., Neurol Res. 2001 October; 23(7):715-20.), while elevations in MBP concentration are not reported in the serum of individuals with strokes of minor to moderate severity, which would include lacunar infarcts or transient ischemic attacks (Palfreyman, J. W. et al., Clin. Chim. Acta 92:403409, 1979). Normal levels of MBP in serum have an upper limit of 7 ng/ml (400 pM), but depending upon the severity of damage, exceed 120 ng/ml (6.9 nM). Due to the correlation between severity of damage and the release of MBP (Strand T. et al., Brain and plasma proteins in spinal fluid as markers for brain damage and severity of stroke. Stroke. 1984 January-February; 15(1):138-44.), stroke severity will affect the release kinetics by changing the length of time that MBP is elevated in the serum. Serum MBP elevates on the order or 1-3 hours after stroke onset, plateauing its concentration 2-5 days following stroke onset, and then decreases to normal levels over 7-9 days.

Neural cell adhesion molecule (NCAM), also called CD56, is a 170 kDa member of a family of cell surface sialoglycoproteins mediating homotypic and heterotypic cell-cell interactions. Neural cell adhesion molecules NCAM and L1 to regulate axon growth, guidance, and synaptic plasticity. Recent research findings suggest (Panicker et al., Cellular signalling mechanisms of neural cell adhesion molecules. Front Biosci. 2003 May 1;8:d900-11.) that these molecules signal in part through integrins leading to cytoskeletal rearrangements locally in the growth cone or cell leading edge, and are expressed on the surface of astrocytes, oligodendrocytes, Schwann cells, neurons, and axons. Normal serum concentration of NCAM is <20 units/ml. NCAM has been reported as a marker for hypoxic-ischemic damage (Karkela J, et al., CSF and serum brain-specific creatine kinase isoenzyme (CK-BB), neuron-specific enolase (NSE) and neural cell adhesion molecule (NCAM) as prognostic markers for hypoxic brain injury after cardiac arrest in man. J Neurol Sci. 1993 May; 1 16(1):100-9.).

Neuron specific enolase (NSE) is the gamma gamma isoform of the five isozymes of the glycolytic enzyme, enolase. This enzyme is released into the CSF when neural tissue is injured. Neoplasms derived from neural or neuroendocrine tissue may release NSE into the blood. The normal serum concentration of NSE is <12.5 ng/ml (160 pM). Serum NSE has a half-life of approximately 20 hours. NSE has been reported to be elevated in the blood from patients suffering from ischemic stroke (Fassbender et al., Leakage of brain-originated proteins in peripheral blood: temporal profile and diagnostic value in early ischemic stroke. J Neurol Sci. 1997 May 1;148(1):101-5.), infarction volume and prognosis (Missler U et al., S-1 00 protein and neuron-specific enolase concentrations in blood as indicators of infarction volume and prognosis in acute ischemic stroke. Stroke. 1997 October; 28(10):1956-60), and neural damage (Cunningham et al., Serum neurone specific enolase (NSE) levels as an indicator of neuronal damage in patients with cerebral infarction. Eur J Clin Invest. 1991 October; 21 (5):497-500.). Serum NSE is elevated after 4 hours from stroke onset, with concentrations reaching a maximum 1-3 days after onset. After the serum concentration reaches its maximum, which can exceed 300 ng/ml (3.9 nM), levels of serum NSE gradually decrease to normal concentrations over approximately one week. Like MBP, NSE will be present in the serum for a longer period of time as the severity of injury increases.

The proteolipid protein gene products DM-20 and PLP are adhesive intrinsic membrane proteins that make up 50% of the protein in myelin and serve to stabilize compact myelin sheaths at the extracellular surfaces of apposed membrane lamellae. Proteolipid protein (PLP) is a 30 kDa insertion isoform of DM-20, and is a polytopic integral membrane protein that act to stabilize appositions of the extracellular surfaces of the myelin membrane. The normal serum concentration of PLP is <9 ng/ml (300 pM).

Thrombomodulin is an anticoagulant glycoprotein that is expressed on the surface of vascular endothelial cells and epidermal keratinocytes. As its name implies, thrombomodulin functions to modulate the activity of the hemostatic protease thrombin. In endothelium, thrombomodulin inhibits thrombin's procoagulant effects while markedly enhancing thrombin-dependent activation of anticoagulant protein C. Thrombomodulin also promotes thrombin-dependent activation of thrombin-activatable fibrinolysis inhibitor (TAFI), a carboxypeptidase that inhibits activation of plasminogen in fibrin clots. Although thrombomodulin was originally identified as an endothelial protein, it is also expressed by epidermal keratinocytes and some other types of cells. Keratinocyte thrombomodulin is able to bind to thrombin and promote activation of protein C.

Protein kinase C molecules regulate both positive and negative signal transduction pathways essential for the initiation and homeostasis of immune responses. There are multiple isoforms of protein kinase C that are activated differently by calcium and diacylglycerol, and these are activated mainly by antigen receptors in T cells, B cells and mast cells, including the gamma isoform, which is specific for CNS tissue but not found in general as a marker in the blood. PKCd, PKCa, and ratios of PKCd and PKCa isoforms may be useful in identifying the presence and progression of cerebral vasospasm following subarachnoid hemorrhage. The beta and beta II isoforms have been shown to be elevated in tissue from ischemic stroke patients (Krupinski J et al., Protein kinase C expression and activity in the human brain after ischaemic stroke. Acta Neurobiol Exp (Wars). 1998;58(1):13-21.).

Additional Markers that are Non-Specific for Cellular Injury

Human vascular endothelial growth factor (VEGF) is a key player of angiogenesis in health and disease. VEGF binds the receptor tyrosine kinases VEGFR-1 (Flt-1) and VEGFR-2 (KDR/Flk-1). Numerous studies indicate that VEGFR-2 transmits critical angiogenic signals in response to VEGF (Ferrara N. 2001. Role of vascular endothelial growth factor in regulation of physiological angiogenesis. Am J Physiol Cell Physiol 280:C1358-1366.). Alternative splicing of the VEGFgene gives rise to several VEGF isoforms with molecular masses of 121, 145, 165 or 189 kDa. Translation of these VEGF isoforms is initiated at a classical AUG start codon. Translation initiation at an additional CUG codon, in frame with the AUG start codon, generates a much larger VEGF form (L-VEGF). As proteolytic processing of L-VEGF generates a C-terminal fragment, identical to the secreted AUG-initiated isoforms, L-VEGF might constitute an intracellular store of VEGF. Neuropilin-1 (NP-1) is a specific receptor for the VEGF165 isoform and a co-receptor of VEGFR-2. (Soker S, Takashima S, Miao HQ, Neufeld G, Klagsbrun M. 1998. Neuropilin-1 is expressed by endothelial and tumor cells as an isoformspecific receptor for vascular endothelial growth factor. Cell 92:735-745.) NP-1 also binds semaphorin3A (Sema3A), a neurorepellant implicated in guidance of axons. Neuropilin-2 (NP-2) binds VEGF165 and VEGF145, as well as Sema3C and Sema3F. The fact that NP-1 and NP-2 bind semaphorins and VEGF suggests that these receptors have roles in both the nervous and cardiovascular system. The expression of VEGF predict the onset of cerebral vasospasm after aneurysmal subarachnoid hemorrhage (McGirt et al. Serum von Willebrand factor, matrix metalloproteinase-9, and vascular endothelial growth factor levels predict the onset of cerebral vasospasm after aneurysmal subarachnoid hemorrhage. Neurosurgery. 2002 November;51(5):1128-34; discussion 1134-5.), acute ischemic stroke (Slevin M et al., Activation of MAP kinase (ERK-1/ERK-2), tyrosine kinase and VEGF in the human brain following acute ischaemic stroke. Neuroreport. 2000 August. 21;11(12):2759-64.) and hemorrhage (Cheng S Y et al., Intracerebral tumor-associated hemorrhage caused by overexpression of the vascular endothelial growth factor isoforms VEGF121 and VEGF165 but not VEGF189. Proc Natl Acad Sci USA. 1997 Oct. 28;94(22): 12081-7.).

Insulin-like growth factor-1 (IGF-1) is a 7.5 kDa single-chain polypeptide of 70 amino acids. It is a trophic factor that circulates at high levels in the blood-stream and mediates many, if not most, of the effects of growth hormone. Although the main source of IGF-1 in the serum is the liver, many other tissues synthesize it and are sensitive to its trophic action. IGF-1 was called somatomedin in the older literature. IGF-1 and insulin have similar three-dimensional structures. IGF-1 appears to influence neuronal structure and functions throughout the life span. It has been shown to have the ability to preserve nerve cell function and promote nerve growth in experimental studies. The normal serum concentration of IGF-1 is approximately 160 ng/ml (21.3 nM). IGF-I and IGFBP-3 plasma levels were shown to be decreased in patients after cerebral ischemia. After acute ischemic stroke, increased demand for growth factors, altered tissue distribution, and accelerated metabolic clearance rate or central inhibition of the somatotrophic axis may contribute to these low plasma concentrations (Schwab S et al., Plasma insulin-like growth factor I and IGF binding protein 3 levels in patients with acute cerebral ischemic injury. Stroke. 1997 September; 28(9):1744-8.).

Adhesion molecules are involved in the inflammatory response to injury. Examples of such adhesion molecules include E-selectin, intercellular adhesion molecule-1, vascular cell adhesion molecule, and other similar molecules.

E-selectin, also called ELAM-1 and CD62E, is a 140 kDa cell surface C-type lectin expressed on inflamed endothelial cells in response to treatment with inflammatory cytokines Bevilacqua et al., 1989). Intravital microscopic experiments have shown that its function in mediating leukocyte rolling is largely redundant with that of P-selectin (Hickey et al., 1999; Bullard et al., 1996; Kunkel and Ley, 1996). Some reports show elevated E-selectin levels following stroke (Stanimirovic D et al., Increase in surface expression of ICAM-1, VCAM-1 and E-selectin in human cerebromicrovascular endothelial cells subjected to ischemia-like insults. Acta Neurochir Suppl. 1997;70:12-6.) while others show no difference (Serum levels of intercellular adhesion molecule-1 and E-selectin in patients with acute ischaemic stroke. J Neurol. 1997 February; 244(2):90-3.).

The 11 amino acid, 1142 Da neuropeptide head activator (HA) stimulates cell proliferation of neuronal precursor and neuroendocrine cells. The mitogenic signaling cascade requires Ca(2+) influx for which, the growth-factor-regulated Ca(2+)-permeable cation channel, GRC, is responsible. While no studies have yet reported an association of HA as a stroke-specific marker, the usage of HA as a marker would be to identify patients with tumors originating in neural tissue, as serum HA levels have been seen elevated in patients with such tumors (Winnikes M, Schaller H C, Sachsenheimer W. Head activator as a potential serum marker for brain tumour analysis. Eur J Cancer. 1992;28(2-3):421-4.).

Markers Specifically Related to Apoptosis

Apoptosis is one of the main types of programmed cell death (PCD). As such, it is a process of deliberate suicide by an unwanted cell in a multicellular organism. In contrast to necrosis, which is a form of cell death that results from acute tissue injury, apoptosis is carried out in an ordered process that generally confers advantages during an organism's life cycle. We now introduce several markers related to apoptosis, however, this list is not meant to be limiting.

Caspases are a family of cysteine proteases that cleave proteins after aspartic acid residues. They are the main effectors of apoptosis or programmed cell death (PCD) and their activation leads to characteristic morphological changes of the cell such as shrinkage, chromatin condensation, DNA fragmentation and plasma membrane blebbing. Induction to commit suicide is required for proper organismal development, to remove cells that pose a threat to the organism (e.g. cell infected with virus, cancer cells), and to remove cells that have damaged DNA. Cells undergoing apoptosis are eventually removed by phagocytosis.

Initiator caspases are the first to be activated and include caspase-2, 8, 9 and 10. These cleave and activate the effector caspases (3, 6, 7), which cleave, degrade or activate other cellular proteins. Some caspases (1, 4, 5, 11, 12, 13, 14) have a specialized role in inflammation and their activation leads to the processing of pro-inflammatory cytokines.

Caspase activation can be mediated by intrinsic factors such as Bcl-2 on the mitochondrial membrane. Bcl-2 is normally found associated with Apaf-1. Damage causes Bcl-2 to disassociate from Apaf-1 leading to the release of cytochrome c into the cytosol. A new complex forms which is comprised of cytochrome c, Apaf-1, and caspase-9 (the apoptosome). Caspases-9 is cleaved and activates other caspases leading to an expanding cascade of proteolytic activity within the cell. This eventually results in the digestion of structural proteins in the cytoplasm, chromosomal DNA degradation and phagocytosis of the cell. External signals can also effect a caspase activation cascade. TNF and Fas receptors on the cell surface can be triggered upon ligand binding (TNF, Fas, certain toxins and chemicals) to cleave caspase-8 which then goes on to initiate increased proteolysis within the cell and its ultimate removal by phagocytosis. Ultimate activation of the caspase signaling pathway will create a cascade of caspase enzymes that will cleave proteins essential for cell survival and lead to apoptosis.

Caspase-3, also called CPP32, apopain, or YAMA has been identified as being a key mediator of apoptosis of mammalian cells. Caspase-3 zymogens exist within the cytosol as inactive dimmers. Consistent with the proposal that apoptosis plays a central role in human neurodegenerative disease, caspase-3 activation has recently been observed in stroke, spinal cord trauma, head injury and Alzheimer's disease. Indeed, peptide-based caspase inhibitors prevent neuronal loss in animal models of head injury and stroke, suggesting that these compounds may be the forerunners of non-peptide small molecules that halt the apoptotic process implicated in these neurodegenerative disorders (Freude B. et al., Apoptosis is initiated by myocardial ischemia and executed during reperfusion. J Mol Cell Cardiol. 2000 February; 32(2):197-208.).

Cathepsin D is a lysosomal acid proteinase which is involved in the malignant progression of breast cancer and other gynecological tumors. Leakage of cathepsins due to the fragility of lysosomal membranes during aging also contributes to neurodegeneration. Levels of cathepsins D and E were significantly increased during normal aging process (H. Nakanishi, et al., Age-related changes in activities and localizations of cathepsins D, E, B, and L in the rat brain tissues. *Exp. Neurol.* 125 (1994), pp. 1-10.). Furthermore, the deficiency of cathepsin D has been recently revealed to provoke a novel type of lysosomal storage disease associated with massive neurodegeneration. Thus this marker could be used to control for the amount of neurodegeneration independent of age in a diagnosis.

Brain alpha spectrin, also called alpha-fodrin, is a 150 kDa neuronal cytoskeleton protein, which has previously been detected in various in vitro and in vivo neuronal injury models. Fodrin is unusual for the presence of a single, proteolytically hypersensitive site in the center of the alpha subunit, which is the favored site of action by many proteases, including the calcium-dependent neutral proteases. This proteolytically hypersensitive site is a unique feature of alpha nonerythroid spectrin since it is absent from human erythrocyte spectrin and appears to be the site at which the molecule is processed in vivo. In addition, on the basis of gel overlay techniques, it appears that the hypersensitive site is also the site at which calmodulin binds to the alpha-subunit in a calcium-dependent manner. These studies thus establish at the molecular level 2 calcium-dependent mechanisms by which brain spectrin function might be regulated. The processing of brain spectrin (fodrin) by calcium-dependent proteases at the postsynaptic membrane has been postulated to be one of the central molecular mechanisms underlying long-term potentiation (LTP).

The N-methyl-D-aspartate (NMDA) subtype of glutamate receptor is a calcium-permeable ligand-gated ion channel that plays an important role in learning and memory. NMDA receptors are heteromeric pentamers or tetramers of NR1 and NR2 receptor subunits that determine the biophysical and pharmacological properties of the receptor. It has been shown that the NR1 subunit contains three transmembrane domains (TM1, TM3, and TM4) and two extracellular domains (S1 and S2), which form the glutamate (or homocysteine) and glycine binding sites, respectively, and a hydrophobic domain (TM2) that forms the pore of the ion channel (B S Meldrum, "The Role of Glutamate in Epilepsy and Other CNS Disorders," Neurology 44S (1994): 14-23.). The NR2 subunit has four further subunits-NR2A, NR2B, NR2C, and NR2D-that are responsible for Na+- and Ca++-permeability regulation. The yellow extracellular loops in the figure are N-terminus fragments of NMDA receptors that are cleaved by thrombin-activated serine proteases during the neurotoxic cascade underlying stroke.

In clinical study, NMDA biomarkers were found to provide real-time evidence of neurotoxicity, with a decrease in levels of circulating NR2A/2B receptor subunits correlating well with reductions in neurotoxic conditions (E I Gusev et al., "Neuroprotective Effects of Glycine for Therapy of Acute Ischaemic Stroke," Cerebrovascular Diseases 10 (2000): 49-60.). These NR2A/2B peptide fragments in human plasma are of molecular weight 2 and 6 kDa, respectively. Subsequent studies have showed a correlation between NR2A/2B levels and TIA and ischemic stroke determination (S A Dambinova, G A Khounteev, and A A Skorometz, "Multiple Panel of Biomarkers for TIA/Stroke Evaluation," Stroke 33 (2002): 1181-1182.). This marker is the subject of United States Patent Application 20030096331, filed Aug. 2, 2001. However, this patent application does not anticipate any other marker besides homocysteine or polyhomocysteine and glutamate or polyglutamate in combination with this marker for diagnosis of stroke or stroke sub-type.

Ubiquitin (Ub) is a small protein that is composed of 76 amino acids. Ub is a heat-stable protein that folds up into a compact globular structure. It is found throughout the cell (thus, giving rise to its name) and can exist either in free form or as part of a complex with other proteins. In the latter case, Ub is attached (conjugated) to proteins through a covalent bond between the glycine at the C- terminal end of Ub and the side chains of lysine on the proteins. Single Ub molecules can be conjugated to the lysine of these proteins, or more commonly, Ub-chains can be attached. Conjugation is a process that depends on the hydrolysis of ATP. Ub is involved in many cell processes. For example, Ub is conjugated to the protein cyclin during the G1 phase of mitosis and thus plays an important role in regulating the cell cycle. Ub conjugation is also involved in DNA repair, embryogenesis, the regulation of transcription, and apoptosis (programmed cell death). The ubiquitin-proteasome pathway (UPP) is a predominantly non-lysosomal protein degradation pathway responsible for degrading many critical regulatory proteins (e.g., nuclear factor-kappa B). This pathway is widely known for its ubiquitous role in immune and inflammatory responses, control of cell growth and apoptosis. These roles are apparent in the nervous system, but neurons and their neighboring cells also employ the UPP for distinct functions, ranging from development to the co-ordination of cellular responses, injury of the nervous system and brain-specific processes such as aging and memory.

Markers Specifically Related to Hemorrhage

Cellular Fibronectin, or ED1+. is an adhesive glycoprotein, is a fibronectin synthesized in endothelial cells. It contains an extra Type III domain (ED1, or EDA/EIIIA), as a result of alternative mRNA splicing. It circulates in the blood in small quantities. Endothelial cells do not express the ED1 domain under normal circumstances, but the ED1 domain is included in fibronectin molecules in pathological conditions (see for instance Dubin D, Peters J H, Brown L F, Logan B, Kent K C, Berse B, Berven S, Cercek B, Sharifi B G, Pratt R E: Balloon catheterization induced arterial expression of embryonic fibronectins. Arterioscler Thromb Vasc Biol. 15:1958 1967, 1995.) Because ED1-fn is not stored in cellular granules, concentration increases indicate increased synthesis (26). Because c-Fn is largely confined to the vascular endothelium, high plasma lvels of this molecule might be indicative of endothelial damage. Plasma c-Fn levels have been reported to be increased in patients with vascular injury secondary to vasculitiis, sepsis, acute major trauma, diabetes, and patients with ischemic stroke (see for instance Peters et al. Elevated plasma levels of ED1+'cellular fibronectin' in patients with vascular injury J Lab Clin Med. 1989. 113:586-597). It has been reported to associate with the hemorrhagic transformation (see for instance Castellanos et al., Plasma Cellular-Fibronectin concentration predicts hemorrhagic transformation after thrombolytic therapy in acute ischemic stroke, Stroke 2004;35:000-000).

How to Measure Various Markers

One of ordinary skill in the art know several methods and devices for the Detect ion and analysis of the markers of the instant invention. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like. For an example of how this procedure is carried out on a machine, one can use the RAMP Biomedical device, called the Clinical Reader sup.™., which uses the fluoresent tag method, though the skilled artisan will know of many different machines and manual protocols to perform the same assay. Diluted whole blood is applied to the sample well. The red blood cells are retained in the sample pad, and the separated plasma migrates along the strip. Fluorescent dyed latex particles bind to the analyte and are immobilized at the detection zone. Additional particles are immobilized at the internal control zone. The fluorescence of the detection and internal control zones are measured on the RAMP Clinical Reader sup.TM., and the ratio between these values is calculated. This ratio is used to determine the analyte concentration by interpolation from a lot-specific standard curve supplied by the manufacturer in each test kit for each assay.

The use of immobilized antibodies specific for the markers is also contemplated by the present invention and is well known by one of ordinary skill in the art. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvagable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constucted using 1, 2, 3, 4, 5, 6, 7, 8, 9, 10, 15, 20, or more or individual markers. The analysis of a single marker or subsets of markers comprising a larger panel of markers could be carried out methods described within the instant invention to optimize clinical sensitivity or specificity in various clinical settings. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, 2.sup.nd edition, Carl Burtis and Edward Ashwood eds., W. B. Saunders and Company, p. 496).

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and capillary devices.

In another embodiment, the present invention provides a kit for the analysis of markers. Such a kit preferably comprises devises and reagents for the analysis of at least one test sample and instructions for performing the assay. Optionally the kits may contain one or more means for using information obtained from immunoassays performed for a marker panel to rule in or out certain diagnoses. Marker antibodies or antigens may be incorporated into immunoassay diagnostic kits depending upon which marker autoantibodies or antigens are being measured. A first container may include a composition comprising an antigen or antibody preparation. Both antibody and antigen preparations should preferably be provided in a suitable titrated form, with antigen concentrations and/or antibody titers given for easy reference in quantitative applications.

The kits may also include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present invention are generally well known in the art.

The reagents may also include ancillary agents such as buffering agents and protein stabilizing agents, e.g., polysaccharides and the like. The diagnostic kit may further include where necessary agents for reducing background interference in a test, agents for increasing signal, software and algorithms for combining and interpolating marker values to produce a prediction of clinical outcome of interest, apparatus for conducting a test, calibration curves and charts, standardization curves and charts, and the like.

In a more particular aspect the invention relates to a rapid multiple marker panel containing antibodies to selected markers that employs latex agglutination. Thus, in one embodiment the invention provides a kit for diagnosing stroke or stroke sub-type comprising: (1) an agglutinating immunosorbent for said selected markers, and (2) a control such as saline or a known concentration of said selected markers.

In another embodiment the invention relates to a kit for detecting various markers indicative of stroke or stroke sub-type diagnosis comprising: (1) an immunosorbent for selected markers indicative of stroke or stroke subtype diagnosis, and (2) an indicator reagent comprising secondary antibodies attached to a signal generating compound for each individual marker. The secondary antibodies can be specific for each individual marker or for the primary antibodies in the immunosorbent. In a preferred embodiment the kits further comprise an immunosorbent for glutamate or polyglutamate, and/or an immunosorbent for homocysteine or polyhomocysteine, and secondary antibodies against the glutamate and/or homocysteine, or to the primary antibodies on the immunosorbents against the glutamate or homocysteine. The immunosorbent preferably comprises anti-antibodies for the biomarkers bound to a solid support.

In another aspect the present invention relates to a test-kit that relies upon PCR amplification for measuring selected markers indicative of stroke or stroke subtype diagnosis. Thus, in another embodiment the invention provides a kit comprising: (a) one or more oligonucleotide primers attached to a solid phase, (b) indicator reagent attached to a signal-generating compound capable of generating a detectable signal from oligonucleotides, and, (c) a control sample (i.e. template cDNA). The reagents may also include ancillary agents such as buffering agents, polymerase agents, and the like. The diagnostic kit may further include, where necessary, other members of the signal-producing system of which system the detectable group is a member (e.g., enzyme and non-enzyme substrates), agents for reducing background interference in a test, agents for increasing the signal, apparatus for conducting a test, and the like.

In another embodiment of test-kit comprises (a) a solid phase to which biological fluids for receiving total DNA including selected marker cDNA indicative of stroke or stroke subtype diagnosis could be attached, (b) oligonucleotide primers, preferably in a ready-to-use PCR buffer, and (c) a control sample (i.e. template cDNA). Ancillary agents as described above may similarly be included.

In another embodiment the invention provides a diagnostic kit for detecting selected markers indicative of stroke or stroke subtype diagnosis autoantibodies comprising (a) a polypeptide of the selected markers indicative of stroke or stroke subtype diagnosis, fragment thereof, or analog or derivative thereof, (b) an indicator reagent comprising a secondary antibody specific for the autoantibody or the polypeptide attached to a signal-generating compound; and (c) a control sample, such as a known concentration of said selected markers indicative of stroke or stroke subtype diagnosis polyclonal antibodies. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme and non- enzyme substrates), agents for reducing background interference in a test, agents to increase the signal, apparatus for conducting a test, calibration and standardization information or instructions, and the like.

Methodology of Marker Selection, Analysis, and Classification

Non-linear techniques for data analysis and information extraction are important for identifying complex interactions between markers that contribute to overall presentation of the clinical outcome. However, due to the many features involved in association studies such as the one proposed, the construction of these in-silico predictors is a complex process. Often one must consider more markers to test than samples, missing values, poor generalization of results, selection of free parameters in predictor models, confidence in finding a sub- optimal solution and others. Thus, the process for building a predictor is as important as designing the protocol for the association studies. Errors at each step can propagate downstream, affecting the generalizability of the final result.

We now provide an overview of our process of model development, describing the five main steps and some techniques that the instant invention will use to build an optimal biomarker panel of response for each clinical outcome. One of ordinary skill in the art will know that it is best to use a 'toolbox' approach to the various steps, trying several different algorithms at each step, and even combining several as in Step Five. Since one does not know a priori the distribution of the true solution space, trying several methods allows a thorough search of the solution space of the observed data in order to find the most optimal solutions (i.e. those best able to generalize to unseen data). One also can give more confidence to predictions if several independent techniques converge to a similar solution.

Data Pre-processing

After assaying the patients for various markers, it is necessary to perform some basic data 'inspection', such as identification of outliers, before starting a program of outcome prediction. Another task is performing data dimensional shifting in the case of discrete data sets such as markers which only have a fixed number of values. For instance, one can describe a three-state protein marker value vector either three-dimensionally (1,0,0);(0,1,0);(0,0,1) or two-dimensionally (0,0);(1,0);(0,1). For some algorithms, the latter description may have a direct effect on computational cost and classifier accuracy: one can, in effect, collapse several values to a single parameter. The advantage of single parameter is that one can reduce dimensionality with little or no effect on the selection of the optimal feature set. Following pre-processing, one can then perform univariate and multivariate statistical modeling to identify strongly correlative outcome variables and determine a baseline outcome analysis.

Missing Value Estimation

While the call rate and accuracy of high throughput methods are improving, genotype and proteomic data sets usually contain missing values. Missing values arise from missed genotype calls or from the combination of data collected under different protocols. If subsequent analysis requires complete data sets, repeating the experiment can be expensive and removing rows or columns containing missing values in the data set may be wasteful.

Missing values can be replaced with the most likely genotype based on frequency estimates for an individual marker. This row counting method may be sufficient when few markers are genotyped, but it is not optimal for genome wide scans since it does not consider correlation in the data. Other statistical approaches to estimating missing values apply genetic models of inheritance. In large-scale association studies of unrelated participants, lineage information is unavailable. For the dataset gathered in the instant invention, we will apply techniques that do not use complex models and take into account the possibly discrete nature of marker data when models are used. These methods fall into two categories: KNN-based and Bayesian-based methods.

KNN estimates the value of the missing data as the most prevalent genotype among the K Nearest Neighbors. For a data set consisting of M patients and N SNPs, the data is stored in an M by N matrix. For each row with a missing value in a single column, the algorithm locates the K nearest neighbors in the N-1 dimensional subspace. The K nearest neighbors then votes to replace the missing value under majority rule. Ties are broken by random draw. If there are n missing values present in a row, we find the nearest neighbors in the N-n subspace.

The only other consideration is what distance function to use to determine the K nearest neighbors. Typically, the Euclidean distance is well suited for continuous data and the Hamming distance for nominal data. The Hamming distance counts the number of different marker genotypes in the N-n subspace and does not impose an artificial ordinality as does the Euclidean distance. There are other options such as the Manhattan distance, the correlation coefficient, and others that may be used depending on the data set distribution.

In contrast, Bayesian imputation uses probabilities instead of distances to infer missing values. The objective is to draw an inference about a missing value for a matrix entry in the data set from the posterior probability of the missing value given the observed data, $p(Y_{miss}|Y_{obs})$, where $Y_{obs}$ is the set of N-n observed marker values and $Y_{miss}$ is the missing value. By Bayes's theorem, $p(Y_{miss}|Y_{obs})$ can be expressed as follows:

$$\pi(Y_{miss} \mid Y_{obs}) = \frac{\pi(Y_{obs} \mid Y_{mis})\pi(Y_{miss})}{\sum_{k=1}^{m} \pi(Y_{obs} \mid Y_{mis})\pi(Y_{miss})} \quad (1)$$

where $\pi(Y_{miss})$ is the probability that a randomly selected missing entry will have the value $Y_{miss}$, $\pi(Y_{obs}|Y_{miss})$ is the probability of observing the N-n genotypes given $Y_{miss}$, and the sum is over the m possible values for $Y_{miss}$.

The likelihood model assumes that the probabilities π ($Y_{obs}|Y_{miss}$) can be expressed as functions of unknown parameters of the genotypes $Y_{miss}$:

$$\pi(Y_{obs-g} | Y_{miss-k}) = \pi(y_{g1} | \theta_{1k})\pi(y_{g2} | \theta_{2k}) \ldots \pi(y_{gn} | \theta_{nk}) \quad (2)$$

$$= \prod_{i=1}^{N-n} \pi(y_{gi} | \theta_{ik})$$

where $\theta_{ik}$ are unknown parameters of $Y_{miss}$ for the N-n observed markers, $y_{gi}$ is the i th marker in the set of $Y_{obs}$ markers, and $\theta(y_{gi}|\theta_{ik})$ is the probability of observing $y_{gi}$ given the parameter $\theta_{ik}$ of the marker value $Y_{miss}$ for variable i. The model is based on the assumption that the probability of observing $y_{gi}$ is independent of the probability of observing $y_{gj}$ for each marker value $Y_{miss}$ with i≠j.

Missing values are imputed as follows. For each marker for which there is a missing value, the probabilities θ ($y_{gi}|\theta_{ik}$) are estimated based on the observed markers. Using Bayes' theorem, the posterior probability θ ($Y_{miss}|Y_{obs}$) is calculated. We then sample $Y_{miss}$ from the posterior. This approach treats the missing value problem as a supervised learning problem in which posterior probability is learned from the pattern of observed markers.

Feature Selection

Following missing value replacement, the third step in the predictive panel building process is to perform feature selection on the dataset; this is perhaps the most important step in the predictor development process. Feature selection serves two purposes: (1) to reduce dimensionality of the data and improve classification accuracy, and (2) to identify biomarkers that are relevant to the cause and consequences of disease and drug response.

A feature selection algorithm (FSA) is a computational solution that given a set of candidate features selects a subset of relevant features with the best commitment among its size and the value of its evaluation measure. However, the relevance of a feature, as seen from the classification perspective, may have several definitions depending on the objective desired. An irrelevant feature is not useful for classification, but not all relevant features are necessarily useful for classification.

Another problem from which many classification methods suffer is the curse of dimensionality. That is, as the number of features in a classification task increases, the time requirements for an algorithm grow dramatically, sometimes exponentially. Therefore, when the set of features in the data is sufficiently large, many classification algorithms are simply intractable. This problem is further exacerbated by the fact that many features in a learning task may either be irrelevant or redundant to other features with respect to predicting the class of an instance. In this context, such features serve no purpose except to increase classification time.

FSAs can be divided into two categories based on whether or not feature selection is done independently of the learning algorithm used to construct the classifier. If the feature selection is independent of the learning algorithm, the technique is said to follow a filter approach. Otherwise, it is said to follow a wrapper approach. While the filter approach is generally computationally more efficient than the wrapper approach, a drawback is that an optimal selection of features may not be independent of the inductive and representational biases of the learning algorithm to be used to construct the classifier.

SFS/SBS

A sequential forward search (SFS), or backward (SBS), is a process that uses an iterative technique for feature selection. In this wrapper technique, one feature at a time is added (SFS) or deleted (SBS) to a set of pre-selected features, and iterated according to a performance metric until the 'optimal' set of features are obtained. For example, SFS is a technique that starts with all possible two-variable input combinations from the entire data set and then builds, one variable at a time, until an optimally performing combination of variables is identified. For instance, with 9 input variables labeled 1-9 (each with a binary descriptor), the two-variable combinations would comprise 1|2, 1|3, 1|4, 1|5, 1|6, 1|7, 1|8, 1|9, 2|3, 2|4, 2|5, 2|6 . . . 8|9. These input combinations are each used in training a classifier using the collected data. The combinations that perform the best (evaluated using leave-one-out cross validation; top 10%, for example) are selected for continued addition of variables. Let us say that 2|3 is selected as one of the top performers, it would then be coupled to each of the other variables, not including those variables that are already included in the combination. This would result in 2|3|1, 2|3|4, 2|3|5, 2|3|6, 2|3|7, 2|3|8 and 2|3|9. This coupling is performed for all of the top two-variable performers. The resultant three-variable input combinations are used to train a classifier using the collected data and then evaluated. The top performers are selected and then coupled again with all variables in the group, again used to train a classifier. This is repeated until a maximal predictive accuracy is achieved. In our experience we have noticed a well defined 'hump' at the point where the addition of variables into the system results begins to contribute to degradation of system performance.

SBS starts with the full set of features and eliminates those based upon a performance metric. Although in theory, going backward from the full set of features may capture interacting features more easily, the drawback of this method is that it is computationally expensive.

An example of this is described in U.S. patent application Ser. No. 09/611,220, incorporated in entirety with all figures by reference, which uses a variation on the SBS technique. In this method, a Genetic Algorithm is used in combination with a neural network to create and select child features based upon a fitness ranking that takes into effect multiple performance measures such as sensitivity and specificity. Only top-ranked child features are used in iterating the algorithm forward.

SFFS

The SFS algorithm suffers from a so-called nesting effect. That is, once a feature has been chosen, there is no way for it to be discarded. To overcome this problem, the sequential forward floating algorithm (SFFS) was proposed. SFFS is an exponential cost algorithm that operates in a sequential manner. In each selection step SFFS performs a forward step followed by a variable number of backward ones. In essence, a feature is first unconditionally added and then features are removed as long as the generated subsets are the best among their respective size. The algorithm is so-called because it has the characteristic of floating around a potentially good solution of the specified size.

E-RFE

The Recursive Feature Elimination (RFE) is a well-known feature selection method for support vector machines (SVMs). As a brief overview, a SVM realizes a classification function $$f(x) = \sum_{i=1}^{N} \alpha_i \gamma_i K(x_i, x) + b,$$

where the coefficients $\alpha=(\alpha_i)$ and b are obtained by training over a set of examples $S=\{(x_i, y_i) | i=1, \ldots, N, x_i \in R^n, y_i \in \{-1, 1\}\}$ and) $K(x_i, x)$ is the chosen kernel. In the linear case, the SVM expansion defines the hyperplane $$f(x) = <w, x> + b, \text{ with } w = \sum_{i=1}^{N} \alpha_i \gamma_i x_i.$$

The idea is to define the importance of a feature for a SVM in terms of its contribution to a cost function J ($\alpha$). At each step of the RFE procedure, a SVM is trained on the given data set, J is computed and the feature less contributing to J is discarded. In the case of linear SVM, the variation due to the elimination of the i-th feature is $\delta J(i) = w_i^2$; in the non linear case, $\delta J(i) = 1/2\alpha^t Z\alpha - \frac{1}{2}\alpha^t Z(-i) \alpha$, where $Z_{ij} = y_i y_j K(x_i, x_j)$. The heavy computational cost of RFE is a function of the number of variables, as another SVM must be trained each time a variable is removed. In the standard RFE algorithm we would eliminate just one of the many features corresponding to a minimum weight, while it would be convenient to remove all of them at once. We will go further in the instant invention by developing an ad hoc strategy for an elimination process based on the structure of the weight distribution. This strategy was first described by Furlanello. We introduce an entropy function H as a measure of the weight distribution. To compute the entropy, we split the range of the weights, normalized in the unit interval, into $n_{int}$ intervals (with $n_{int} = \sqrt{\#R}$), and we compute for each interval the relative frequencies $$p_i = \frac{\#\delta J(i)}{\#R}, i = 1, \ldots, n_{int}$$

Entropy is then defined as the following function:

$$H = -\sum_{i=1}^{n_{int}} p_i \log_2 p_i$$

The following inequality immediately descends from the definition of entropy: $0 \leq H \leq \log_2 n_{int}$, the two bounds corresponding to the situations:

H=0; or all the weights lie in one interval;

H=$\log_2 n_{int}$; or all the intervals contain the same number of weights.

The new entropy-based RFE (E-RFE) algorithm eliminates chunks of features at every loop, with two different procedures applied for lower or higher values of H. The distinction is needed to remove many features that have a similar (low) weight while preserving the residual distribution structure, and also allowing for differences between classification problems. E-RFE has been shown to speed up RFE by a factor of 100.

URG

One filter method especially suited for ordinal data has been developed recently by the authors of the instant invention, and offers clearly interpretable results on such data. The feature selection aspect, tentatively named URG, or Universal Regressor Gauge, is a general method for scoring and ranking the predictive sensitivity of input variables by fitting the gauge, or the scaling, on each of the input variables subject to both predictive accuracy of a nonparametric regression, and a penalty on the L1 norm of the vector of scaling parameters. The result is a sampled-gradient local minimum solution that does not require assumptions of linearity or exhaustive power-set sampling of subsets of variables. The approach penalizes the gauge $\theta$, or the set of scaling parameters ($\theta_1, \theta_2, \ldots, \theta_n$), applied to each of the input variables. The authors of the instant invention generalized this method to potentially nonlinear, nonparametric models of arbitrary complexity using a kernel-based nonparametric regressor. The penalty on the gauge is regularized by a coefficient I that is scanned across a range of values to put progressively more downward pressure on the scaling parameters, forcing the scale (and the resulting significance in distance-based regression) downward first on those variables that can be most easily eliminated without sacrificing accuracy. Because this process is analog in the state-space of the gauge, nonlinear interactions between subsets can be investigated in a continuous manner, even if the variables themselves are discrete-valued.

Other FSAs that are contemplated by, but not limited to, to be used in the instant invention include HITON Markov Blankets and Bayesian filters.

Classification

The fourth step in the predictor-building process is classification. In the supervised learning task, one is given a training set of labeled fixed-length feature vectors, from which to induce a classification model. This model, in turn, is used to predict the class label for a set of previously unseen instances. Thus, in building a classification model, the information about the class that is inherent in the features is of utmost importance. The dataset that the classifier is trained upon is broken up generally into three different sets: Training, Testing, and Evaluation. This is required since when using any classifier, the use of distinct subsets of the available data for training and testing is required to ensure generalizability. The parameters of the classifier are set with respect to the training data set, and judged versus competitors on the testing data set, and validated on the evaluation data set. To avoid over-training (i.e., memorization of features in a specific data set that are not applicable in a general manner) this succession of training steps is discontinued when the error on the validation set begins to increase significantly. We use the error on the evaluation data set as an estimate of how well we can expect our classifier to perform on new testing data as it becomes available. This estimate can be measured by 10× leave-one-out-cross-validation on the evaluation set (100× in cases of low sample number), or batch evaluation on larger data sets.

Classifiers complimentated for the instant invention include, but are not limited to, neural networks, support vector machines, genetic algorithms, kernel-based methods, and tree-based methods.

Neural Networks

One tool to use construct classifiers is that of a mapping neural network. The flexibility of neural nets to generically model data is derived through a technique of "learning". Given a list of examples of correct input/output pairs, a neural net is trained by systematically varying its free parameters (weights) to minimize its chi-squared error in modeling the training data set. Once these optimal weights have been determined, the trained net can be used as a model of the training data set. If inputs from the training data are fed to the neural net, the net output will be roughly the correct output contained in the training data. The nonlinear interpolatory ability manifests itself when one feeds the net sets of inputs for which no examples appeared in the training data. A neural net "learns" enough features of the training data set to completely reproduce it (up to a variance inherent to the training data); the trained form of the net acts as a black box that produces outputs based on the training data.

Neural networks typically have a number of ad hoc parameters, such as selection of the number of hidden layers, the number of hidden-layer neurons, parameters associated with the learning or optimization technique used, and in many cases they require a validation set for a stopping criterion. In addition, neural network weights are trained iteratively, producing problems with convergence to local minima. We have developed several types of neural networks that solve these problems. Our solutions involve nonlinearly transforming the input pattern fed into the neural network. This transformation is equivalent to feature selection (though one still needs as many inputs into the classifier) and can be quite powerful when combined with the independent feature selection techniques previously described.

Genetic Algorithms

Genetic algorithms (GAs) typically maintain a constant sized population of individual solutions that represent samples of the space to be searched. Each individual is evaluated on the basis of its overall "fitness" with respect to the given application domain. New individuals (samples of the search space) are produced by selecting high performing individuals to produce "offspring" that retain features of their "parents". This eventually leads to a population that has improved fitness with respect to the given goal.

New individuals (offspring) for the next generation are formed by using two main genetic operators: crossover and mutation. Crossover operates by randomly selecting a point in the two selected parents gene structures and exchanging the remaining segments of the parents to create new offspring. Therefore, crossover combines the features of two individuals to create two similar offspring. Mutation operates by randomly changing one or more components of a selected individual. It acts as a population perturbation operator and is a means for inserting new information into the population. This operator prevents any stagnation that might occur during the search process.

GAs have demonstrated substantial improvement over a variety of random and local search methods. This is accomplished by their ability to exploit accumulating information about an initially unknown search space in order to bias subsequent search into promising subspaces. Since GAs are basically a domain independent search technique, they are ideal for applications where domain knowledge and theory is difficult or impossible to provide.

SVMs

The key idea behind support vector machines (SVMs, Vapnik, 1995) is to map input vectors (i.e., patient-specific data) into a high dimensional space, and to construct in that space hyperplanes with a large margin. These hyperplanes can be thought of as boundaries separating the categories of the dataset, in this case response and non-response. The support vector machine solution proposes to find the hyperplane separating the classes. This plane is determined by the parameters of a decision function, which is used for classification. The SVM is based on the fact that there is a unique separating hyperplane that maximizes the margin between the classes.

The task of finding the hyperplane is reduced to minimizing the Lagrangian, a function of the margin and constraints associated with each input vector. The constraints depend only on the dot product of an input element and the solution vector. In order to minimize the Langrangian, the Lagrange multipliers must either satisfy those constraints or be exactly zero. Elements of the training set for which the constraints are satisfied are the so-called support vectors. The support vectors parameterize the decision function and lie on the boundaries of the margin separating the classes.

In many cases, SVMs are typically more accurate, give greater data understanding, and are more robust than other machine learning methods. Data understanding comes about because SVMs extract support vectors, which as described above are the borderline cases. Exhibiting such borderline cases allow us to identify outliers, to perform data cleaning, and to detect confounding factors. In addition, the margins of the training examples (how far they are from the decision boundary) provide useful information about the relevance of input variables, and allow the selection of the most predictive variable. SVMs are often successful even with sparse data (few examples), biased data (more examples of one category), redundant data (many similar examples), and heterogeneous data (examples coming from different sources). However, they are known to work poorly on discrete data.

In another preferred embodiment of the present invention, regression techniques are used to deliver a diagnostic or prognostic prediction using the markers declared previously. These are well-known by those of ordinary skill in the art, however a short discussion follows. For more detail, one is referred to Kleinbaum et al., Applied Regression Analysis and Multivariable Methods, Third Edition, Duxbury Press, 1998.

In the discussion of weighted least squares a need was found for a method to fit Y to more than one X. Further, it is common that the response variable Y is related to more than one regressor variable simultaneously. If a valid description of the relationship between Y and any of these response variables is to be obtained, all must be considered. Also, exclusion of any important regressor variables will adversely affect predictions of Y. In general, the equation to be considered becomes $$Y = b0 + b1X1 + b2X2 + \ldots + bKXK$$

The Xs may be any relevant regressor variables. Often one X is a (nonlinear) transformation of another. For example, X 2=ln (X 1).

When dealing with multiple linear regression, fits to data are no longer lines. For example, with K=2, the resulting fit would describe a plane in three dimensional space with "slopes" bhat 1 and bhat 2 intersecting the Y axis at bhat 0. Beyond K=2 the resulting fit becomes difficult to visualize. The terminology regression surface is often used to describe a multiple linear regression fit.

Assumptions required for application of least squares methodology to multiple linear regression equations are similar to those cited for the simple linear case. For example, the true relationship between Y and the various Xs must be as given by the linear equation and the spread of the errors must be constant across values of all Xs. Also, a limit exists to the number of Xs that can be considered. Specifically, K+1 must be less than or equal to the sample size n for a unique set of bhats to be found.

In theory, least squares estimates of b 0, . . . , b K are found just as in the simple linear case. The estimates bhat 0, . . . , bhat K are the solution from minimizing sum (Yi−b0−b1×1i . . . −bk×ki)sup2.

The description of the resulting equations and associated summary statistics is best made using matrix algebra. The computations are best carried out using a computer.

The relationship between Y and X or Y and several Xs is not always linear in form despite transformations that can be applied to resulted in a linear relationship. In some instances such a transformation may not exist and in others theoretical concerns may require analysis to be carried out with the untransformed equation.

Least squares methodology can be used to solve nonlinear regression problems. For the above equation the least squares estimates of the parameters would be the solution of the minimization of sum(W−A (1−e sup Bt)sup C)sup 2

Application of calculus leads to three equations whose solution requires an iterative technique. For all but the simplest of cases, solving nonlinear least squares problems involves use of computer-based algorithms. A multitude of such algorithms exist emphasizing the number of problems whose valid solution requires the nonlinear least squares technique.

Several variations of nonlinear regression exist, which one of ordinary skill in the art will be aware. One preferred case in the present invention is the use of deterministic greedy algorithms for building sparse nonlinear regression models from observational data. In this embodiment, the objective is to develop efficient numerical schemes for reducing the training and runtime complexities of nonlinear regression techniques applied to massive datasets. In the spirit of Natarajan's greedy algorithm (Natarajan, 1995), the procedure is to iteratively minimize a loss function subject to a specified constraint on the degree of sparsity required of the final model or an upper bound on the empirical error. There exist various greedy criteria for basis selection and numerical schemes for improving the robustness and computational efficiency of these algorithms.

In another preferred embodiment of the present invention, a kernel-based method is trained to deliver a diagnostic or prognostic prediction using the markers declared previously. One such method is Kernel Fisher's Discriminant (KFD). Fisher's discriminant (Fisher, 1936) is a technique to find linear functions that are able to discriminate between two or more classes. Fisher's idea was to look for a direction w that separates the class means values well (when projected onto the found direction) while achieving a small variance around these means. The hope is that it is easy to differentiate between either of the two classes from this projection with a small error. The quantity measuring the difference between the means is called between class variance and the quantity measuring the variance around these class means is called within class variance, respectively. The goal is to find a direction that maximizes the between class variance while minimizing the within class variance at the same time. As this technique has been around for almost 70 years it is well known and widely used to build classifiers.

Unfortunately, as previously discussed, many biological datasets are not solvable using linear techniques. Therefore, one of the classifiers we use is a non-linear variant of Fisher's discriminant. This non-linearization is made possible through the use of kernel functions, a "trick" that is borrowed from support vector machines (Boser et al., 1992). Kernel functions represent a very principled and elegant way of formulating non-linear algorithms, and the findings that are derived from using them have clear and intuitive interpretations.

In the KFD technique (Mika, 1999), one first maps the data into some feature space through some non-linear mapping. One then computes Fisher's linear discriminant in this feature space, thus implicitly yielding a non-linear discriminant in input space. In a methodology similar to SVMs, this mapping is defined in terms of a kernel function $k(x,y)=(\Phi(x) \cdot \Phi(y))$. The training examples (i.e. the data vector containing all marker values for each patient) can in turn be expanded in terms of this kernel function as well. From this relationship one can write a formulation of the between and within class variance in terms of dot products of the kernel function and training patterns and thus find Fisher's linear discriminant in F by maximizing the ratio of these two quantities.

In another preferred embodiment of the present invention, an algorithm using Bayesian learning is trained to deliver a diagnostic or prognostic prediction using the markers declared previously. See Pearl, J. (1988). Probabilistic Reasoning in Intelligent Systems: networks of plausible inference, Morgan Kaufmann, for an overview of Bayesian learning.

While Bayesian networks (BNs) are powerful tools for knowledge representation and inference under conditions of uncertainty, they were not considered as classifiers until the discovery that Naïve-Bayes, a very simple kind of BNs that assumes the attributes are independent given the class node, are surprisingly effective. See Langley, P., Iba, W. and Thompson, K. (1992). An analysis of Bayesian classifiers. In Proceedings of AAAI-92 pp. 223-228.

A Bayesian network B is a directed acyclic graph (DAG), where each node N represents a domain variable (i.e., a dataset attribute), and each arc between nodes represents a probabilistic dependency, quantified using a conditional probability distribution (CP table) for each node $n.sub.i$. A BN can be used to compute the conditional probability of one node, given values assigned to the other nodes; hence, a BN can be used as a classifier that gives the posterior probability distribution of the class node given the values of other attributes. A major advantage of BNs over many other types of predictive models, such as neural networks, is that the Bayesian network structure represents the inter-relationships among the dataset attributes. One of ordinary skill in the art can easily understand the network structures and if necessary modify them to obtain better predictive models. By adding decision nodes and utility nodes, BN models can also be extended to decision networks for decision analysis. See Neapolitan, R. E. (1990), Probabilistic reasoning in expert systems: theory and algorithms, John Wiley & Sons.

Applying Bayesian network techniques to classification involves two sub-tasks: BN learning (training) to get a model and BN inference to classify instances. Learning BN models can be very efficient. As for Bayesian network inference, although it is NP-hard in general (See for instance Cooper, G. F. (1990) Computational complexity of probabilistic inference using Bayesian belief networks, In Artificial Intelligence, 42 (pp. 393-405).), it reduces to simple multiplication in a classification context, when all the values of the dataset attributes are known.

The two major tasks in learning a BN are: learning the graphical structure, and then learning the parameters (CP table entries) for that structure. One skilled in the art knows it is easy to learn the parameters for a given structure that are optimal for a given corpus of complete data, the only step being to use the empirical conditional frequencies from the data.

There are two ways to view a BN, each suggesting a particular approach to learning. First, a BN is a structure that encodes the joint distribution of the attributes. This suggests that the best BN is the one that best fits the data, and leads to the scoring based learning algorithms, that seek a structure that maximizes the Bayesian, MDL or Kullback-Leibler (KL) entropy scoring function. See for instance Cooper, G. F. and Herskovits, E. (1992). A Bayesian Method for the induction of probabilistic networks from data. Machine Learning, 9 (pp. 309-347). Second, the BN structure encodes a group of conditional independence relationships among the nodes, according to the concept of d-separation. See for instance Pearl, J. (1988). Probabilistic Reasoning in Intelligent Systems: networks of plausible inference, Morgan Kaufmann. This suggests learning the BN structure by identifying the conditional independence relationships among the nodes. These algorithms are referred as CI-based algorithms or constraint-based algorithms. See for instance Cheng, J., Bell, D. A. and Liu, W. (1997a). An algorithm for Bayesian belief network construction from data. In Proceedings of AI & STAT'97 (pp. 83-90), Florida.

Friedman et al. (1997) show theoretically that the general scoring-based methods may result in poor classifiers since a good classifier maximizes a different function-viz., classification accuracy. Greiner et al. (1997) reach the same conclusion, albeit via a different analysis. Moreover, the scoring-based methods are often less efficient in practice. The preferred embodiment is CI-based learning algorithms to effectively learn BN classifiers.

The present invention envisions using, but is not limited to, the following five classes of BN classifiers: Nafve-Bayes, Tree augmented Naïve-Bayes (TANs), Bayesian network augmented Naïve-Bayes (BANs), Bayesian multi-nets and general Bayesian networks (GBNs). By use of this methodology it is possible to build a predictive model of the data.

These models can be put on firm theoretical foundations of statistics and probability theory, i.e. in a Bayesian setting. The computation required for inference in these models include optimization or marginalisation over all free parameters in order to make predictions and evaluations of the model. Inference in all but the very simplest models is not analytically tractable, so approximate techniques such as variational approximations and Markov Chain Monte Carlo may be needed. Models include probabilistic kernel based models, such as Gaussian Processes and mixture models based on the Dirichlet Process.

Ensemble Networks

The final step in predictor development, assembly of committee, or ensemble, networks. It is common practice to train many different candidate networks and then to select the best, on the basis of performance on an independent validation set, for instance, and to keep this network, discarding the rest. There are two disadvantages to this approach. First, the effort involved in training the remaining networks is wasted. Second, the generalization performance on the validation set has a random component due to noise on the data, and so the network that had the best performance on the validation set might not be the one with the best performance on the new test set.

These drawbacks can be overcome by combining the networks together to form a committee. This can lead to significant improvements in the predictions on new data while involving little additional computational effort. In fact, the performance of a committee can be better than the performance of the best single network in isolation. The error due to the committee can be shown to be:

$$E_{COM} = 1/L \, E_{AV}$$

Where L is the number of committee members and EAV the average error contributed to the prediction by a single member of the committee. Typically, some useful reduction in error is obtained, and the method is trivial to implement.

The challenging problem of integration is to decide which one(s) of the classifiers to rely on or how to combine the results produced by the base classifiers. One of the most popular and simplest techniques used is called majority voting. In the voting technique, each base classifier is considered as an equally weighted vote for that particular prediction. The classification that receives the largest number of votes is selected as the final classification (ties are solved arbitrarily). Often, weighted voting is used: each vote receives a weight, which is usually proportional to the estimated generalization performance of the corresponding classifier. Weighted Voting (WV) works usually much better than simple majority voting.

Boosting Networks

Boosting has been found to be a powerful classification technique with remarkable success on a wide variety of problems, especially in higher dimensions. It aims at producing an accurate combined classifier from a sequence of weak (or base) classifiers, which are fitted to iteratively reweighted versions of the data.

In each boosting iteration, m, the observations that have been misclassified at the previous step have their weights increased, whereas the weights are decreased for those that were classified correctly. The $m_{th}$ weak classifier f(m) is thus forced to focus more on individuals that have been difficult to classify correctly at earlier iterations. In other words, the data is re-sampled adaptively so that the weights in the re-sampling are increased for those cases most often misclassified. The combined classifier is equivalent to a weighted majority vote of the weak classifiers.

Entropy-based

One efficient way to construct an ensemble of diverse classifiers is to use different feature subsets. To be effective, an ensemble should consist of high-accuracy classifiers that disagree on their predictions. To measure the disagreement of a base classifier and the whole ensemble, we calculate the diversity of the base classifier over the instances of the validation set as an average difference in classifications of all possible pairs of classifiers including the given one. A measure of this is based on the concept of entropy:

$$\text{div\_ent} = \frac{1}{N} \sum_{i=1}^{N} \sum_{k=1}^{l} -\frac{N_k^l}{S} \cdot \log\left(\frac{N_k^l}{S}\right)$$

where N is the number of instances in the data set, S is the number of base classifiers, l is the number of classes, and $N_k^l$ is the number of base classifiers that assign instance i to class k.

BRIEF DESCRIPTION OF THE DRAWINGS

In the following, the invention will be explained in further detail with reference to the drawings, in which:

FIG. 1 is a table illustrating clinical parameter among a set of hemorrhagic patients and a set of non-hemhorragic patients;

FIG. 2 is a set of box plots showing baseline plama c-Fn levels at admission in patient who received tPA within 3 and 6 hours;

FIG. 3 is a set of box plots showing baseline plama MMP-9 levels at admission in patient who received tPA within 3 and 6 hours, and;

FIG. 4 is a table illustrating adjusted odds ration of hemorrhagic transformation treated within 6 hours of symptoms onset.

METHOD FOR DEFINING PANELS OF MARKERS

In practice, data may be obtained from a group of subjects. The subjects may be patients who have been tested for the presence or level of certain markers. Such markers and methods of patient extraction are well known to those skilled in the art. A particular set of markers may be relevant to a particular condition or disease. The method is not dependent on the actual markers. The markers discussed in this document are included only for illustration and are not intended to limit the scope of the invention. Examples of such markers and panels of markers are described in the instant invention and the incorporated references.

Well-known to one of ordinary skill in the art is the collection of patient samples. A preferred embodiment of the instant invention is that the samples come from two or more different sets of patients, one a disease group of interest and the other(s) a control group, which may be healthy or diseased in a different indication than the disease group of interest. For instance, one might want to look at the difference in blood-borne markers between patients who have had stroke and those who had stroke mimic to differentiate between the two populations.

The blood samples are assayed, and the resulting set of values are put into a database, along with outcome, also called phenotype, information detailing the illness type, for instance stroke mimic, once this is known. Additional clinical details such as time from onset of symptoms and patient physiological, medical, and demographics, the sum total called patient characteristics, are put into the database. The time from onset is important to know as initial marker values from onset of symptoms can change significantly over time on a timeframe of tens of minutes. Thus, a marker may be significant at one point in the patient history and not at another in predicting diagnosis or prognosis of cardiovascular disease, damage or injury. The database can be simple as a spreadsheet, i.e. a two-dimensional table of values, with rows being patients and columns being filled with patient marker and other characteristic values.

From this database, a computerized algorithm can first perform pre-processing of the data values. This involves normalization of the values across the dataset and/or transformation into a different representation for further processing. The dataset is then analyzed for missing values. Missing values are either replaced using an imputation algorithm, in a preferred embodiment using KNN or MVC algorithms, or the patient attached to the missing value is exised from the database. If greater than 50% of the other patients have the same missing value then value can be ignored.

Once all missing values have been accounted for, the dataset is split up into three parts: a training set comprising 33-80% of the patients and their associated values, a testing set comprising 10-50% of the patients and their associated values, and a validation set comprising 1-50% of the patients and their associated values. These datasets can be further sub-divided or combined according to algorithmic accuracy. A feature selection algorithm is applied to the training dataset. This feature selection algorithm selects the most relevant marker values and/or patient characteristics. Preferred feature selection algorithms include, but are not limited to, Forward or Backward Floating, SVMs, Markov Blankets, Tree Based Methods with node discarding, Genetic Algorithms, Regression-based methods, kernel-based methods, and filter-based methods.

Feature selection is done in a cross-validated fashion, preferably in a naïve or k-fold fashion, as to not induce bias in the results and is tested with the testing dataset. Cross-validation is one of several approaches to estimating how well the features selected from some training data is going to perform on future as-yet-unseen data and is well-known to the skilled artisan. Cross validation is a model evaluation method that is better than residuals. The problem with residual evaluations is that they do not give an indication of how well the learner will do when it is asked to make new predictions for data it has not already seen. One way to overcome this problem is to not use the entire data set when training a learner. Some of the data is removed before training begins. Then when training is done, the data that was removed can be used to test the performance of the learned model on "new" data.

Once the algorithm has returned a list of selected markers, one can optimize these selected markers by applying a classifier to the training dataset to predict clinical outcome. A cost function that the classifier optimizes is specified according to outcome desired, for instance an area under receiver-operator curve maximizing the product of sensitivity and specificity of the selected markers, or positive or negative predictive accuracy. Testing of the classifier is done on the testing dataset in a cross-validated fashion, preferably naïve or k-fold cross-validation. Further detail is given in U.S. patent application Ser. No. 09/611,220, incorporated by reference. Classifiers map input variables, in this case patient marker values, to outcomes of interest, for instance, prediction of stroke subtype. Preferred classifiers include, but are not limited to, neural networks, Decision Trees, genetic algorithms, SVMs, Regression Trees, Cascade Correlation, Group Method Data Handling (GMDH), Multivariate Adaptive Regression Splines (MARS), Multilinear Interpolation, Radial Basis Functions, Robust Regression, Cascade Correlation+Projection Pursuit, linear regression,. Non-linear regression, Polynomial Regression, Regression Trees, Multilinear Interpolation, MARS, Bayes classifiers and networks, and Markov Models, and Kernel Methods.

The classification model is then optimized by for instance combining the model with other models in an ensemble fashion. Preferred methods for classifier optimization include, but are not limited to, boosting, bagging, entropy-based, and voting networks. This classifier is now known as the final predictive model. The predictive model is tested on the validation data set, not used in either feature selection or classification, to obtain an estimate of performance in a similar population.

The predictive model can be translated into a decision tree format for subdividing the patient population and making the decision output of the model easy to understand for the clinician. The marker input values might include a time since symptom onset value and/or a threshold value. Using these marker inputs, the predictive model delivers diagnostic or prognostic output value along with associated error. The instant invention anticipates a kit comprised of reagents, devices and instructions for performing the assays, and a computer software program comprised of the predictive model that interprets the assay values when entered into the predictive model run on a computer. The predictive model receives the marker values via the computer that it resides upon.

Once patients are exhibiting symptoms of cardiovascular illness, for instance stroke, a blood sample is drawn from the patient using standard techniques well known to those of ordinary skill in the art and assayed for various blood-borne markers of cardiovascular illness. Assays can be preformed through immunoassays or through any of the other techniques well known to the skilled artisan. In a preferred embodiment, the assay is in a format that permits multiple markers to be tested from one sample, such as the Luminex platform™, and/or in a rapid fashion, defined to be under 30 minutes and in the most preferred enablement of the instant invention, under 15 minutes. The values of the markers in the samples are inputed into the trained, tested, and validated algorithm residing on a computer, which outputs to the user on a display and/or in printed format on paper and/or transmits the information to another display source the result of the algorithm calculations in numerical form, a probability estimate of the clinical diagnosis of the patient. There is an error given to the probability estimate, in a preferred embodiment this error level is a confidence level. The medical worker can then use this diagnosis to help guide treatment of the patient.

EXAMPLE I

Prospectively studied patients (n=87, 59% men; mean age 67±12 years) received intravenous tPA following the European Cooperative Acute Stroke Study (ECASS) II criteria. 12 Thrombolytic therapy was administered within 6 hours from the beginning of the symptoms at a dose of 0.9 mg/kg body weight, with an upper dose limit of 90 mg per patient. Ten percent of the total dose was given as a bolus over 1 to 2 minutes, followed by a 60-minute infusion of the remaining dose. The mean time to the infusion of the drug was 160_46 minutes. Seventy-one patients received the treatment within 3 hours from onset of symptoms, whereas 16 patients received tPA between 3 and 6 hours within onset of symptoms. Thirty healthy control subjects matched by age and sex (male: 57%; mean age: 63±9 years) and without history of neurological disorders or vascular risk factors were also included in the study. To determine the effect of stroke on the levels of the molecules, plasma c-Fn and MMP-9 concentrations were also determined in 100 patients with acute ischemic stroke who did not receive tPA treatment and in whom HT did not develop (male: 59%; mean age: 67±6 years; mean time to inclusion: 7.2_3.9 hours). Neither the patients nor the controls had inflammatory, hematological, or infectious diseases, cancer, or severe renal or liver failure. The ethics committee approved the protocol in each center, and informed consent was obtained from patients or their relatives. Medical history recording potential stroke risk factors, clinical examination, blood and coagulation tests, 12-lead electrocardiogram, chest radiography, and noncontrast cranial computed tomography (CT) scan were performed at admission. Stroke subtype was classified according to the Trial of Org 10172 in Acute Stroke Treatment (TOAST) criteria. 13 Stroke severity was assessed by a certified neurologist using the National Institutes of Health Stroke Scale (NIHSS) at admission and at 24 to 36 hours. Neurological deterioration was defined as death or an increase of ≧4 points in the NIHSS score between the 2 examinations.

Early CT signs of infarction were evaluated in the first radiological examination. The volume of hypodensity and the presence of HT were evaluated on a second cranial CT, which was performed 24 to 36 hours after treatment. Hypodensity volume was determined by using the formula 0.5×a×b×c, where a and b are the largest perpendicular diameters measured on CT and c is the slice thickness. The HT type was classified according to the ECASS II criteria. Hemorrhagic infarction type 1 (HI-1) was defined as small petechiae along the margins of the infarct, and HI type 2 (HI-2) was defined as more confluent petechiae within the infarct area but without a space-occupying effect. Parenchymal hemorrhage type 1 (PH-1) was defined as blood clots in ≦30% of the infarcted area with some slight space-occupying effect, and PH type 2 (PH-2) as blood clots in ≧30% of the infarcted area with substantial space-occupying effect. All CT examinations were performed by 1 investigator in each center blinded to the clinical and analytical data. Symptomatic HT was considered as being associated with neurological deterioration.

Laboratory Tests

Blood samples were taken from all patients at admission before tPA administration. Samples were collected in glass test tubes containing EDTA. Suspension of plasma was centrifuged at 3000 g for 5 minutes and immediately frozen and stored at −80° C. Plasma MMP-9 and c-Fn levels were measured with commercially available quantitative sandwich enzyme-linked immunoabsorbent assay kits obtained from Biotrack, Amersham Pharmacia UK, and Adeza Biomedical, respectively. Determinations were performed in an independent laboratory blinded to clinical and radiological data. The intra-assay and interassay coefficients of variation were <5% for MMP-9 and c-Fn determinations.

Proportions between groups were compared using the $\chi^2$ test. Continuous variables are expressed as mean±SD and were compared using the Student t test. Given that MMP-9 and c-Fn concentrations are not normally distributed, their levels were expressed as median (quartiles), and comparisons were made using the Mann-Whitney test or Kruskal-Wallis test as appropriate. The association between c-Fn levels and baseline continuous variables was assessed by calculating the Spearman correlation coefficient.

Statistical Analysis

We used cutoff values, as described by Robert et al, (Robert C, Vermont J, Bosson J L. Formulas for threshold computations. *Comput Biomed Res.* 1991;24:514-519.) to estimate the sensitivity, specificity, and predictive values of a specific concentration of plasma MMP-9 and c-Fn for HT. The importance of MMP-9 and c-Fn in the development of HT after tPA administration was determined by logistic regression analysis after adjusting for those variables evaluated at admission that were related to HT in the univariate analysis. Because plasma levels of c-Fn have been reported to increase with age and in patients with diabetes, these 2 variables were forced into the analysis. To test whether the odds of HT for c-Fn was modified by the volume of hypodensity, a second analysis was performed including this factor into the model. Plasma MMP-9 and c-Fn were included as continuous variables because the cutoff values meant that there was a linearity of the odds ratios.

Twenty-six (30%) of the 87 patients included in the study had HT. Fifteen patients (17.2%) had HI-1, 7 (8%) had HI-2, 2 (2.3%) had PH-1, and 2 (2.3%) had PH-2. Table 1 shows the main characteristics of patients with and without HT. The severity of neurological deficit at admission evaluated by the NIHSS score was significantly higher in patients with HT, who also displayed significantly greater volumes of hypodensity on the second cranial CT. Both clinical groups presented with similar systolic and diastolic blood pressures and glucose levels before tPA administration. Neurological deterioration was observed in 15 patients (17.2%). In 8 patients, the neurological worsening was associated with HT: 2 patients had HI-1, 3 displayed HI-2, and 3 had PH.

Results

Plasma c-Fn concentrations before tPA administration were significantly higher in patients with HT (4.8 [3.4, 5.9] μg/mL) than in those without HT (1.7 [1.4, 2.5]μg/mL) and both the healthy subjects (1.3 [0.9, 1.6]μg/mL) and the patients not treated with tPA (1.4 [1.1, 1.8]μg/mL) (all P<0.001). Moreover, we found that the greater the severity of the bleeding the higher the levels of c-Fn (FIG. 1A). A similar effect was found in those patients who were treated within 3 hours of onset of symptoms (n=71) (FIG. 1B). The levels of c-Fn were not statistically different in patients with symptomatic and asymptomatic HT, although there was a clear trend for the levels to be higher in patients with symptomatic HT. (5.8 [4.0, 6.9]μg/mL versus 4.5 [2.7, 5.4]μg/mL; P<0.054).

Plasma MMP-9 concentrations before tPA administration were also significantly higher in those patients with HT (170.3 [101.4, 196.2] ng/mL) than in those without HT (87.2 [54.8, 115.1] ng/mL) and in both the healthy subjects (53.7 [39.5, 79.4] ng/mL) and the patients not treated with tPA (62

[40, 93.8] ng/mL) (all P<0.001). As observed with c-Fn levels, the greater the severity of the bleeding, the higher the levels of MMP-9, both in patients treated within 6 (FIG. 2A) and 3 hours (FIG. 2B). No differences were found in MMP-9 levels between symptomatic and asymptomatic HT (170 [121, 214] ng/mL versus 170 [87, 194 ] ng/mL; P<0.338).

Plasma c-Fn concentrations were significantly higher in patients with early signs of ischemia (n=37) on cranial CT (2.8 [1.7, 5.0]μg/mL) than in those without (1.9 [1.4, 2.9]μg/mL) (P<0.012). Plasma c-Fn correlated positively with MMP-9 levels (r=0.671, P<0.001) and the hypodensity volume (r=0.364, P<0.001). No correlation was found between plasma c-Fn levels and other variables related to HT such as serum glucose concentrations, blood pressure levels, or the severity of neurological deficit at admission.

As shown in FIG. 4, only plasma c-Fn levels remained independently associated with HT after adjustment for age, history of diabetes, baseline NIHSS score, and plasma MMP-9 levels. The odds of c-Fn levels for HT did not substantially change after the inclusion of the volume of hypodensity into the analysis (OR, 2.1; 95% Cl, 1.3 to 3.4; P<0.002). Plasma c-Fn level was also the only factor independently associated with HT after adjustment for potential confounders when the analysis was limited to the 71 patients treated within 3 hours (OR, 1.9; 95% CI, 1.2 to 3.3; P<0.006). No interaction was found between MMP-9 and c-Fn.

Because it has been reported that HI-2 and PH occur more often in patients who receive tPA treatment, and also based on the observation of the authors results in FIG. 1 that clearly demonstrate higher levels of c-Fn in patients with HI-2 and PH, we calculated the c-Fn and MMP-9 cutoff values with the highest sensitivity and specificity for these types of HT. This post-hoc explanatory analysis showed that plasma MMP-9 concentrations >140 ng/mL predicted the development of HI-2 and PH with a sensitivity of 81%, specificity of 88%, positive predictive value of 41%, and negative predictive value of 98%. More interestingly, the sensitivity, specificity, and positive and negative predictive values of plasma c-Fn ≧3.6 μg/mL for the prediction of HI-2 and PH were 100%, 96%, 44%, and 100%, respectively.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of determining presence or risk of hemorrhage in a human patient, said method comprising:
    obtaining a test sample from the patient, wherein the sample is a plasma sample;
    forming a complex between an antibody probe to cellular fibronectin (c-Fn) and c-Fn present in the test sample;
    measuring the amount of the complex formed and determining the amount of c-Fn in the sample; and
    determining the presence of or future risk for hemorrhage in the patient when the level of c-Fn in the test sample is greater than 3.6 μg/mL 2. The method according to claim 1, wherein determining the risk of hemorrhage occurs following administration thrombolytic therapy.

3. The method according to claim 2, further comprising:
    determining the patient's risk of hemorrhage following thrombolytic therapy from said measured level of c-Fn; and
    administering a stroke therapy.

4. The method according to claim 3, where the risk of hemorrhage following thrombolytic therapy is risk of a parenchymal hemorrhage.

5. The method according to claim 3, where the risk of hemorrhage following thrombolytic therapy is risk of a parenchymal hemorrhage and the level of c-Fn in the patient's plasma is greater than 5.8 μg/mL.

6. The method according to claim 3, where the risk of hemorrhage following thrombolytic therapy is risk of a hemorrhagic infarction type 2.

7. The method according to claim 1, further comprising analyzing the obtained test sample for the proteomic marker MMP-9; and
    correlating the analyzed amount of the proteomic marker MMP-9 and the presence or amount of said c-Fn in order to determine the present or future risk of a hemorrhage for the subject.

8. A method of determining risk of hemorrhage transformation in a human patient receiving tissue plasminogen activator therapy for ischemic stroke, comprising:
    identifying a patient suffering from ischemic stroke;
    providing the patient with tissue plasminogen activator (t-PA) therapy;
    obtaining a test sample from the patient, wherein the sample is a plasma sample;
    forming a complex between an antibody probe against cellular fibronectin (c-Fn) and c-Fn present in the test sample;
    measuring the amount of the complex formed and determining the amount of c-Fn in the sample; and
    determining the presence of or future risk for hemorrhage transformation in the patient when the level of c-Fn in the test sample is greater than 3.6 μg/mL.

9. The method according to claim 8, wherein the risk of hemorrhage transformation following thrombolytic therapy is risk of a parenchymal hemorrhage.

10. The method according to claim 9, wherein the level of c-Fn in the patient's plasma is greater than 5.8 µg/mL.

11. The method according to claim 8, where the risk of hemorrhage following thrombolytic therapy is risk of a hemorrhagic infarction type 2.

* * * * *